US008168178B2

(12) United States Patent
Crompton

(10) Patent No.: US 8,168,178 B2
(45) Date of Patent: May 1, 2012

(54) METHODS AND COMPOSITIONS FOR REGULATING LYMPHOCYTE ACTIVITY

(75) Inventor: Tessa Crompton, London (GB)

(73) Assignee: Curis, Inc., Lexington, MA (US)

( * ) Notice: Subject to any disclaimer, the term of this patent is extended or adjusted under 35 U.S.C. 154(b) by 966 days.

(21) Appl. No.: 11/061,869

(22) Filed: Feb. 18, 2005

(65) Prior Publication Data

US 2005/0256074 A1    Nov. 17, 2005

Related U.S. Application Data

(60) Continuation-in-part of application No. 09/724,964, filed on Nov. 28, 2000, now Pat. No. 6,951,839, which is a continuation-in-part of application No. 10/989,693, filed on Nov. 16, 2004, now abandoned, which is a division of application No. 09/724,964, filed on Nov. 28, 2000, now Pat. No. 6,951,839.

(60) Provisional application No. 60/546,571, filed on Feb. 20, 2004, provisional application No. 60/168,112, filed on Nov. 30, 1999.

(51) Int. Cl.
    *A61K 39/395* (2006.01)
(52) U.S. Cl. ............... 424/130.1; 424/133.1; 424/138.1; 424/141.1; 424/145.1; 424/158.1
(58) Field of Classification Search .................. None
    See application file for complete search history.

(56) References Cited

U.S. PATENT DOCUMENTS

| | | | |
|---|---|---|---|
| 4,868,116 | A | 9/1989 | Morgan et al. |
| 4,980,286 | A | 12/1990 | Morgan et al. |
| 5,096,815 | A | 3/1992 | Ladner et al. |
| 5,176,996 | A | 1/1993 | Hogan et al. |
| 5,198,346 | A | 3/1993 | Ladner et al. |
| 5,223,408 | A | 6/1993 | Goeddel et al. |
| 5,223,409 | A | 6/1993 | Ladner et al. |
| 5,256,775 | A | 10/1993 | Froehler |
| 5,264,564 | A | 11/1993 | Matteucci |
| 5,266,488 | A | 11/1993 | Ordahl et al. |
| 5,286,654 | A | 2/1994 | Cox et al. |
| 5,328,470 | A | 7/1994 | Nabel et al. |
| 2002/0015702 | A1* | 2/2002 | Burkly et al. ............. 424/142.1 |

FOREIGN PATENT DOCUMENTS

| | | |
|---|---|---|
| WO | WO 88/06630 | 9/1988 |
| WO | WO 89/02468 | 3/1989 |
| WO | WO 89/05345 | 6/1989 |
| WO | WO 89/07136 | 8/1989 |
| WO | WO 90/02809 | 3/1990 |
| WO | WO 92/07573 | 5/1992 |
| WO | WO 92/09690 | 6/1992 |
| WO | WO 92/15679 | 9/1992 |
| WO | WO 93/09222 | 5/1993 |
| WO | WO 93/25234 | 12/1993 |
| WO | WO 95/18856 | 7/1995 |
| WO | WO 95/31560 | 11/1995 |
| WO | WO 96/17924 | 6/1996 |
| WO | WO 96/29411 | 9/1996 |
| WO | WO 98/30520 A2 | 8/1998 |
| WO | WO-00/25725 | 5/2000 |
| WO | WO 00/74706 A1 | 12/2000 |
| WO | WO 02/080952 A2 | 10/2002 |

OTHER PUBLICATIONS

Scarpace et al. (1996). Eur. J. physiol. 431, 388-394.*
Stewart et al (2002). J. immunology. 169, 5451-5457.*
Chang et al. (1984). Eur Journal pharmacol. 101, Abstract only.*
Williams, et al., "Functional antagonists of sonic hedgehog reveal the importance of the N terminus for activity," Journal of Cell Science, 112:22,4405-4414, (1999).
El Andaloussi et al., "Hedgehog signaling controls thymocyte progenitor homeostasis and differentiation in the thymus," Nature Immunology, 7:4 418-426, (2006).
Outram et al., "Hedgehog signaling regulates differentiation from double-negative to double-positive thymocyte," Immunity, 13:2 187-197 (2000).
Razvi, "The Current Status of High-Throughput Screening and Outlook for the Future, Part I," Drug & Market Development, vol. 9, No. 4, pp. 89-104 (Apr. 3, 1998).
Reidhaar-Olson et al., "Combinatorial Cassette Mutagenesis as a Probe of the Informational Content of Protein Sequences," Science, vol. 241, pp. 53-57 (Jul. 1, 1988).
Arenas et al., "High throughput identification of specific small molecule ligands of therapeutic RNA targets from a diverse collection of small molecules," Nucleic Acid Symposium Series No. 41, pp. 13-16 (1990).
Wechsler-Reya et al., "Control of Neuronal Precursor Proliferation in the Cerebellum by Sonic Hedgehog," Neuron, vol. 22, pp. 103-114 (Jan. 1990).
Shah, D. et al. "Reduced Thymocyte Development in Sonic Hedgehog Knockout Embryos," The Journal of Immunology, pp. 2296-2306 (2004).
Lin, et al., "Increased cAMP and cAMP-Dependent Protein Kinase Activity Mediate Anti-CD2 Induced Suppression of Anti-CD3-Driven Interleukin-2 Production and CD25 Expression," Pathobiol. 63:175-187 (1995).
Bowie et al. 1990, Science 247:1306-1310.
Alexander et al., Proc. Natl. Acad. Sci. 89:3352-3356 (1992).
Lahana, Drug Discovery Today, 4(10:447-448 (1999).
Horrobin, DF, British Med. Journal 322(7280)239, Jul. 2003.
Stull and Lacovitti, Experimental Neurobiology 169(1)36-43 (2001).
Lowery et al., J. Immunology 169(4) 1869-1875 (1999).
Bubec et al., Alcohol 13(6)55-537 (1996).
Bryde et al., Immunopharmacology 41:139-146 (1999).
Shah et al., "Reduced Thymocyte Development in Sonic Hedgehog Knockout Embryos," The Journal of Immunology 172:2296-2306 (2004).

(Continued)

*Primary Examiner* — Jeffrey Stucker
*Assistant Examiner* — Stephen Gucker
(74) *Attorney, Agent, or Firm* — Ropes & Gray LLP

(57) ABSTRACT

The present application is directed to the discovery that hedgehog gene products, and signal transduction pathways involving hedgehog, are involved in maturation of T lymphocytes. The invention provides a method to promote T lymphocyte development using low dose Hedgehog, and a method to inhibit T lymphocyte development using high dose Hedgehog. Certain aspects of the invention are directed to preparations of hedgehog polypeptides, agonists, antagonists, or other molecules which regulate patched or smoothened signalling, and their uses as immunomodulatory agents.

6 Claims, 20 Drawing Sheets

OTHER PUBLICATIONS

Arkin and Yourvan, 1992, "An algorithm for protein engineering: simulations of recursive ensemble mutagenesis", Proc. Natl. Acad. Sci. USA 89:7811-7815.
Armentano et al., 1990, "Expression of human factor IX in rabbit hepatocytes by retrovirus-mediated gene transfer: potential for gene therapy of hemophilia B", Proc. Natl. Acad. Sci. USA 87:6141-6145.
Baldwin et al., 1984, "Cloning of the luciferase structural genes from Vibrio harveyi and expression of bioluminescence in *Escherichia coli*", Biochemistry 23:3663-3667.
Barbas et al., 1992, "Semisynthetic combinatorial antibody libraries: a chemical solution to the diversity problem", Proc. Natl. Acad. Sci. USA 89:4457-4461.
Bass et al., 1990, "Hormone phage: an enrichment method for variant proteins with altered binding properties", Proteins 8:309-314.
Bear et al., 1992, "Purification and functional reconstitution of the cystic fibrosis transmembrane conductance regulator (CFTR)", Cell 68:809-818.
Ben-Bassat et al., 1987, "Processing of the initiation methionine from proteins: properties of the *Escherichia coli* methionine aminopeptidase and its gene structure", J. Bacteriol. 169:751-757.
Benoist et al., 1981, "In vivo sequence requirements of the SV40 early promotor region", Nature 290:304-310.
Berkner et al., 1988, "Development of adenovirus vectors for the expression of heterologous genes", Biotechniques 6:616-629.
Borle, 1990, "An overview of techniques for the measurement of calcium distribution, calcium fluxes, and cytosolic free calcium in mammalian cells", Environ. Health Perspect. 84:45-56.
Bumcrot et al., 1995, "Proteolytic processing yields two secreted forms of sonic hedgehog", Mol. Cell. Biol. 15:2294-2303.
Chang et al., 1994, "Products, genetic linkage and limb patterning activity of a murine hedgehog gene", Development 120:3339-3353.
Chen et al., "Gene therapy for brain tumors: regression of experimental gliomas by adenovirus-mediated gene transfer in vivo", Proc. Natl. Acad. Sci. USA 91:3054-3057, Apr. 1994.
Chowdhury et al. 1991, "Long-term improvement of hypercholesterolemia after ex vivo gene therapy in LDLR-deficient rabbits", Science 254:1802-1805.
Clackson et al., 1991, "Making antibody fragments using phage display libraries", Nature 352:624-628.
Cullen and Malim, 1992, "Secreted placental alkaline phosphatase as a eukaryotic reporter gene", Methods Enzymol. 216:362-368.
Cwirla et al., 1990, "Peptides on phage: a vast library of peptides for identifying ligands", Proc. Natl. Acad. Sci. USA 87:6378-6382.
Dai et al., 1992, "Gene therapy via primary myoblasts: long-term expression of factor IX protein following transplantation in vivo", Proc. Natl. Acad. Sci. USA 89:10892-10895.
Dann et al., 1986, "Human renin: a new class of inhibitors", Biochem. Biophys. Res. Commun. 134:71-77.
Danos and Mulligan, 1988, "Safe and efficient generation of recombinant retroviruses with amphotropic and ecotropic host ranges", Proc. Natl. Acad. Sci. USA 85:6460-6464.
Delagrave et al., 1993, "Recursive ensemble mutagenesis", Protein Eng. 6:327-331.
Dev et al., 1994, Electrochemotherapy—a novel method of cancer treatment, Cancer Treat. Rev. 20:105-115.
Devlin et al., 1990, "Random peptide libraries: a source of specific protein binding molecules", Science 249:404-406.
DeWet et al., 1987, "Firefly luciferase gene: structure and expression in mammalian cells", Mol. Cell Biol. 7:725-737.
Eglitis et al., 1985, "Gene expression in mice after high efficiency retroviral-mediated gene transfer", Science 230:1395-1398.
Ekker et al., 1995, "Patterning activities of vertebrate hedgehog proteins in the developing eye and brain", Curr. Biol. 5:944-955.
Ellison et al., 1991, "Epitope-tagged ubiquitin. A new probe for analyzing ubiquitin function", J. Biol. Chem. 266:21150-21157.
Ellman et al., 1958, "A colorimetric method for determining low concentrations of mercaptans", Arch. Biochem. Biophys. 74:443.
Engebrecht and Silverman, 1984, "Identification of genes and gene products necessary for bacterial bioluminescence", Proc. Natl. Acad. Sci. USA 81:4154-4158.
Ettienne-Julan et al., 1992, "The efficiency of cell targeting by recombinant retroviruses depends on the nature of the receptor and the composition of the artificial cell-virus linker", J. Gen. Virol. 73 (Pt 12):3251-3255.
Ewenson et al., 1986, "Ketomethylene pseudopeptide analogues of substance P: synthesis and biological activity", J. Med. Chem. 29:295-299.
Ferry et al., 1991, "Retroviral-mediated gene transfer into hepatocytes in vivo", Proc. Natl. Acad. Sci. USA 88:8377-8381.
Fuchs et al., 1991, "Targeting recombinant antibodies to the surface of *Escherichia coli*: fusion to a petidoglycan associated lipoprotein", Bio/Technology 9:1370-1371.
Gallop et al., 1994, "Applications of combinatorial technologies to drug discovery. 1. Background and peptide combinatorial libraries", J. Med. Chem. 37:1233-1251.
Gordon et al., 1985, "Design of peptide derived amino alcohols as transition-state analog inhibitors of angiotensin converting enzyme", Biochem. Biophys. Res. Commun. 126:419-426.
Goud et al., 1983, "Antibody-mediated binding of a murine ecotropic Moloney retroviral vector to human cells allows internalization but not the establishment of the proviral state", Virology 163:251-254.
Goward et al, 1992, "Molecular evolution of bacterial cell-surface proteins", Trends Biochem. Sci. 18:136-140 Review.
Graham et al., 1991, "Manipulation of adenovirus vectors"*Methods in Molecular Biology* (Humana, Clifton, NJ) vol. 7 pp. 109-127.
Griffiths et al., 1993, "Human anti-self antibodies with high specificity from phage display libraries", EMBO J. 12:725-734.
Gunning et al., 1997, "A human beta-actin expression vector system directs high-level accumulation of antisense transcripts", Proc. Natl. Acad. Sci. USA 84:4831-4835.
Gustin et al., 1993, "Characterization of the role of individual protein binding motifs within the hepatitis B virus enhancer I on X promoter activity using linker scanning mutagenesis", Virology 193:653-660.
Habig et al., 1974, "Glutathione S-transferases. The first enzymatic step in mercapturic acid formation", J. Biol. Chem. 249:7130-7139.
Hahn et al., 1996, "Mutations of the human homolog of *Drosophila* patched in the nevoid basal cell carcinoma syndrome", Cell 85:841-851.
Haj-Ahmad et al., 1986, "Development of a helper-independent human adenovirus vector and its use in the transfer of the herpes simplex virus thymidine kinase gene", J. Virol. 57:267-274.
Hall et al., 1983, "Expression and regulation of *Escherichia coli* lacZ gene fusions in mammalian cells", J. Mol. Appl. Genet. 2:101-109.
Hammerschmidt et al., 1996, "Protein kinase A is a common negative regulator of Hedgehog signaling in the vertebrate embryo", Genes Dev. 10:647-658.
Hidalgo and Ingham, 1990, "Cell patterning in the *Drosophila* segment: spatial regulation of the segment polarity gene patched", Development 110:291-301.
Hochuli et al., 1987, "New metal chelate adsorbent selective for proteins and peptides containing neighbouring histidine residues", J. Chromatogr. 411:177-184.
Huber et al., 1991, "Retroviral-mediated gene therapy for the treatment of hepatocellular carcinoma: an innovative approach for cancer therapy", Proc. Natl. Acad. Sci. USA 88:8039-8043.
Hui et al., 1994, Expression of three mouse homologs of the *Drosophila* segment polarity gene cubitus interruptus, Gli, Gli-2, and Gli-3, in ectoderm- and mesoderm-derived tissues suggests multiple roles during postimplantation development, Dev. Biol. 162:402-413.
Huston et al., 1988, "Protein engineering of antibody binding sites: recovery of specific activity in an anti-digoxin single-chain Fv analogue produced in *Escherichia coli*", Proc. Natl. Acad. Sci. USA 85:5879-5883.
Hwu et al., 1993, "Functional and molecular characterization of tumor-infiltrating lymphocytes transduced with tumor necrosis factor-alpha cDNA for the gene therapy of cancer in humans", J. Immunol. 150:4104-4115.
Hynes, 1987, "Integrins: a family of cell surface receptors", Cell 48:549-554.
Hynes, 1992, "Integrins: versatility, modulation, and signaling in cell adhesion", Cell 69:11-25.
Ike et al., 1983, "Solid phase synthesis of polynucleotides. VIII. Synthesis of mixed oligodeoxyribonucleotides by the phosphotriester solid phase method", Nucleic Acids Res. 11:477-488.

Itakura et al., 1981, Recombinant DNA, Proc. 3rd Cleveland Symposium on Macromolecules, A.G. Walton, ed. (Elsevier, Amsterdam) pp. 273-289.
Itakura et al., 1984, "Expression in *Escherichia coli* of a chemically synthesized gene for the hormone somatostatin", Science 198:1056-1063.
Itakura et al., 1984, "Synthesis and use of synthetic oligonucleotides", Annu. Rev. Biochem. 53:323-356.
Johnson et al., 1996, "Human homolog of patched, a candidate gene for the basal cell nevus syndrome", Science 272:1668-1671.
Jones et al., 1979, "Isolation of adenovirus type 5 host range deletion mutants defective for transformation of rat embryo cells", Cell 17:683-689.
Karasuyama et al., 1989, "Autocrine growth and tumorigenicity of interleukin 2-dependent helper T cells with IL-2 gene", J. Exp. Med. 169:13-25.
Kay et al., 1992, "Hepatic gene therapy: persistent expression of human alpha 1-antitrypsin in mice after direct gene delivery in vivo", Hum. Gene Ther. 3:641-647.
Kinzler et al., 1990, "The GLI gene encodes a nuclear protein which binds specific sequences in the human genome", Mol. Cell. Biol. 10:634-642.
Klessig et al., 1984, "Introduction, stable integration, and controlled expression of a chimeric adenovirus gene whose product is toxic to the recipient human cell", Mol. Cell. Biol. 4:1354-1362.
Kornblihtt et al., 1985, "Primary structure of human fibronectin: differential splicing may generate at least 10 polypeptides from a single gene", EMBO J. 4:1755-1759.
Kube et al., 1995, "Isolation of the human interleukin 10 promoter. Characterization of the promoter activity in Burkitt's lymphoma cell lines", Cytokine 7:1-7.
Lai et al., 1995, "Patterning of the neural ectoderm of *Xenopus laevis* by the amino-terminal product of hedgehog autoproteolytic cleavage", Development 121:2349-2360.
Lee et al., 1992, "Secretion and localized transcription suggest a role in positional signaling for products of the segmentation gene hedgehog", Cell 71:33-50.
Lee et al., 1994, "Autoproteolysis in hedgehog protein biogenesis", Science 266:1528-1537.
Lyons and Nelson, 1984, "An immunological method for detecting gene expression in yeast colonies", Proc. Natl. Acad. Sci. USA 81:7426-7430.
Marigo and Tabin, 1996, "Regulation of patched by sonic hedgehog in the developing neural tube", Proc. Natl. Acad. Sci. USA 93:9346-9351.
Marigo et al., 1996, "Conservation in hedgehog signaling: induction of a chicken patched homolog by Sonic hedgehog in the developing limb", Development 122:1225-1233.
Marks et al., 1992, "Molecular evolution of proteins on filamentous phage. Mimicking the strategy of the immune system", J. Biol. Chem. 267:16007-16010.
Marti et al., 1995, "Distribution of Sonic hedgehog peptides in the developing chick and mouse embryo", Development 121:2537-2547.
Miller et al., 1987, "N-terminal methionine-specific peptidase in *Salmonella typhimurium*", Proc. Natl. Acad. Sci. USA 84:2718-2722.
Miller, 1990, "Progress toward human gene therapy", Blood 76:271-278.
Narang, 1983, "DNA synthesis", Tetrahedron 39:3-22.
Neda et al., 1991, "Chemical modification of an ecotropic murine leukemia virus results in redirection of its target cell specificity", J. Biol. Chem. 266:14143-14146.
Newton et al., 1983, "Transfer of band 3, the erythrocyte anion transporter, between phospholipid vesicles and cells", Biochemistry 22:6110-6117.
Orenic et al., 1996, "Cloning and characterization of the segment polarity gene cubitus interruptus Dominant of *Drosophila*", Genes Dev. 4:1053-1067.
Partis et al., 1983, "Cross-linking of protein by }T-maleimido alkanoyl n-hydroxysuccinimido esters", J. Pro. Chem. 2:263.
Pepinsky et al., 1998, "Identification of a palmitic acid-modified form of human Sonic hedgehog", J. Biol. Chem. 273:14037-14045.
Pierschbacher et al., 1984, "Cell attachment activity of fibronectin can be duplicated by small synthetic fragments of the molecule", Nature 309:30-33.
Pierschbacher et al., 1987, "Influence of stereochemistry of the sequence Arg-Gly-Asp-Xaa on binding specificity in cell adhesion", J. Biol. Chem. 262:17294-17298.
Porter et al., 1995, "The product of hedgehog autoproteolytic cleavage active in local and long-range signalling", Nature 374:363-366.
Porter et al., 1996, "Hedgehog patterning activity: role of a lipophilic modification mediated by the carboxy-terminal autoprocessing domain", Cell 86:21-34.
Preat et al., 1990, "A putative serine/threonine protein kinase encoded by the segment-polarity fused gene of *Drosophila*", Nature 347:87-89.
Reber et al., 1987, "Hydrophobic properties of the beta 1 and beta 2 subunits of the rat brain sodium channel", J. Biol. Chem. 262:11369-11374.
Riddles et al., 1979, "Ellman's reagent: 5,5'-dithiobis(2-nitrobenzoic acid)—a reexamination", Anal. Biochem. 94:75-81.
Roberts et al., 1992, "Directed evolution of a protein: selection of potent neutrophil elastase inhibitors displayed on M13 fusion phage", Proc. Natl. Acad. Sci. USA 89:2429-2433.
Roelink et al., 1995, "Floor plate and motor neuron induction by different concentrations of the amino-terminal cleavage product of sonic hedgehog autoproteolysis", Cell 81:445-455.
Roman et al., 1994, "Mapping of Hsp70-binding sites on protein antigens", Eur. J. Biochem. 222:65-73.
Rosenfeld et al., 1991, "Adenovirus-mediated transfer of a recombinant alpha 1-antitrypsin gene to the lung epithelium in vivo", Science 252:431-434.
Rosenfeld et al., 1992, "In vivo transfer of the human cystic fibrosis transmembrane conductance regulator gene to the airway epithelium", Cell 68:143-155.
Roux et al., 1989, "A versatile and potentially general approach to the targeting of specific cell types by retroviruses: application to the infection of human cells by means of major histocompatibility complex class I and class II antigens by mouse ecotropic murine leukemia virus-derived viruses", Proc. Natl. Acad. Sci. USA ;86:9079-9083.
Ruoslahti et al., 1987, "New perspectives in cell adhesion: RGD and integrins", Science 238:491-497.
Sato et al., 1986, "Synthesis and antibiotic activity of a gramicidin s analogue containing bicyclic beta-turn dipeptides", J. Chem. Soc. Perkin Trans. 1:1231.
Sato et al., 1995, "Structure and regulation of the gene encoding the neuron-specific protein kinase C substrate neurogranin (RC3 protein)", J. Biol. Chem. 270:10314-10322.
Scott et al., 1990, "Searching for peptide ligands with an epitope library", Science 249:386-390.
Sprague et al., 1983, "Expression of a recombinant DNA gene coding for the vesicular stomatitis virus nucleocapsid protein", J. Virol. 45:773-781.
Stein et al., 1988, Oligodeoxynucleotides as inhibitors of gene expression: a review, Cancer Res. 48:2659-2668 Review.
Tabata et al., 1992, "The *Drosophila* hedgehog gene is expressed specifically in posterior compartment cells and is a target of engrailed regulation", Genes Dev. 6:2635-2645.
Templeton et al., 1984, N-terminal amino acid sequences of the polyoma middle-size T antigen are important for protein kinase activity and cell transformation, Mol. Cell. Biol. 4:817-821.
Therond et al., 1993, "Molecular organisation and expression pattern of the segment polarity gene fused of *Drosophila melanogaster*", Mech. Dev. 44:65-80.
Toh et al., 1989, "Isolation and characterization of a rat liver alkaline phosphatase gene. A single gene with two promoters", Eur. J. Biochem. 182:231-237.
Van Beusechem et al., 1992, "Long-term expression of human adenosine deaminase in rhesus monkeys transplanted with retrovirus-infected bone-marrow cells", Proc. Natl. Acad. Sci. USA 89:7640-7644.
Van der Krol et al., 1988, "Modulation of eukaryotic gene expression by complementary RNA or DNA sequences", Biotechniques 6:958-976.

Wen et al., 1995, The expression and intracellular distribution of the heat-stable protein kinase inhibitor is cell cycle regulated, J. Biol. Chem. 270:2041-2046.

Wilson et al., 1988, "Retrovirus-mediated transduction of adult hepatocytes", Proc. Natl. Acad. Sci. USA 85:3014-3018.

Wolfe et al., 1992, "Herpesvirus vector gene transfer and expression of beta-glucuronidase in the central nervous system of MPS VII mice", Nat. Genet. 1:379-384.

Yamada et al., 1985, "Overproduction of the protein product of a nonselected foreign gene carried by an adenovirus vector", Proc. Natl. Acad. Sci. USA 82:3567-3571.

Yamamoto et al., 1980, "Identification of a functional promoter in the long terminal repeat of Rous sarcoma virus", Cell 22:787-797.

Youvan et al., 1992, *Parallel Problem Solving from Nature* (Elsevir Publishing Co., Amsterdam) pp. 401-410.

* cited by examiner

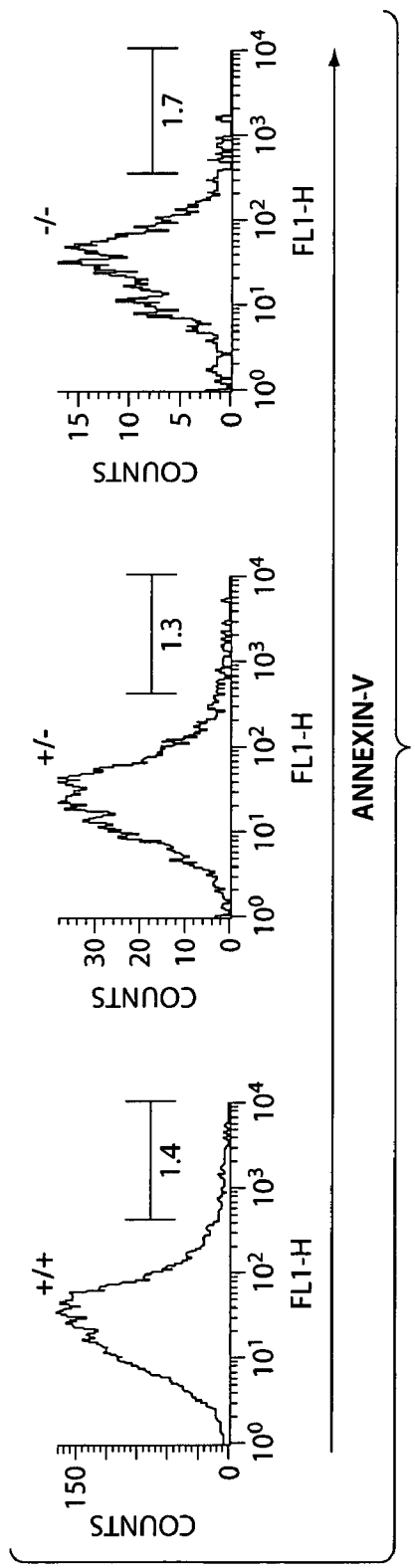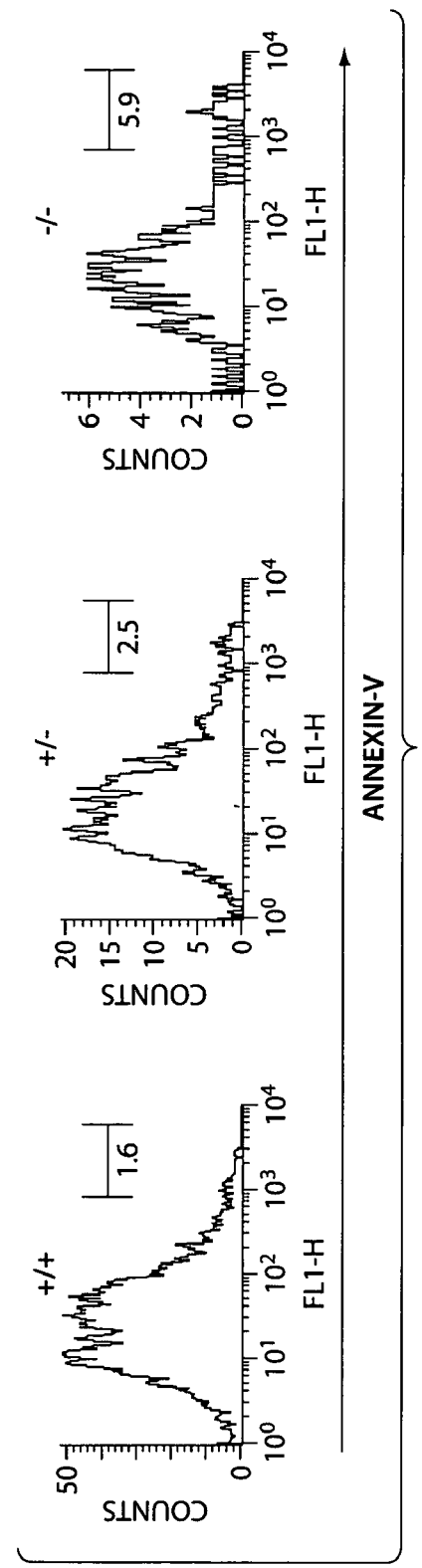

SEQUENCE LISTING

<160> NUMBER OF SEQ ID NOS: 31

<210> SEQ ID NO 1
<211> LENGTH: 1277
<212> TYPE: DNA
<213> ORGANISM: Gallus gallus

<400> SEQUENCE: 1
atggtcgaaa tgctgctgtt gacaagaatt ctcttggtgg gcttcatctg cgctctttta      60
gtctcctctg ggctgacttg tggaccaggc aggggcattg gaaaaggag gcaccccaaa     120

```
aagctgaccc cgttagccta taagcagttt attcccaatg tggcagagaa gaccctaggg      180
gccagtggaa gatatgaagg gaagatcaca agaaactccg agagatttaa agaactaacc      240
ccaaattaca accctgacat tatttttaag gatgaagaga acacgggagc tgacagactg      300
atgactcagc gctgcaagga caagctgaat gccctggcga tctcggtgat gaaccagtgg      360
cccggggtga agctgcgggt gaccgagggc tgggacgagg atggccatca ctccgaggaa      420
tcgctgcact acgagggtcg cgccgtggac atcaccacgt cggatcggga ccgcagcaag      480
tacggaatgc tggcccgcct cgccgtcgag gccggcttcg actgggtcta ctacgagtcc      540
aaggcgcaca tccactgctc cgtcaaagca gaaaactcag tggcagcgaa atcaggaggc      600
tgcttccctg gctcagccac agtgcacctg gagcatggag gcaccaagct ggtgaaggac      660
ctgagccctg ggaccgcgt gctggctgct gacgcggacg gccggctgct ctacagtgac      720
ttcctcacct cctcgaccg gatggacagc tcccgaaagc tcttctacgt catcgagacg      780
cggcagcccc gggcccggct gctactgacg gcggcccacc tgctctttgt ggcccccag     840 cacaaccagt cggaggccac agggtccacc agtggccagg cgctcttcgc cagcaacgtg      900
aagcctggcc aacgtgtcta tgtgctgggc gagggcgggc agcagctgct gccggcgtct      960
gtccacagcg tctcattgcg ggaggaggcg tccggagcct acgccccact caccgcccag     1020
ggcaccatcc tcatcaaccg ggtgttggcc tcctgctacg ccgtcatcga ggagcacagt     1080
tgggcccatt gggccttcgc accattccgc ttggctcagg gctgctggc cgccctctgc     1140 ccagatgggg ccatccctac tgccgccacc accaccactg gcatccattg gtactcacgg     1200
ctcctctacc gcatcggcag ctgggtgctg gatggtgacg cgctgcatcc gctgggcatg     1260
gtggcaccgg ccagctg                                                    1277

<210> SEQ ID NO 2
<211> LENGTH: 1190
<212> TYPE: DNA
<213> ORGANISM: Mus musculus

<400> SEQUENCE: 2
atggctctgc cggccagtct gttgcccctg tgctgcttgg cactcttggc actatctgcc       60
cagagctgcg ggccgggccg aggaccggtt ggccggcggc gttatgtgcg caagcaactt      120
gtgcctctgc tatacaagca gtttgtgccc agtatgcccg agcggaccct gggcgcgagt      180
gggccagcgg aggggagggt aacaaggggg tcggagcgct ccggacct cgtacccaac      240 tacaaccccg acataatctt caaggatgag agaacagcg gcgcagaccg cctgatgaca      300
gagcgttgca aagagcgggt gaacgctcta gccatcgcgg tgatgaacat gtggcccgga      360
gtacgcctac gtgtgactga aggctgggac gaggacggcc accacgcaca ggattcactc      420
cactacgaag gccgtgcctt ggacatcacc acgtctgacc gtgaccgtaa taagtatggt      480
ttgttggcgc gcctagctgt ggaagccgga ttcgactggg tctactacga gtcccgcaac      540
cacatccacg tatcggtcaa agctgataac tcactggcgg tccgagccgg aggctgcttt      600
ccgggaaatg ccacggtgcg cttgcgggagc ggcgaacgga aggggctgag gaactacat      660 cgtggtgact gggtactggc cgctgatgca gcgggccgag tggtacccac gccagtgctg      720
ctcttcctgg accgggatct gcagcgccgc gcctcgttcg tggctgtgga gaccgagcgg      780
cctccgcgca aactgttgct cacaccctgg catctggtgt tcgctgctcg cgggccagcg      840
cctgctccag gtgactttgc accggtgttc gcgcgccgct acgtgctgg cgactcggtg      900 ctggctcccg gcggggacgc gctccagccg gcgcgcgtag cccgcgtggc gcgcgaggaa      960
```

```
gccgtgggcg tgttcgcacc gctcactgcg cacgggacgc tgctggtcaa cgacgtcctc   1020
gcctcctgct acgcggttct agagagtcac cagtgggccc accgcgcctt cgccccttttg  1080 cggctgctgc acgcgctcgg ggctctgctc cctgggggtg cagtccagcc gactggcatg   1140
cattggtact ctcgcctcct ttaccgcttg gccgaggagt taatgggctg              1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt   60
ctggtgccgg cggcgcgggg ctgcgggccg gccgggtgg tgggcagccg ccggaggccg     120
cctcgcaagc tcgtgcctct tgcctacaag cagttcagcc caacgtgcc ggagaagacc    180 ctgggcgcca gcgggcgcta cgaaggcaag atcgcgcgca gctctgagcg cttcaaagag   240
ctcaccccca actacaatcc cgacatcatc ttcaaggacg aggagaacac gggtgccgac   300
cgcctcatga cccagcgctg caaggaccgt ctgaactcac tggccatctc tgtcatgaac   360
cagtggcctg gtgtgaaact gcgggtgacc gaaggccggg atgaagatgg ccatcactca   420
gaggagtctt tacactatga gggccgcgcg gtggatatca ccacctcaga ccgtgaccga   480
aataagtatg gactgctggc gcgcttagca gtggaggccg gcttcgactg ggtgtattac   540
gagtccaagg cccacgtgca ttgctctgtc aagtctgagc attcggccgc tgccaagaca   600
ggtggctgct ttcctgccgg agcccaggtg cgcctagaga acggggagcg tgtggccctg   660
tcagctgtaa agccaggaga ccgggtgctg gccatggggg aggatgggac ccccaccttc   720
agtgatgtgc ttatttttcct ggaccgcgag ccaaaccggc tgagagcttt ccaggtcatc   780
gagactcagg atcctccgcg tcggctggcg ctcacgcctg cccacctgct cttcattgcg   840
gacaatcata cagaaccagc agcccacttc cgggccacat ttgccagcca tgtgcaacca   900
ggccaatatg tgctggtatc aggggtacca ggcctccagc ctgctcgggt ggcagctgtc   960
tccacccacg tggcccttgg gtcctatgct cctctcacaa ggcatgggac acttgtggtg   1020
gaggatgtgg tggcctcctg ctttgcagct gtggctgacc accatctggc tcagttggcc   1080
ttctggcccc tgcgactgtt tcccagtttg gcatggggca gctggacccc aagtgagggt   1140
gttcactcct accctcagat gctctaccgc ctggggcgtc tcttgctaga agagagcacc   1200
ttccatccac tgggcatgtc tggggcagga agctgaaggg actctaacca ctgccctcct   1260
ggaactgctg tgcgtggatc c                                              1281
```

<210> SEQ ID NO 4
<211> LENGTH: 1313
<212> TYPE: DNA
<213> ORGANISM: Mus musculus

<400> SEQUENCE: 4

```
atgctgctgc tgctggccag atgttttctg gtgatccttg cttcctcgct gctggtgtgc   60
cccgggctgg cctgtgggcc cggcaggggg tttggaaaga ggcggcaccc caaaaagctg   120 accccttttag cctacaagca gtttattccc aacgtagccg agaagaccct aggggccagc    180
ggcagatatg aagggaagat cacaagaaac tccgaacgat taaggaactc accccccaat    240
tacaaccccg acatcatatt taaggatgag gaaaacacgg gagcagaccg gctgatgact   300
cagaggtgca agacaagtt aaatgccttg gccatctctg tgatgaacca gtggcctgga   360
```

```
gtgaggctgc gagtgaccga gggctgggat gaggacggcc atcattcaga ggagtctcta    420
cactatgagg gtcgagcagt ggacatcacc acgtccgacc gggaccgcag caagtacggc    480
atgctggctc gcctggctgt ggaagcaggt ttcgactggg tctactatga atccaaagct    540
cacatccact gttctgtgaa agcagagaac tccgtggcgg ccaaatccgg cggctgtttc    600
ccgggatccg ccaccgtgca cctggagcag ggcggcacca agctggtgaa ggacttacgt    660
cccggagacc gcgtgctggc ggctgacgac cagggccggc tgctgtacag cgacttcctc    720
accttcctgg accgcgacga aggcgccaag aaggtcttct acgtgatcga gacgctggag    780
ccgcgcgagc gcctgctgct caccgccgcg cacctgctct tcgtggcgcc gcacaacgac    840
tcggggccca cgcccgggcc aagcgcgctc tttgccagcc gcgtgcgccc cgggcagcgc    900
gtgtacgtgg tggctgaacg cggcggggac cgccggctgc tgcccgccgc ggtgcacagc    960
gtgacgctgc gagaggagga ggcgggcgcg tacgcgccgc tcacggcgca cggcaccatt   1020
ctcatcaacc gggtgctcgc ctcgtgctac gctgtcatcg aggagcacag ctgggcacac   1080
cgggccttcg cgccttttccg cctggcgcac gcgctgctgg ccgcgctggc acccgcccgc   1140
acggacggcg ggggcggggg cagcatccct gcagcgcaat ctgcaacgga agcgagggcc   1200
gcggagccga ctgcgggcat ccactggtac tcgcagctgc tctaccacat tggcacctgg   1260
ctgttggaca gcgagaccat gcatcccttg ggaatggcgg tcaagtccag ctg          1313

<210> SEQ ID NO 5
<211> LENGTH: 1256
<212> TYPE: DNA
<213> ORGANISM: Brachydanio rerio

<400> SEQUENCE: 5
atgcggcttt tgacgagagt gctgctggtg tctcttctca ctctgtcctt ggtggtgtcc     60
ggactggcct gcggtcctgg cagaggctac ggcagaagaa gacatccgaa gaagctgaca    120
cctctcgcct acaagcagtt catacctaat gtcgcggaga agaccttagg ggccagcggc    180
agatacgagg gcaagataac gcgcaattcg gagagattta agaacttac tccaaattac    240 aatcccgaca ttatctttaa ggatgaggag aacacgggag cggacaggct catgacacag    300
agatgcaaag acaagctgaa ctcgctggcc atctctgtaa tgaaccactg gccaggggtt    360
aagctgcgtg tgacagaggg ctgggatgag gacggtcacc attttgaaga atcactccac    420
tacgagggaa gagctgttga tattaccacc tctgaccgag acaagagcaa atacgggaca    480
ctgtctcgcc tagctgtgga ggctggattt gactgggtct attacgagtc caaagcccac    540
attcattgct ctgtcaaagc agaaaattcg gttgctgcga atctgggggg ctgtttccca    600
ggttcggctc tggtctcgct ccaggacgga ggacagaagg ccgtgaagga cctgaacccc    660
ggagacaagg tgctggcggc agacagcgcg ggaaacctgg tgttcagcga cttcatcatg    720
ttcacagacc gagactccac gacgcgacgt gtgttttacg tcatagaaac gcaagaaccc    780
gttgaaaaga tcaccctcac cgccgctcac ctccttttttg tcctcgacaa ctcaacggaa    840
gatctccaca ccatgaccgc cgcgtatgcc agcagtgtca gagccggaca aaaggtgatg    900
gttgttgatg atagcggtca gcttaaatct gtcatcgtgc agcggatata cacggaggag    960
cagcggggct cgttcgcacc agtgactgca catgggacca ttgtggtcga cagaatactg   1020
gcgtcctgtt acgccgtaat agaggaccag gggcttgcgc atttggcctt cgcgcccgcc   1080
aggctctatt attacgtgtc atcattcctg tcccccaaaa ctccagcagt cggtccaatg   1140
cgactttaca acaggagggg gtccactggt actccaggct cctgtcatca aatgggaacg   1200
```

```
tggcttttgg acagcaacat gcttcatcct ttggggatgt cagtaaactc aagctg      1256
```

<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387)..(1389)
<223> OTHER INFORMATION: a, c, g, t, unknown or other

<400> SEQUENCE: 6

```
atgctgctgc tggcgagatg tctgctgcta gtcctcgtct cctcgctgct ggtatgctcg       60
ggactggcgt gcggaccggg caggggggttc gggaagagga ggcaccccaa aaagctgacc     120
cctttagcct acaagcagtt tatccccaat gtggccgaga gaccctagg cgccagcgga      180
aggtatgaag ggaagatctc cagaaactcc gagcgattta aggaactcac ccccaattac     240
aaccccgaca tcatatttaa ggatgaagaa aacaccggag cggacaggct gatgactcag     300
aggtgtaagg acaagttgaa cgctttggcc atctcggtga tgaaccagtg gccaggagtg     360
aaactgcggg tgaccgaggg ctgggacgaa gatggccacc actcagagga gtctctgcac     420
tacgagggcc gcgcagtgga catcaccacg tctgaccgcg accgcagcaa gtacggcatg     480
ctggcccgcc tggcggtgga ggccggcttc gactgggtgt actacgagtc caaggcacat     540
atccactgct cggtgaaagc agagaactcg gtggcggcca atcgggagg ctgcttcccg      600
ggctcggcca cggtgcacct ggagcagggc ggcaccaagc tggtgaagga cctgagcccc     660
ggggaccgcg tgctggcggc ggacgaccag ggccggctgc tctacagcga cttcctcact     720
ttcctggacc gcgacgacgg cgccaagaag gtcttctacg tgatcgagac gcgggagccg     780
cgcgagcgcc tgctgctcac cgccgcgcac ctgctctttg tggcgccgca caacgactcg     840
gccaccgggg agcccgaggc gtcctcgggc tcggggccgc cttccggggg cgcactgggg     900
cctcgggcgc tgttcgccag ccgcgtgcgc ccggccagc gcgtgtacgt ggtggccgag      960
cgtgacgggg accgccggct cctgcccgcc gctgtgcaca gcgtgaccct aagcgaggag    1020
gccgcgggcg cctacgcgcc gctcacggcc cagggcacca ttctcatcaa ccgggtgctg    1080
gcctcgtgct acgcggtcat cgaggagcac agctgggcgc accgggcctt cgcgcccttc    1140
cgcctggcgc acgcgctcct ggctgcactg gcgcccgcgc gcacgaccg cggcggggac    1200
agcggcggcg ggaccgcgg gggcggcggc ggcagagtag ccctaaccgc tccaggtgct     1260
gccgacgctc cgggtgcggg ggccaccgcg ggcatccact ggtactcgca gctgctctac    1320
caaataggca cctggctcct ggacagcgag gccctgcacc cgctgggcat ggcggtcaag    1380
tccagcnnna gccgggggc cggggaggg gcgcgggagg gggcc                     1425
```

<210> SEQ ID NO 7
<211> LENGTH: 1622
<212> TYPE: DNA
<213> ORGANISM: Homo sapiens

<400> SEQUENCE: 7

```
catcagccca ccaggagacc tcgcccgccg ctcccccggg ctccccggcc atgtctcccg       60
ccccggctccg gccccgactg cacttctgcc tggtcctgtt gctgctgctg gtggtgcccc    120
cggcatgggg ctgcgggccg ggtcgggtgg tgggcagccg ccggcgaccg ccacgcaaac    180
tcgtgccgct cgcctacaag cagttcagcc ccaatgtgcc cgagaagacc ctgggcgcca    240
gcggacgcta tgaaggcaag atcgctcgca gctccgagcg cttcaaggag ctcacccccca    300
```

| | |
|---|---|
| attacaatcc agacatcatc ttcaaggacg aggagaacac aggcgccgac cgcctcatga | 360 |
| cccagcgctg caaggaccgc ctgaactcgc tggctatctc ggtgatgaac cagtggcccg | 420 |
| gtgtgaagct gcgggtgacc gagggctggg acgaggacgg ccaccactca gaggagtccc | 480 |
| tgcattatga gggccgcgcg gtggacatca ccacatcaga ccgcgaccgc aataagtatg | 540 |
| gactgctggc gcgcttggca gtggaggccg gctttgactg ggtgtattac gagtcaaagg | 600 |
| cccacgtgca ttgctccgtc aagtccgagc actcggccgc agccaagacg ggcggctgct | 660 |
| tccctgccgg agcccaggta cgcctggaga gtggggcgcg tgtggccttg tcagccgtga | 720 |
| ggccgggaga ccgtgtgctg gccatggggg aggatgggag ccccaccttc agcgatgtgc | 780 |
| tcattttcct ggaccgcgag ccccacaggc tgagagcctt ccaggtcatc gagactcagg | 840 |
| acccccacg ccgcctggca ctcacacccg ctcacctgct ctttacggct gacaatcaca | 900 |
| cggagccggc agcccgcttc cgggccacat tgccagcca cgtgcagcct ggccagtacg | 960 |
| tgctggtggc tggggtgcca ggcctgcagc ctgcccgcgt ggcagctgtc tctacacacg | 1020 |
| tggccctcgg ggcctacgcc cgctcacaa agcatgggac actggtggtg gaggatgtgg | 1080 |
| tggcatcctg cttcgcggcc gtggctgacc accacctggc tcagttggcc ttctggcccc | 1140 |
| tgagactctt tcacagcttg gcatggggca gctggacccc gggggagggt gtgcattggt | 1200 |
| accccccagct gctctaccgc ctggggcgtc tcctgctaga agagggcagc ttccacccac | 1260 |
| tgggcatgtc cggggcaggg agctgaaagg actccaccgc tgccctcctg gaactgctgt | 1320 |
| actgggtcca gaagcctctc agccaggagg gagctggccc tggaagggac ctgagctggg | 1380 |
| ggacactggc tcctgccatc tcctctgcca tgaagataca ccattgagac ttgactgggc | 1440 |
| aacaccagcg tcccccaccc cgtcgtggt gtagtcatag agctgcaagc tgagctggcg | 1500 |
| aggggatggt tgttgacccc tctctcctag agaccttgag gctggcacgg cgactcccaa | 1560 |
| ctcagcctgc tctcactacg agttttcata ctctgcctcc cccattggga gggcccattc | 1620 |
| cc | 1622 |

```
<210> SEQ ID NO 8
<211> LENGTH: 1191
<212> TYPE: DNA
<213> ORGANISM: Homo sapiens

<400> SEQUENCE: 8
```

| | |
|---|---|
| atggctctcc tgaccaatct actgcccttg tgctgcttgg cacttctggc gctgccagcc | 60 |
| cagagctgcg ggccgggccg ggggccggtt ggccggcgcc gctatgcgcg caagcagctc | 120 |
| gtgccgctac tctacaagca atttgtgccc ggcgtgccag agcggaccct gggcgccagt | 180 |
| gggccagcgg aggggagggt ggcaaggggc tccgagcgct tccgggacct cgtgcccaac | 240 |
| tacaaccccg acatcatctt caaggatgag gagaacagtg gagccgaccg cctgatgacc | 300 |
| gagcgttgca aggagagggt gaacgctttg gccattgccg tgatgaacat gtggcccgga | 360 |
| gtgcgcctac gagtgactga gggctggac gaggacggcc accacgctca ggattcactc | 420 |
| cactacgaag gccgtgcttt ggacatcact acgtctgacc gcgaccgcaa caagtatggg | 480 |
| ttgctggcgc gcctcgcagt ggaagccggc ttcgactggg tctactacga gtcccgcaac | 540 |
| cacgtccacg tgtcggtcaa agctgataac tcactggcgg tccgggcggg cggctgcttt | 600 |
| ccgggaaatg caactgtgcg cctgtggagc ggcgagcgga aagggctgcg ggaactgcac | 660 |
| cgcggagact gggttttggc ggccgatgcg tcaggccggg tggtgcccac gccggtgctg | 720 |
| ctcttcctgg accgggactt gcagcgccgg gcttcatttg tggctgtgga gaccgagtgg | 780 |

-continued

```
cctccacgca aactgttgct cacgccctgg cacctggtgt ttgccgctcg agggccggcg      840
cccgcgccag gcgactttgc accggtgttc gcgcgccggc tacgcgctgg ggactcggtg      900
ctggcgcccg gcggggatgc gcttcggcca gcgcgcgtgg cccgtgtggc gcggaggaa       960 gccgtgggcg tgttcgcgcc gctcaccgcg cacgggacgc tgctggtgaa cgatgtcctg     1020
gcctcttgct acgcggttct ggagagtcac cagtgggcgc accgcgcttt tgcccccttg     1080
agactgctgc acgcgctagg ggcgctgctc cccggcgggg ccgtccagcc gactggcatg     1140
cattggtact ctcggctcct ctaccgctta gcggaggagc tactgggctg a              1191
```

<210> SEQ ID NO 9
<211> LENGTH: 1251
<212> TYPE: DNA
<213> ORGANISM: Brachydanio rerio

<400> SEQUENCE: 9

```
atggacgtaa ggctgcatct gaagcaattt gctttactgt gttttatcag cttgcttctg       60
acgccttgtg gattagcctg tggtcctggt agaggttatg gaaaacgaag acacccaaag      120
aaattaaccc cgttggctta caagcaattc atccccaacg ttgctgagaa acgcttgga       180 gccagcggca aatacgaagg caaaatcaca aggaattcag agagatttaa agagctgatt      240
ccgaattata atcccgatat catctttaag gacgaggaaa cacaaacgc tgacaggctg       300 atgaccaagc gctgtaagga caagttaaat tcgttggcca tatccgtcat gaaccactgg      360 cccgcgtga aactgcgcgt cactgaaggc tgggatgagg atggtcacca tttagaagaa       420
tctttgcact atgagggacg ggcagtggac atcactacct cagacaggga taaaagcaag      480
tatgggatgc tatccaggct tgcagtggag gcaggattcg actgggtcta ttatgaatct      540
aaagcccaca tacactgctc tgtcaaagca gaaaattcag tggctgctaa atcaggagga      600
tgttttcctg gtctggggac ggtgacactt ggtgatggga cgaggaaacc catcaaagat      660
cttaaagtgg gcgaccgggt tttggctgca gacgagaagg gaaatgtctt aataagcgac      720
tttattatgt ttatagacca cgatccgaca acgagaaggc aattcatcgt catcgagacg      780 tcagaaccttt tcaccaagct caccctcact gccgcgcacc tagttttcgt tggaaactct      840
tcagcagctt cgggtataac agcaacattt gccagcaacg tgaagcctgg agatacagtt      900
ttagtgtggg aagacacatg cgagagcctc aagagcgtta cagtgaaaag gatttacact      960
gaggagcacg agggctcttt tgcgccagtc accgcgcacg gaaccataat agtggatcag     1020
gtgttggcat cgtgctacgc ggtcattgag aaccacaaat gggcacattg gcttttgcg     1080 ccggtcaggt tgtgtcacaa gctgatgacg tggcttttc cggctcgtga atcaaacgtc     1140
aattttcagg aggatggtat ccactggtac tcaaatatgc tgtttcacat cggctcttgg     1200
ctgctggaca gagactcttt ccatccactc gggattttac acttaagttg a             1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Leu Thr Arg Ile Leu Leu Val Gly Phe Ile
  1               5                  10                  15

Cys Ala Leu Leu Val Ser Ser Gly Leu Thr Cys Gly Pro Gly Arg Gly
             20                  25                  30

Ile Gly Lys Arg Arg His Pro Lys Lys Leu Thr Pro Leu Ala Tyr Lys
```

```
                35                  40                  45
Gln Phe Ile Pro Asn Val Ala Glu Lys Thr Leu Gly Ala Ser Gly Arg
 50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Glu Asn Thr Gly
                 85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
        275                 280                 285

Ser Thr Ser Gly Gln Ala Leu Phe Ala Ser Asn Val Lys Pro Gly Gln
290                 295                 300

Arg Val Tyr Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
        355                 360                 365

Phe Arg Leu Ala Gln Gly Leu Leu Ala Ala Leu Cys Pro Asp Gly Ala
370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

<210> SEQ ID NO 11
<211> LENGTH: 396
<212> TYPE: PRT
<213> ORGANISM: Mus musculus
```

<400> SEQUENCE: 11

```
Met Ala Leu Pro Ala Ser Leu Leu Pro Leu Cys Cys Leu Ala Leu Leu
 1               5                  10                  15

Ala Leu Ser Ala Gln Ser Cys Gly Pro Gly Arg Gly Pro Val Gly Arg
             20                  25                  30

Arg Arg Tyr Val Arg Lys Gln Leu Val Pro Leu Leu Tyr Lys Gln Phe
         35                  40                  45

Val Pro Ser Met Pro Glu Arg Thr Leu Gly Ala Ser Gly Pro Ala Glu
     50                  55                  60

Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
            355                 360                 365

Leu Leu Pro Gly Gly Ala Val Gln Pro Thr Gly Met His Trp Tyr Ser
        370                 375                 380

Arg Leu Leu Tyr Arg Leu Ala Glu Glu Leu Met Gly
385                 390                 395
```

<210> SEQ ID NO 12
<211> LENGTH: 411

<212> TYPE: PRT
<213> ORGANISM: Mus musculus

<400> SEQUENCE: 12

```
Met Ser Pro Ala Trp Leu Arg Pro Arg Leu Arg Phe Cys Leu Phe Leu
1               5                   10                  15

Leu Leu Leu Leu Leu Val Pro Ala Ala Arg Gly Cys Gly Pro Gly Arg
            20                  25                  30

Val Val Gly Ser Arg Arg Arg Pro Pro Arg Lys Leu Val Pro Leu Ala
        35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
    290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
    370                 375                 380

Pro Gln Met Leu Tyr Arg Leu Gly Arg Leu Leu Leu Glu Glu Ser Thr
385                 390                 395                 400
```

Phe His Pro Leu Gly Met Ser Gly Ala Gly Ser
           405                    410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
1                5                  10               15

Leu Leu Val Cys Pro Gly Leu Ala Cys Gly Pro Gly Arg Gly Phe Gly
          20                    25                    30

Lys Arg Arg His Pro Lys Lys Leu Thr Pro Leu Ala Tyr Lys Gln Phe
     35                    40                    45

Ile Pro Asn Val Ala Glu Lys Thr Leu Gly Ala Ser Gly Arg Tyr Glu
 50                    55                    60

Gly Lys Ile Thr Arg Asn Ser Glu Arg Phe Lys Glu Leu Thr Pro Asn
65                70                  75               80

Tyr Asn Pro Asp Ile Ile Phe Lys Asp Glu Glu Asn Thr Gly Ala Asp
          85                    90                    95

Arg Leu Met Thr Gln Arg Cys Lys Asp Lys Leu Asn Ala Leu Ala Ile
          100                   105                 110

Ser Val Met Asn Gln Trp Pro Gly Val Arg Leu Arg Val Thr Glu Gly
      115                  120                 125

Trp Asp Glu Asp Gly His His Ser Glu Glu Ser Leu His Tyr Glu Gly
 130                   135                 140

Arg Ala Val Asp Ile Thr Thr Ser Asp Arg Asp Arg Ser Lys Tyr Gly
145               150                  155             160

Met Leu Ala Arg Leu Ala Val Glu Ala Gly Phe Asp Trp Val Tyr Tyr
          165                   170                 175

Glu Ser Lys Ala His Ile His Cys Ser Val Lys Ala Glu Asn Ser Val
      180                  185                 190

Ala Ala Lys Ser Gly Gly Cys Phe Pro Gly Ser Ala Thr Val His Leu
 195                   200                 205

Glu Gln Gly Gly Thr Lys Leu Val Lys Asp Leu Arg Pro Gly Asp Arg
210               215                  220

Val Leu Ala Ala Asp Asp Gln Gly Arg Leu Leu Tyr Ser Asp Phe Leu
225               230                  235             240

Thr Phe Leu Asp Arg Asp Glu Gly Ala Lys Lys Val Phe Tyr Val Ile
          245                   250                 255

Glu Thr Leu Glu Pro Arg Glu Arg Leu Leu Leu Thr Ala Ala His Leu
      260                  265                 270

Leu Phe Val Ala Pro His Asn Asp Ser Gly Pro Thr Pro Gly Pro Ser
 275                   280                 285

Ala Leu Phe Ala Ser Arg Val Arg Pro Gly Gln Arg Val Tyr Val Val
290               295                  300

Ala Glu Arg Gly Gly Asp Arg Arg Leu Leu Pro Ala Ala Val His Ser
305               310                  315             320

Val Thr Leu Arg Glu Glu Glu Ala Gly Ala Tyr Ala Pro Leu Thr Ala
          325                   330                 335

His Gly Thr Ile Leu Ile Asn Arg Val Leu Ala Ser Cys Tyr Ala Val
      340                  345                 350

Ile Glu Glu His Ser Trp Ala His Arg Ala Phe Ala Pro Phe Arg Leu
 355                   360                 365

```
Ala His Ala Leu Leu Ala Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
            435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Leu Val Ser Leu Leu Thr Leu Ser
 1               5                  10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300
```

-continued

```
Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
            325                 330                 335

Asp Arg Ile Leu Ala Ser Cys Tyr Ala Val Ile Glu Asp Gln Gly Leu
        340                 345                 350

Ala His Leu Ala Phe Ala Pro Ala Arg Leu Tyr Tyr Tyr Val Ser Ser
    355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser
```

<210> SEQ ID NO 15
<211> LENGTH: 475
<212> TYPE: PRT
<213> ORGANISM: Homo sapiens
<220> FEATURE:
<221> NAME/KEY: MOD_RES
<222> LOCATION: (463)
<223> OTHER INFORMATION: Gly, Ala, Val, Leu, Ile, Thr, or Ser

<400> SEQUENCE: 15

```
Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240
```

```
Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser Xaa Ser
    450                 455                 460

Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
1               5                   10                  15

Leu Leu Leu Leu Val Val Pro Ala Ala Trp Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140
```

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
            165                 170                 175

Trp Val Tyr Tyr Glu Ser Lys Ala His Val His Cys Ser Val Lys Ser
        180                 185                 190

Glu His Ser Ala Ala Lys Thr Gly Gly Cys Phe Pro Ala Gly Ala
    195                 200                 205

Gln Val Arg Leu Glu Ser Gly Ala Arg Val Ala Leu Ser Ala Val Arg
210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
                260                 265                 270

Pro Ala His Leu Leu Phe Thr Ala Asp Asn His Thr Glu Pro Ala Ala
            275                 280                 285

Arg Phe Arg Ala Thr Phe Ala Ser His Val Gln Pro Gly Gln Tyr Val
290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
            405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

-continued

```
Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Ala Ser Phe Val Ala Val
                245                 250                 255

Glu Thr Glu Trp Pro Pro Arg Lys Leu Leu Thr Pro Trp His Leu
        260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
1               5                   10                  15

Ser Leu Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
        50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Asn
                85                  90                  95
```

```
Ala Asp Arg Leu Met Thr Lys Arg Cys Lys Asp Lys Leu Asn Ser Leu
            100                 105                 110
Ala Ile Ser Val Met Asn His Trp Pro Gly Val Lys Leu Arg Val Thr
        115                 120                 125
Glu Gly Trp Asp Glu Asp Gly His His Leu Glu Glu Ser Leu His Tyr
130                 135                 140
Glu Gly Arg Ala Val Asp Ile Thr Thr Ser Arg Asp Lys Ser Lys
145                 150                 155                 160
Tyr Gly Met Leu Ser Arg Leu Ala Val Glu Ala Gly Phe Asp Trp Val
                165                 170                 175
Tyr Tyr Glu Ser Lys Ala His Ile His Cys Ser Val Lys Ala Glu Asn
            180                 185                 190
Ser Val Ala Ala Lys Ser Gly Gly Cys Phe Pro Gly Ser Gly Thr Val
        195                 200                 205
Thr Leu Gly Asp Gly Thr Arg Lys Pro Ile Lys Asp Leu Lys Val Gly
210                 215                 220
Asp Arg Val Leu Ala Ala Asp Glu Lys Gly Asn Val Leu Ile Ser Asp
225                 230                 235                 240
Phe Ile Met Phe Ile Asp His Asp Pro Thr Thr Arg Arg Gln Phe Ile
                245                 250                 255
Val Ile Glu Thr Ser Glu Pro Phe Thr Lys Leu Thr Leu Thr Ala Ala
            260                 265                 270
His Leu Val Phe Val Gly Asn Ser Ala Ala Ser Gly Ile Thr Ala
        275                 280                 285
Thr Phe Ala Ser Asn Val Lys Pro Gly Asp Thr Val Leu Val Trp Glu
290                 295                 300
Asp Thr Cys Glu Ser Leu Lys Ser Val Thr Val Lys Arg Ile Tyr Thr
305                 310                 315                 320
Glu Glu His Glu Gly Ser Phe Ala Pro Val Thr Ala His Gly Thr Ile
                325                 330                 335
Ile Val Asp Gln Val Leu Ala Ser Cys Tyr Ala Val Ile Glu Asn His
            340                 345                 350
Lys Trp Ala His Trp Ala Phe Ala Pro Val Arg Leu Cys His Lys Leu
        355                 360                 365
Met Thr Trp Leu Phe Pro Ala Arg Glu Ser Asn Val Asn Phe Gln Glu
370                 375                 380
Asp Gly Ile His Trp Tyr Ser Asn Met Leu Phe His Ile Gly Ser Trp
385                 390                 395                 400
Leu Leu Asp Arg Asp Ser Phe His Pro Leu Gly Ile Leu His Leu Ser
                405                 410                 415

<210> SEQ ID NO 19
<211> LENGTH: 1416
<212> TYPE: DNA
<213> ORGANISM: Drosophila melanogaster
<220> FEATURE:
<221> NAME/KEY: CDS
<222> LOCATION: (1)..(1413)

<400> SEQUENCE: 19 atg gat aac cac agc tca gtg cct tgg gcc agt gcc gcc agt gtc acc    48
Met Asp Asn His Ser Ser Val Pro Trp Ala Ser Ala Ala Ser Val Thr
  1               5                  10                  15 tgt ctc tcc ctg gga tgc caa atg cca cag ttc cag ttc cag ttc cag    96
Cys Leu Ser Leu Gly Cys Gln Met Pro Gln Phe Gln Phe Gln Phe Gln
                 20                  25                  30 ctc caa atc cgc agc gag ctc cat ctc cgc aag ccc gca aga aga acg   144
```

-continued

```
                Leu Gln Ile Arg Ser Glu Leu His Leu Arg Lys Pro Ala Arg Arg Thr
                             35                  40                  45 caa acg atg cgc cac att gcg cat acg cag cgt tgc ctc agc agg ctg         192
Gln Thr Met Arg His Ile Ala His Thr Gln Arg Cys Leu Ser Arg Leu
 50                  55                  60 acc tct ctg gtg gcc ctg ctg atc gtc ttg ccg atg gtc ttt agc             240
Thr Ser Leu Val Ala Leu Leu Ile Val Leu Pro Met Val Phe Ser
 65                  70                  75                  80 ccg gct cac agc tgc ggt cct ggc cga gga ttg ggt cgt cat agg gcg         288
Pro Ala His Ser Cys Gly Pro Gly Arg Gly Leu Gly Arg His Arg Ala
                 85                  90                  95 cgc aac ctg tat ccg ctg gtc ctc aag cag aca att ccc aat cta tcc         336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg         384
Glu Tyr Thr Asn Ser Ala Ser Gly Pro Leu Glu Gly Val Ile Arg Arg
            115                 120                 125 gat tcg ccc aaa ttc aag gac ctc gtg ccc aac tac aac agg gac atc         432
Asp Ser Pro Lys Phe Lys Asp Leu Val Pro Asn Tyr Asn Arg Asp Ile
130                 135                 140 ctt ttc cgt gac gag gaa ggc acc gga gcg gat ggc ttg atg agc aag         480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa         528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac         576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att         624
His His Gly Gln Glu Ser Leu His Tyr Glu Gly Arg Ala Val Thr Ile
            195                 200                 205 gcc acc tcc gat cgc gac cag tcc aaa tac ggc atg ctc gct cgc ctg         672
Ala Thr Ser Asp Arg Asp Gln Ser Lys Tyr Gly Met Leu Ala Arg Leu
210                 215                 220 gcc gtc gag gct gga ttc gat tgg gtc tcc tac gtc agc agg cgc cac         720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac         768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg         816
Gly Cys Phe Thr Pro Glu Ser Thr Ala Leu Leu Glu Ser Gly Val Arg
            260                 265                 270 aag ccg ctc ggc gag ctc tct atc gga gat cgt gtt ttg agc atg acc         864
Lys Pro Leu Gly Glu Leu Ser Ile Gly Asp Arg Val Leu Ser Met Thr
            275                 280                 285 gcc aac gga cag gcc gtc tac agc gaa gtg atc ctc ttc atg gac cgc         912
Ala Asn Gly Gln Ala Val Tyr Ser Glu Val Ile Leu Phe Met Asp Arg
            290                 295                 300 aac ctc gag cag atg caa aac ttt gtg cag ctg cac acg gac ggt gga         960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg         1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag         1056
Glu Ser Gln Lys Leu Thr Phe Val Phe Ala His Arg Ile Glu Glu Lys
            340                 345                 350 aac cag gtg ctc gta cgg gat gtg gag acg ggc gag ctg agg ccc cag         1104
```

```
Asn Gln Val Leu Val Arg Asp Val Glu Thr Gly Glu Leu Arg Pro Gln
        355                 360                 365 cga gtg gtc aag ttg ggc agt gtg cgc agt aag ggc gtg gtc gcg ccg      1152
Arg Val Val Lys Leu Gly Ser Val Arg Ser Lys Gly Val Val Ala Pro
        370                 375                 380 ctg acc cgc gag ggc acc att gtg gtc aac tcg gtg gcc gcc agt tgc      1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc      1248
Tyr Ala Val Ile Asn Ser Gln Ser Leu Ala His Trp Gly Leu Ala Pro
                    405                 410                 415 atg cgc ctg ctg tcc acg ctg gag gcg tgg ctg ccc gcc aag gag cag      1296
Met Arg Leu Leu Ser Thr Leu Glu Ala Trp Leu Pro Ala Lys Glu Gln
                420                 425                 430 ttg cac agt tcg ccg aag gtg gtg agc tcg gcg cag cag cag aat ggc      1344
Leu His Ser Ser Pro Lys Val Val Ser Ser Ala Gln Gln Gln Asn Gly
            435                 440                 445 atc cat tgg tat gcc aat gcg ctc tac aag gtc aag gac tac gtg ctg      1392
Ile His Trp Tyr Ala Asn Ala Leu Tyr Lys Val Lys Asp Tyr Val Leu
450                 455                 460 ccg cag agc tgg cgc cac gat tga                                      1416
Pro Gln Ser Trp Arg His Asp
465                 470

<210> SEQ ID NO 20
<211> LENGTH: 471
<212> TYPE: PRT
<213> ORGANISM: Drosophila melanogaster

<400> SEQUENCE: 20

Met Asp Asn His Ser Ser Val Pro Trp Ala Ser Ala Ser Val Thr
1               5                   10                  15

Cys Leu Ser Leu Gly Cys Gln Met Pro Gln Phe Gln Phe Gln Phe Gln
            20                  25                  30

Leu Gln Ile Arg Ser Glu Leu His Leu Arg Lys Pro Ala Arg Arg Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
    130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220
```

```
Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
    290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
                340                 345                 350

Asn Gln Val Leu Val Arg Asp Val Glu Thr Gly Glu Leu Arg Pro Gln
            355                 360                 365

Arg Val Val Lys Leu Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ala Gln Gln Gln Asn Gly
            435                 440                 445

Ile His Trp Tyr Ala Asn Ala Leu Tyr Lys Val Lys Asp Tyr Val Leu
        450                 455                 460

Pro Gln Ser Trp Arg His Asp
465                 470

<210> SEQ ID NO 21
<211> LENGTH: 221
<212> TYPE: PRT
<213> ORGANISM: Artificial Sequence
<220> FEATURE:
<223> OTHER INFORMATION: Description of Artificial Sequence: Synthetic
      degenerate Shh polypeptide general formula
<220> FEATURE:
<221> NAME/KEY: MOD_RES
<222> LOCATION: (7)
<223> OTHER INFORMATION: any amino acid, preferably Gly, Ala, Val, Leu,
      Ile, Phe, Tyr or Trp
<220> FEATURE:
<221> NAME/KEY: MOD_RES
<222> LOCATION: (9)
<223> OTHER INFORMATION: any amino acid, preferably Arg, His or Lys
<220> FEATURE:
<221> NAME/KEY: MOD_RES
<222> LOCATION: (44)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (85)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (93)
<223> OTHER INFORMATION: any amino acid, preferably Lys, Arg, His, Asn
```

```
              or Gln
<220> FEATURE:
<221> NAME/KEY: MOD_RES
<222> LOCATION: (98)
<223> OTHER INFORMATION: any amino acid, preferably Lys, Arg or His
<220> FEATURE:
<221> NAME/KEY: MOD_RES
<222> LOCATION: (112)
<223> OTHER INFORMATION: any amino acid, preferably Ser, Thr, Tyr, Trp
      or Phe
<220> FEATURE:
<221> NAME/KEY: MOD_RES
<222> LOCATION: (132)
<223> OTHER INFORMATION: any amino acid, preferably Lys, Arg or His
<220> FEATURE:
<221> NAME/KEY: MOD_RES
<222> LOCATION: (137)
<223> OTHER INFORMATION: any amino acid, preferably Met, Cys, Ser or Thr
<220> FEATURE:
<221> NAME/KEY: MOD_RES
<222> LOCATION: (139)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (181)
<223> OTHER INFORMATION: any amino acid, preferably Leu, Val, Met, Thr
      or Ser
<220> FEATURE:
<221> NAME/KEY: MOD_RES
<222> LOCATION: (183)
<223> OTHER INFORMATION: any amino acid, preferably His, Phe, Tyr, Ser,
      Thr, Met or Cys
<220> FEATURE:
<221> NAME/KEY: MOD_RES
<222> LOCATION: (185)
<223> OTHER INFORMATION: any amino acid, preferably Gln, Asn, Glu or Asp
<220> FEATURE:
<221> NAME/KEY: MOD_RES
<222> LOCATION: (186)
<223> OTHER INFORMATION: any amino acid, preferably His, Phe, Tyr, Thr,
      Gln, Asn, Glu or Asp
<220> FEATURE:
<221> NAME/KEY: MOD_RES
<222> LOCATION: (189)
<223> OTHER INFORMATION: any amino acid, preferably Gln, Asn, Glu, Asp,
      Thr, Ser, Met or Cys
<220> FEATURE:
<221> NAME/KEY: MOD_RES
<222> LOCATION: (191)
<223> OTHER INFORMATION: any amino acid, preferably Ala, Gly, Cys, Leu,
      Val or Met
<220> FEATURE:
<221> NAME/KEY: MOD_RES
<222> LOCATION: (196)
<223> OTHER INFORMATION: any amino acid, preferably Arg, Lys, Met, Ile,
      Asn, Asp, Glu, Gln, Ser, Thr or Cys
<220> FEATURE:
<221> NAME/KEY: MOD_RES
<222> LOCATION: (200)
<223> OTHER INFORMATION: any amino acid, preferably Arg, Lys, Met or Ile
<220> FEATURE:
<221> NAME/KEY: MOD_RES
<222> LOCATION: (206)
<223> OTHER INFORMATION: any amino acid, preferably Ala, Gly, Cys, Asp,
      Glu, Gln, Asn, Ser, Thr or Met
<220> FEATURE:
<221> NAME/KEY: MOD_RES
<222> LOCATION: (207)
<223> OTHER INFORMATION: any amino acid, preferably Ala, Gly, Cys, Asp,
      Asn, Glu or Gln
<220> FEATURE:
<221> NAME/KEY: MOD_RES
<222> LOCATION: (209)
<223> OTHER INFORMATION: any amino acid, preferably Arg, Lys, Met, Ile,
      Asn, Asp, Glu or Gln
<220> FEATURE:
<221> NAME/KEY: MOD_RES
<222> LOCATION: (211)
<223> OTHER INFORMATION: any amino acid, preferably Leu, Val, Met or Ile
```

```
<220> FEATURE:
<221> NAME/KEY: MOD_RES
<222> LOCATION: (212)
<223> OTHER INFORMATION: any amino acid, preferably Phe, Tyr, Thr, His
      or Trp
<220> FEATURE:
<221> NAME/KEY: MOD_RES
<222> LOCATION: (216)
<223> OTHER INFORMATION: any amino acid, preferably Ile, Val, Leu or Met
<220> FEATURE:
<221> NAME/KEY: MOD_RES
<222> LOCATION: (217)
<223> OTHER INFORMATION: any amino acid, preferably Met, Cys, Ile, Leu,
      Val, Thr or Ser
<220> FEATURE:
<221> NAME/KEY: MOD_RES
<222> LOCATION: (219)
<223> OTHER INFORMATION: any amino acid, preferably Leu, Val, Met, Thr
      or Ser

<400> SEQUENCE: 21

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
 50                  55                  60

Asp Glu Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
        195                 200                 205

Xaa Leu Xaa Xaa Ser Asp Phe Xaa Xaa Phe Xaa Asp Arg
    210                 215                 220

<210> SEQ ID NO 22
<211> LENGTH: 167
<212> TYPE: PRT
<213> ORGANISM: Artificial Sequence
<220> FEATURE:
<223> OTHER INFORMATION: Description of Artificial Sequence: Synthetic
      degenerate hedgehog polypeptide general formula
<220> FEATURE:
<221> NAME/KEY: MOD_RES
<222> LOCATION: (7)..(7)
<223> OTHER INFORMATION: any amino acid, preferably Gly, Ala, Val, Leu,
      Ile, Pro, Phe or Tyr
<220> FEATURE:
<221> NAME/KEY: MOD_RES
<222> LOCATION: (8)..(8)
```

```
<223> OTHER INFORMATION: any amino acid, preferably Gly, Ala, Val, Leu
      or Ile
<220> FEATURE:
<221> NAME/KEY: MOD_RES
<222> LOCATION: (9)..(9)
<223> OTHER INFORMATION: any amino acid, preferably Gly, Ala, Val, Leu,
      Ile, Lys, His or Arg
<220> FEATURE:
<221> NAME/KEY: MOD_RES
<222> LOCATION: (12)..(12)
<223> OTHER INFORMATION: any amino acid, preferably Lys, Arg or His
<220> FEATURE:
<221> NAME/KEY: MOD_RES
<222> LOCATION: (13)..(13)
<223> OTHER INFORMATION: any amino acid, preferably Phe, Trp, Tyr or not
      present
<220> FEATURE:
<221> NAME/KEY: MOD_RES
<222> LOCATION: (14)..(14)
<223> OTHER INFORMATION: any amino acid, preferably Gly, Ala, Val, Leu,
      Ile or not present
<220> FEATURE:
<221> NAME/KEY: MOD_RES
<222> LOCATION: (17)..(17)
<223> OTHER INFORMATION: any amino acid, preferably Asn, Gln, His, Arg
      or Lys
<220> FEATURE:
<221> NAME/KEY: MOD_RES
<222> LOCATION: (19)..(19)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (22)..(22)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (27)..(27)
<223> OTHER INFORMATION: any amino acid, preferably Gly, Ala, Val, Leu,
      Ile, Ser or Thr
<220> FEATURE:
<221> NAME/KEY: MOD_RES
<222> LOCATION: (29)..(29)
<223> OTHER INFORMATION: any amino acid, preferably Ser, Thr, Gln or Asn
<220> FEATURE:
<221> NAME/KEY: MOD_RES
<222> LOCATION: (30)..(30)
<223> OTHER INFORMATION: any amino acid, preferably Met, Cys, Gly, Ala,
      Val, Leu, Ile, Ser or Thr
<220> FEATURE:
<221> NAME/KEY: MOD_RES
<222> LOCATION: (31)..(31)
<223> OTHER INFORMATION: any amino acid, preferably Gly, Ala, Val, Leu,
      Ile or Pro
<220> FEATURE:
<221> NAME/KEY: MOD_RES
<222> LOCATION: (33)..(33)
<223> OTHER INFORMATION: any amino acid, preferably Arg, His or Lys
<220> FEATURE:
<221> NAME/KEY: MOD_RES
<222> LOCATION: (40)..(40)
<223> OTHER INFORMATION: any amino acid, preferably Gly, Ala, Val, Leu,
      Ile, Pro, Arg, His or Lys
<220> FEATURE:
<221> NAME/KEY: MOD_RES
<222> LOCATION: (41)..(41)
<223> OTHER INFORMATION: any amino acid, preferably Gly, Ala, Val, Leu,
      Ile, Phe or Tyr
<220> FEATURE:
<221> NAME/KEY: MOD_RES
<222> LOCATION: (44)..(44)
<223> OTHER INFORMATION: any amino acid, preferably Arg, His or Lys
<220> FEATURE:
<221> NAME/KEY: MOD_RES
<222> LOCATION: (45)..(45)
<223> OTHER INFORMATION: any amino acid, preferably Gly, Ala, Val, Leu,
      Ile, Ser or Thr
<220> FEATURE:
<221> NAME/KEY: MOD_RES
```

-continued

```
<222> LOCATION: (46)..(46)
<223> OTHER INFORMATION: any amino acid, preferably Thr or Ser
<220> FEATURE:
<221> NAME/KEY: MOD_RES
<222> LOCATION: (48)..(48)
<223> OTHER INFORMATION: any amino acid, preferably Gly, Ala, Val, Leu,
      Ile, Asn or Gln
<220> FEATURE:
<221> NAME/KEY: MOD_RES
<222> LOCATION: (53)..(53)
<223> OTHER INFORMATION: any amino acid, preferably Arg, His or Lys
<220> FEATURE:
<221> NAME/KEY: MOD_RES
<222> LOCATION: (54)..(54)
<223> OTHER INFORMATION: any amino acid, preferably Asp or Glu
<220> FEATURE:
<221> NAME/KEY: MOD_RES
<222> LOCATION: (71)..(71)
<223> OTHER INFORMATION: any amino acid, preferably Ser or Thr
<220> FEATURE:
<221> NAME/KEY: MOD_RES
<222> LOCATION: (79)..(79)
<223> OTHER INFORMATION: any amino acid, preferably Glu, Asp, Gln or Asn
<220> FEATURE:
<221> NAME/KEY: MOD_RES
<222> LOCATION: (83)..(83)
<223> OTHER INFORMATION: any amino acid, preferably Glu or Asp
<220> FEATURE:
<221> NAME/KEY: MOD_RES
<222> LOCATION: (84)..(84)
<223> OTHER INFORMATION: any amino acid, preferably Arg, His or Lys
<220> FEATURE:
<221> NAME/KEY: MOD_RES
<222> LOCATION: (85)..(85)
<223> OTHER INFORMATION: any amino acid, preferably Gly, Ala, Val, Leu
      or Ile
<220> FEATURE:
<221> NAME/KEY: MOD_RES
<222> LOCATION: (87)..(87)
<223> OTHER INFORMATION: any amino acid, preferably Gly, Ala, Val, Leu,
      Ile, Thr or Ser
<220> FEATURE:
<221> NAME/KEY: MOD_RES
<222> LOCATION: (95)..(95)
<223> OTHER INFORMATION: any amino acid, preferably Met, Cys, Gln, Asn,
      Arg, Lys or His
<220> FEATURE:
<221> NAME/KEY: MOD_RES
<222> LOCATION: (100)..(100)
<223> OTHER INFORMATION: any amino acid, preferably Arg, His or Lys
<220> FEATURE:
<221> NAME/KEY: MOD_RES
<222> LOCATION: (107)..(107)
<223> OTHER INFORMATION: any amino acid, preferably Trp, Phe, Tyr, Arg,
      His or Lys
<220> FEATURE:
<221> NAME/KEY: MOD_RES
<222> LOCATION: (114)..(114)
<223> OTHER INFORMATION: any amino acid, preferably Gly, Ala, Val, Leu,
      Ile, Ser, Thr, Tyr or Phe
<220> FEATURE:
<221> NAME/KEY: MOD_RES
<222> LOCATION: (115)..(115)
<223> OTHER INFORMATION: any amino acid, preferably Gln, Asn, Asp or Glu
<220> FEATURE:
<221> NAME/KEY: MOD_RES
<222> LOCATION: (116)..(116)
<223> OTHER INFORMATION: any amino acid, preferably Asp or Glu
<220> FEATURE:
<221> NAME/KEY: MOD_RES
<222> LOCATION: (125)..(125)
<223> OTHER INFORMATION: any amino acid, preferably Gly, Ala, Val, Leu,
      or Ile
<220> FEATURE:
<221> NAME/KEY: MOD_RES
<222> LOCATION: (134)..(134)
<223> OTHER INFORMATION: any amino acid, preferably Arg, His or Lys
<220> FEATURE:
<221> NAME/KEY: MOD_RES
<222> LOCATION: (135)..(135)
```

<223> OTHER INFORMATION: any amino acid, preferably Asn, Gln, Thr or Ser
<220> FEATURE:
<221> NAME/KEY: MOD_RES
<222> LOCATION: (139)..(139)
<223> OTHER INFORMATION: any amino acid, preferably Gly, Ala, Val, Leu,
      Ile, Ser, Thr, Met or Cys
<220> FEATURE:
<221> NAME/KEY: MOD_RES
<222> LOCATION: (141)..(141)
<223> OTHER INFORMATION: any amino acid, preferably Gly, Ala, Val, Leu,
      Ile, Thr or Ser
<220> FEATURE:
<221> NAME/KEY: MOD_RES
<222> LOCATION: (157)..(157)
<223> OTHER INFORMATION: any amino acid, preferably Arg, His or Lys
<220> FEATURE:
<221> NAME/KEY: MOD_RES
<222> LOCATION: (158)..(158)
<223> OTHER INFORMATION: any amino acid, preferably Asn, Gln, Gly, Ala,
      Val, Leu or Ile
<220> FEATURE:
<221> NAME/KEY: MOD_RES
<222> LOCATION: (160)..(160)
<223> OTHER INFORMATION: any amino acid, preferably Gly, Ala, Val, Leu
      or Ile
<220> FEATURE:
<221> NAME/KEY: MOD_RES
<222> LOCATION: (162)..(162)
<223> OTHER INFORMATION: any amino acid, preferably Gly, Ala, Val, Leu,
      Ile, Ser, Thr or Cys
<220> FEATURE:
<221> NAME/KEY: MOD_RES
<222> LOCATION: (166)..(166)
<223> OTHER INFORMATION: any amino acid, preferably Gly, Ala, Val, Leu,
      Ile, Thr or Ser
<220> FEATURE:
<221> NAME/KEY: MOD_RES
<222> LOCATION: (167)..(167)
<223> OTHER INFORMATION: any amino acid, preferably Asp or Glu

<400> SEQUENCE: 22

Cys Gly Pro Gly Arg Gly Xaa Xaa Xaa Arg Arg Xaa Xaa Xaa Pro Lys
  1               5                  10                  15

Xaa Leu Xaa Pro Leu Xaa Tyr Lys Gln Phe Xaa Pro Xaa Xaa Xaa Glu
             20                  25                  30

Xaa Thr Leu Gly Ala Ser Gly Xaa Xaa Glu Gly Xaa Xaa Xaa Arg Xaa
         35                  40                  45

Ser Glu Arg Phe Xaa Xaa Leu Thr Pro Asn Tyr Asn Pro Asp Ile Ile
     50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
             85                  90                  95

Pro Gly Val Xaa Leu Arg Val Thr Glu Gly Xaa Asp Glu Asp Gly His
            100                 105                 110

His Xaa Xaa Xaa Ser Leu His Tyr Glu Gly Arg Ala Xaa Asp Ile Thr
        115                 120                 125

Thr Ser Asp Arg Asp Xaa Xaa Lys Tyr Gly Xaa Leu Xaa Arg Leu Ala
        130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
            165

<210> SEQ ID NO 23
<211> LENGTH: 74
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 23
gcgcgcttcg aagcgaggca gccagcgagg gagagagcga gcgggcgagc cggagcgagg      60
aaatcgatgc gcgc                                                       74

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgcgcagat ctgggaaagc gcaagagaga gcgcacacgc acacaccgc cgcgcgcact       60 cgggatccgc gcgc                                                       74

<210> SEQ ID NO 25
<211> LENGTH: 996
<212> TYPE: DNA
<213> ORGANISM: Artificial Sequence
<220> FEATURE:
<223> OTHER INFORMATION: Description of Artificial Sequence: Synthetic
      gene activation construct

<400> SEQUENCE: 25
cgaagcgagg cagccagcga gggagagagc gagcgggcga gccggagcga ggaaatcgaa      60
ggttcgaatc cttcccccac caccatcact ttcaaaagtc cgaaagaatc tgctccctgc    120
ttgtgtgttg gaggtcgctg agtagtgcgc gagtaaaatt taagctacaa caaggcaagg    180
cttgaccgac aattgcatga agaatctgct tagggttagg cgttttgcgc tgcttcgcga    240
tgtacgggcc agatatacgc gttgacattg attattgact agttattaat agtaatcaat    300
tacggggtca ttagttcata gcccatatat ggagttccgc gttacataac ttacggtaaa    360
tggcccgcct ggctgaccgc ccaacgaccc ccgcccattg acgtcaataa tgacgtatgt    420
tcccatagta acgccaatag ggactttcca ttgacgtcaa tgggtggact atttacggta    480
aactgcccac ttggcagtac atcaagtgta tcatatgcca gtacgccccc tattgacgt     540 caatgacggt aaatggcccg cctggcatta tgcccagtac atgaccttat gggactttcc    600
tacttggcag tacatctacg tattagtcat cgctattacc atggtgatgc ggttttggca    660
gtacatcaat gggcgtggat agcggtttga ctcacgggga tttccaagtc tccaccccat    720
tgacgtcaat gggagtttgt tttggcacca aaatcaacgg gactttccaa aatgtcgtaa    780
caactccgcc ccattgacgc aaatgggcgg taggcgtgta cggtgggagg tctatataag    840
cagagctctc tggctaacta gagaacccac tgcttactgg cttatcgaaa ttaatacgac    900
tcactatagg gagacccaag cttggtaccg agctcggatc gatctgggaa agcgcaagag    960
agagcgcaca cgcacacacc cgccgcgcgc actcgg                              996

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      antisense construct

<400> SEQUENCE: 26
```

```
gtcctggcgc cgccgccgcc gtcgcc                                          26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      antisense construct

<400> SEQUENCE: 27
ttccgatgac cggcctttcg cggtga                                          26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      antisense construct

<400> SEQUENCE: 28
gtgcacggaa aggtgcaggc cacact                                          26

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgtgctcga cgttgtcact g                                               21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatcccctca gaagaactcg t                                               21

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Gly Asp Ser
  1
```

METHODS AND COMPOSITIONS FOR REGULATING LYMPHOCYTE ACTIVITY

REFERENCE TO RELATED APPLICATIONS

This application claims the benefit of the filing date of U.S. Provisional Application No. 60/546,571, filed on Feb. 20, 2004; and is a continuation-in-part application of U.S. Ser. No. 09/724,964, filed on Nov. 28, 2000, now U.S. Pat. No. 6,951,839, which claims the benefit of the filing date of U.S. Provisional Application No. 60/168,112, filed on Nov. 30, 1999; and is a continuation-in-part application of U.S. Ser. No. 10/989,693, filed on Nov. 16, 2004, now abandoned, which is a divisional application of U.S. Ser. No. 09/724,964, filed on Nov. 28, 2000, now U.S. Pat. No. 6,951,839, which claims the benefit of the filing date of U.S. Provisional Application No. 60/168,112, filed on Nov. 30, 1999. The entire contents of each of these applications are incorporated herein by reference.

BACKGROUND OF THE INVENTION

The lymphoid system performs critical functions in animals that include preventing and combating infection, and surveillance and immune elimination of tumor cells. Loss of immune function leads to an immunocompromised status that can predispose the host to serious and life-threatening disease. Functional abnormalities may be present in any of the elements that participate in mediating an immune response, e.g., cellular or humoral elements such as granulocytes, lymphocytes, complement, antibody, or cytokines.

The immune system is a network of cells adapted to protect the organism against pathogens and cells that are not recognized as "self." Once the immune system is activated, it enlists the participation of a variety of cells and molecules to mount an effector function designed to eliminate the "non-self" entity within the body. Lymphocytes are cells of the immune system that are capable of specifically recognizing and selectively eliminating foreign entities. By contrast to other cells of the immune system, such as neutrophils which are considered non-specific in their reactions to invaders, the characteristics of lymphocytes confer specificity, diversity, memory and self/nonself recognition to the immune response.

There are two major populations of lymphocytes: B lymphocytes and T lymphocytes. B lymphocytes originate and mature within the bone marrow and are responsible for formation of antibody molecules. T lymphocytes also arise from the bone marrow but mature in the thymus. There are two major subpopulations of T-cells: T helper cells and T cytotoxic cells. The two types of T cells can be distinguished by the presence of one of two membrane glycoproteins, either CD4 or CD8. The T-helper cells (which express CD4) when activated by antigen-complexes (foreign molecules coupled to special proteins) respond by secreting various growth factors known collectively as cytokines. These cytokines are signals that activate other cells of the immune system, including the T-cytotoxic cells. The T-cytotoxic cells (which express CD8) when activated, proliferate and differentiate into cytotoxic T lymphocytes (CTL) which are able to monitor for and eliminate from the body pathogenic cells, foreign cells, virus-infected cells, and tumor cells. The normal development, maturation and differentiation of T lymphocytes are regulated by various peptide factors.

The thymus, the primary site of T cell production, is formed during fetal development by seeding of the thymic primordium by blood-borne lymphocyte progenitor cells T from the fetal liver (Akashi et al., *Curr. Opin. Immunol.* 12: 144, 2000). The development of mature T cells is dependent on interactions between the developing lymphocyte precursors and the thymic stroma, made up of thymic epithelial cells and mesenchyme-derived cells (Anderson et al., *Annu. Rev. Immunol.* 14: 73, 1996). Thymocyte development has been defined by cell surface expression of developmentally regulated markers: the most immature $CD4^-CD8^-$ double-negative (DN) thymocytes give rise to $CD4^+CD8^+$ double-positive (DP) thymocytes, which give rise to mature $CD4^+CD8^-$ single-positive (SP) and $CD4^-CD8^+$ SP T cells. The DN population can be further subdivided by the expression of CD44 and CD25: $CD44^+CD25^-$ (DN1) cells differentiate into $CD44^+CD25^+$ (DN2) cells, which give rise to $CD44^-CD25^+$ (DN3) cells, which finally become the most mature $CD44^-CD25^-$ (DN4) DN population. The DN4 cells may pass through an intermediate population expressing either coreceptor alone before becoming DP cells. This intermediate population, most commonly expressing CD8, is known as immature single positive (ISP) cells. Progression beyond the DN3 stage is dependent on successful rearrangement of a TCRβ-chain gene and pre-TCR signaling, whereas differentiation from DP to mature SP cell is dependent on the expression and positive selection of an αβTCR (Von Boehmer et al., *Immunol. Rev.* 191: 62, 2003; Ceredig and Rolink, *Nat. Rev. Immunol.* 2: 888, 2002).

The most immature DN1 cells express CD45 and CD117, but are not fully committed to the T cell lineage. The DN1 population contains cells that can give rise to T, B, NK, and dendritic cells (Akashi, supra). As thymocytes proceed along their program of differentiation they become progressively more committed to the T cell lineage, and DN3 cells that have TCRβ VDJ arrangements are irreversibly committed (Ceredig and Rolink, supra).

SUMMARY OF THE INVENTION

The present invention provides methods and compositions for modulating the immune function of an animal by administering an agent which induces, or alternatively inhibits, hedgehog-mediated signal transduction. Thus, the subject method can be used as an immunosuppressive, e.g., by administering a high dose of a hedgehog agonist or antagonist to foster a high level of activity of the hedgehog (HH) pathway or to substantially eliminate HH signalling (particularly in the thymus), or as an immunostimulant, e.g., by administering a low dose of a hedgehog agonist or a hedgehog antagonist to modulate activity of the Hedgehog pathway around an optimal level, e.g., in the thymus.

When the subject method is carried out using a hedgehog agonist, the hedgehog agonist may be a polypeptide including a hedgehog portion comprising at least a bioactive extracellular portion of a hedgehog protein, e.g., the hedgehog portion includes at least 50, 100 or 150 (contiguous) amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID NOs: 10-18 or 20, though sequences identical to those sequence listing entries are also contemplated as useful in the present method. The hedgehog portion can be encoded by a nucleic acid which hybridizes under stringent conditions to a nucleic acid sequence of any of SEQ ID NOs: 1-9 or 19, e.g., the hedgehog portion can be encoded by a vertebrate hedgehog gene, especially a human hedgehog gene.

In other embodiments, the subject method can be carried out by administering a gene activation construct, wherein the gene activation construct is designed to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent.

In yet another embodiment, the subject method can be carried out by administering a HH agonist (such as a small molecule agonist) that stimulates HH signaling as induced by the HH polypeptide.

In yet other embodiments, the subject method can be carried out using a ptc antagonist. An exemplary ptc antagonist is a small organic molecule which binds to a patched protein and derepresses patched-mediated inhibition of mitosis, e.g., a molecule which binds to patched and mimics hedgehog-mediated patched signal transduction, which binds to patched and regulates patched-dependent gene expression. For instance, the binding of the ptc antagonist to patched may result in upregulation of patched and/or gli expression.

In a more generic sense, the ptc antagonist can be a small organic molecule which interacts with MK cells to induce hedgehog-mediated patched signal transduction, such as by altering the localization, protein-protein binding and/or enzymatic activity of an intracellular protein involved in a patched signal pathway. For instance, the ptc agonist/antagonist may alter the level of expression of a hedgehog protein, a patched protein or a protein involved in the intracellular signal transduction pathway of patched.

In certain embodiments, the ptc antagonist is an antisense construct which inhibits the expression of a protein which is involved in the signal transduction pathway of patched and the expression of which antagonizes hedgehog-mediated signals. The antisense construct is preferably an oligonucleotide of about 20-30 nucleotides in length and having a GC content of at least 50 percent.

In other embodiments, the ptc therapeutic is an inhibitor of protein kinase A (PKA), such as a 5-isoquinolinesulfonamide. The PKA inhibitor can be a cyclic AMP analog. Exemplary PKA inhibitors include N-[2-((p-bromocinnamyl)amino)ethyl]-5-isoquinolinesulfonamide, 1-(5-isoquinolinesulfonyl)-2-methylpiperazine, KT5720, 8-bromo-cAMP, dibutyryl-cAMP and PKA Heat Stable Inhibitor isoform α. Another exemplary PKA inhibitor is represented in the general formula:

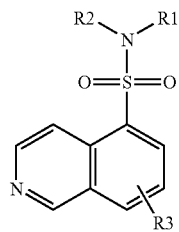

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

DETAILED DESCRIPTION OF THE INVENTION

I. Overview

Figure 1:
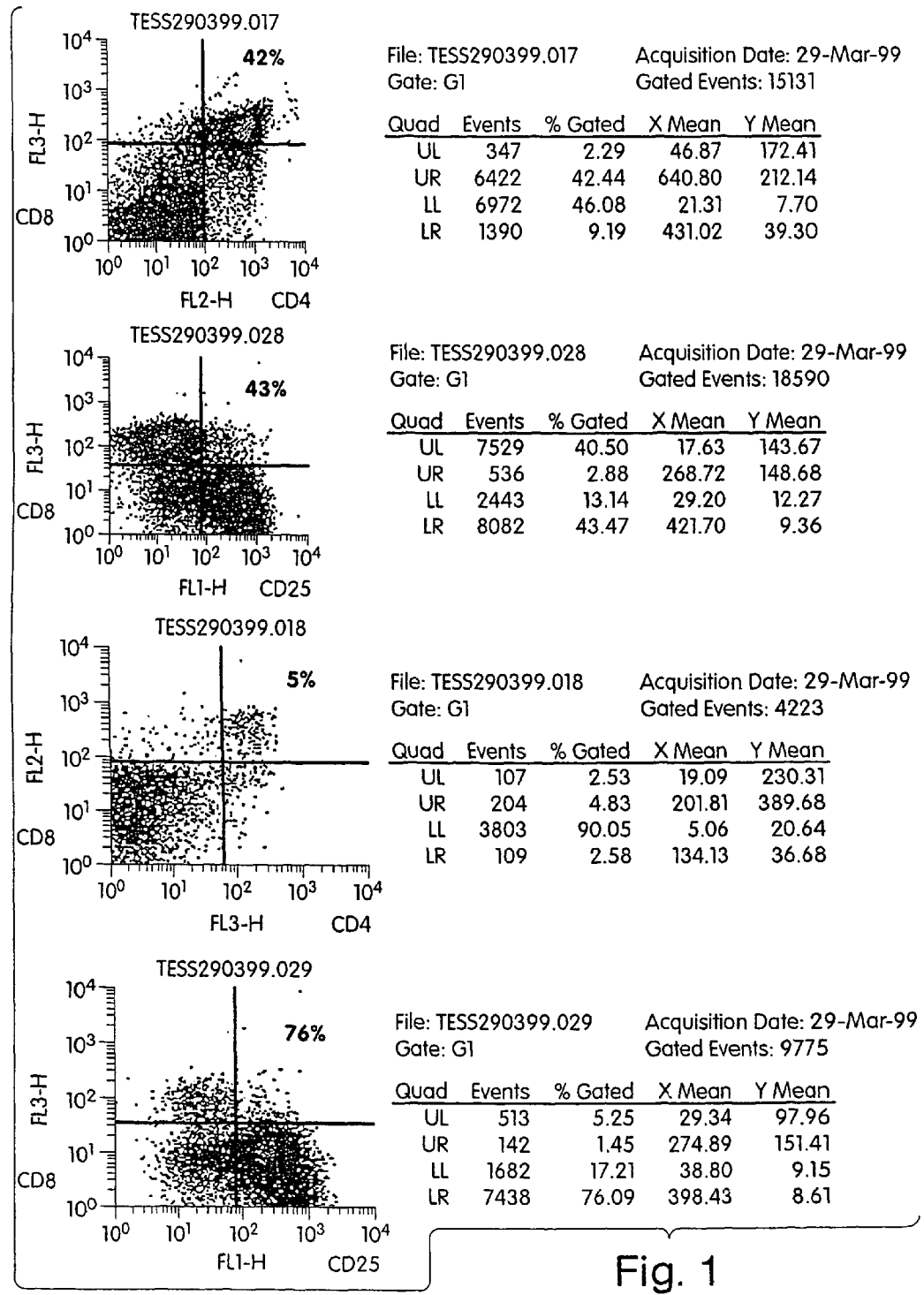
FIGS. 1-4 illustrate the profile for staining with various markers for T-cell maturity.
Figure 2:
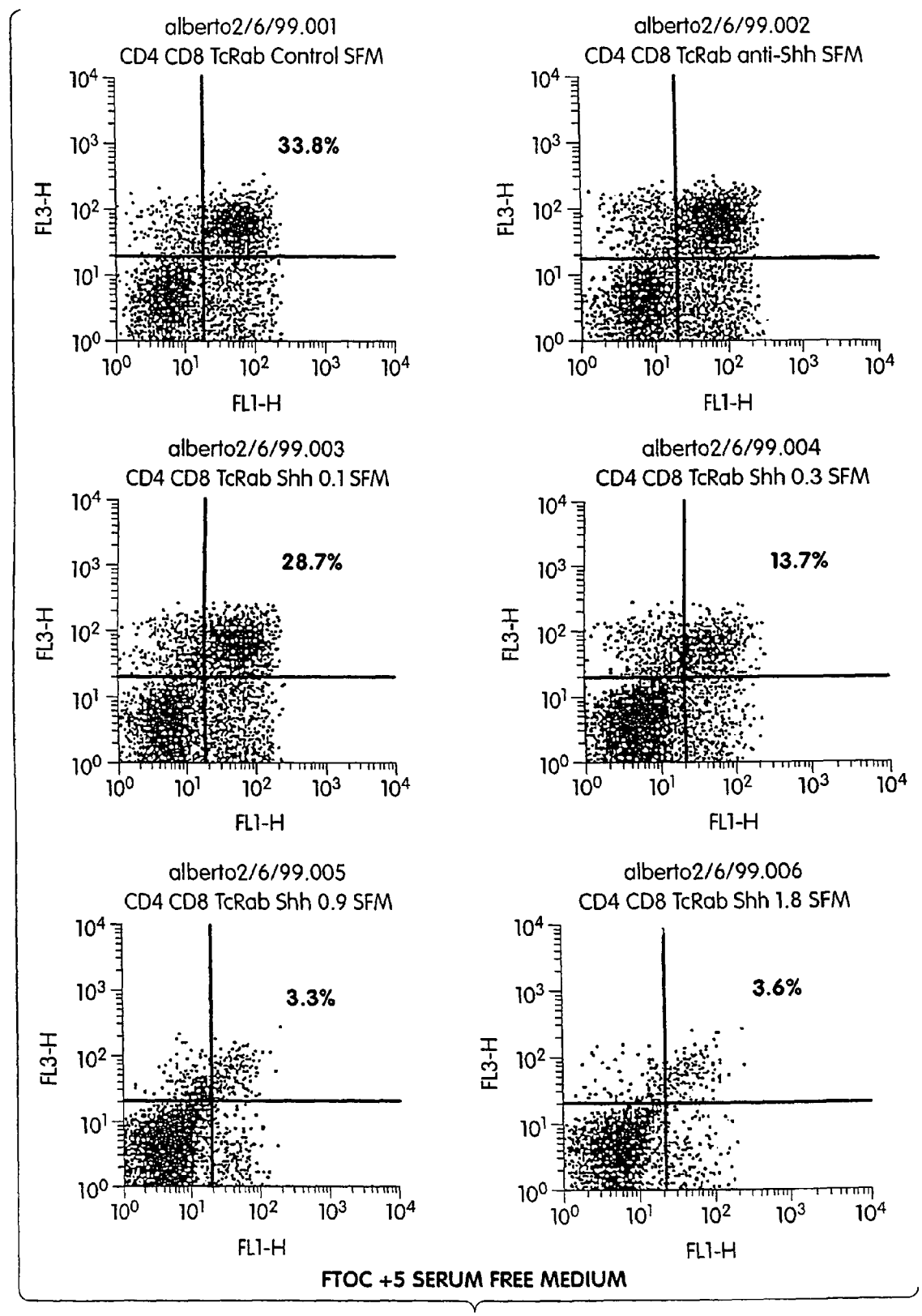
Figure 3:
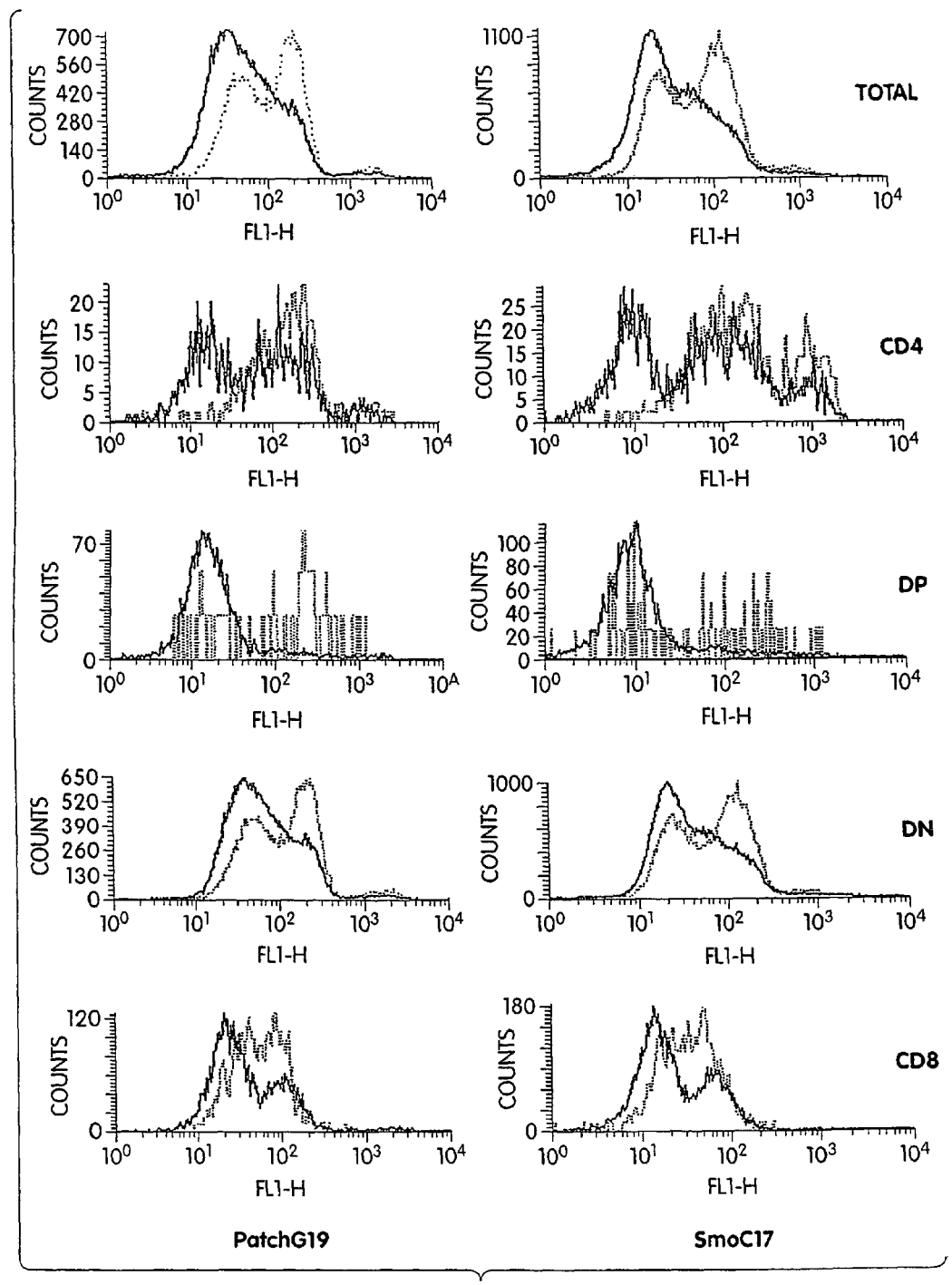
Figure 4:
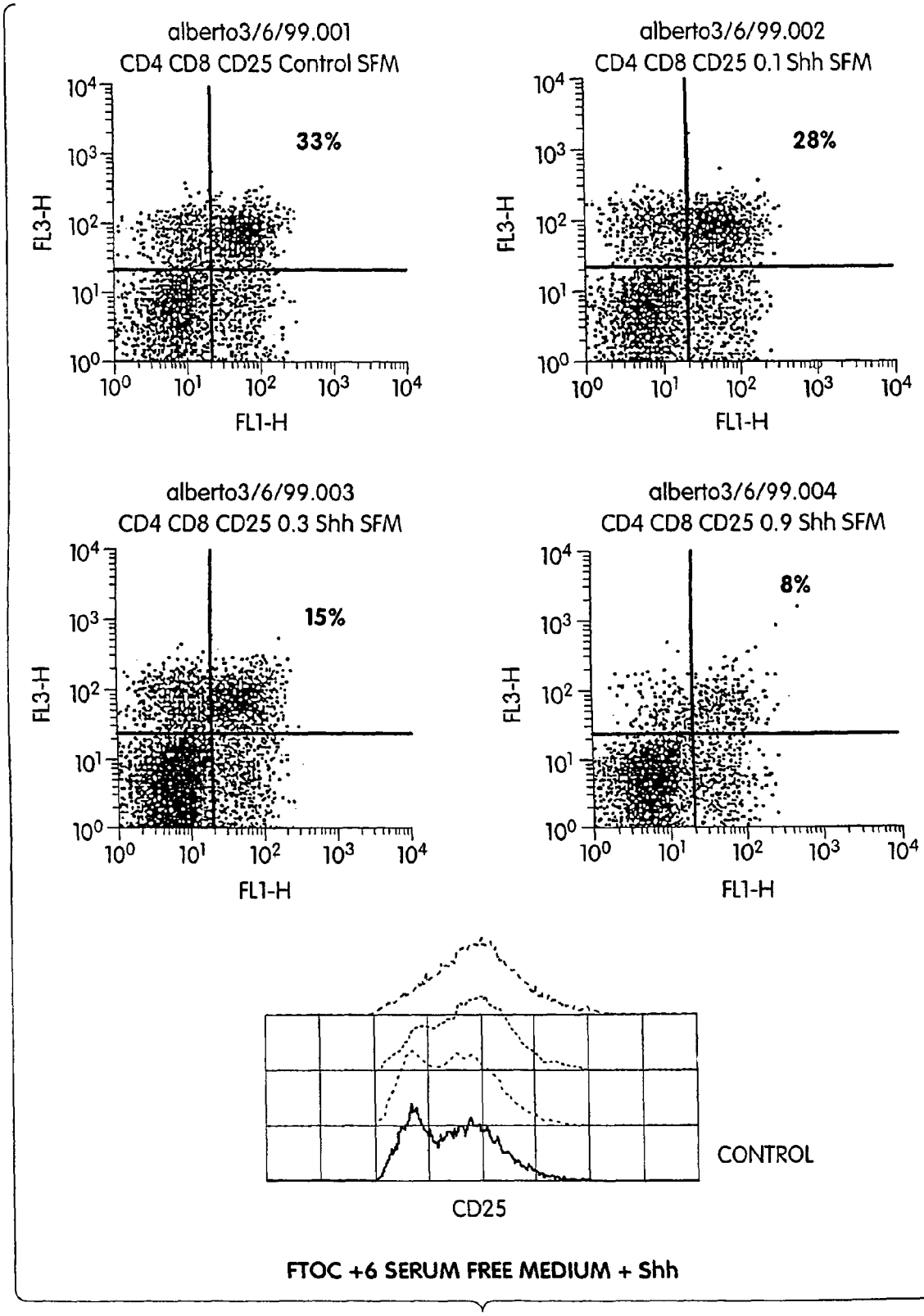
Figure 5A:
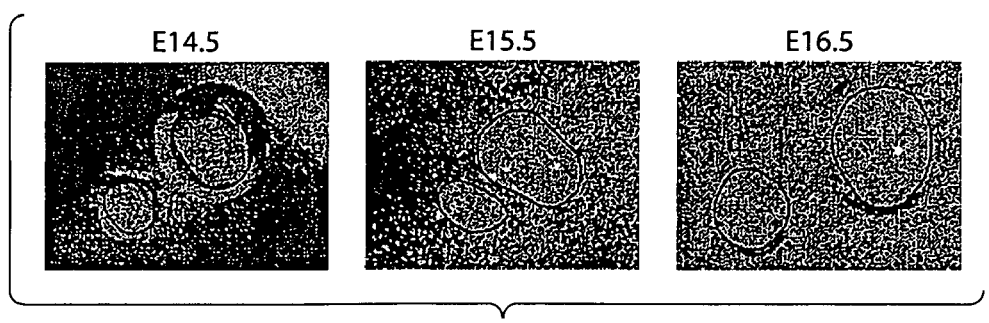
FIG. 5 Shh controls thymus size and thymocyte differentiation from DN1 to DN2 on E13.5. (A) Control thymus (right) and Shh−/− thymus (left) on E14.5, E15.5 and E16.5. (B) Thymus cellularity on E13.5. To allow comparison between litters, the number of cells recovered from each embryonic thymus was divided by the mean number of cells recovered from wildtype embryonic thymi from the same litter, to give a relative cell number from three different E13.5 litters. The difference in cellularity between Shh−/− and Shh+/+ thymi was statistically significant by Students t-test (p=0.001). (C) The relative percentage of CD45+ on E13.5. To allow comparison between litters, the percentage of CD45+ cells within the live gate from each embryonic thymus was divided by the mean percentage of CD45+ cells recovered from wildtype thymi. The difference in percentage of CD45+ cells between Shh−/− and Shh+/+ thymi was statistically significant by Students t-test (p=<0.0001). (D) Flow cytometry of E13.5 thymi stained with anti-CD45, anti-CD44 and anti-CD25. Upper panel: FSC/SSC profiles of Shh+/+, +/− and −/− E13.5 thymus, showing the live gate used. Middle panel: Dot plot of anti-CD45 staining versus FSC, showing the gate used for analysis of lymphocyte precursors. The percentage of cells in the gate is given. Lower panel: The composition of DN subsets, gated on CD45 and stained with anti-CD44 and anti-CD25. The percentage of cells in each quadrant is given. (E) The relative percentage of CD25+ in E13.5 thymi. To allow comparison between litters, the percentage of CD25+ DN cells in each embryonic thymus was divided by the mean percentage of CD25+ DN cells in wildtype thymi from the same litter. The difference in percentage of CD25+ cells between Shh−/− and Shh+/+ thymi was statistically significant by Students t-test (p=0.0001).
Figure 5B:
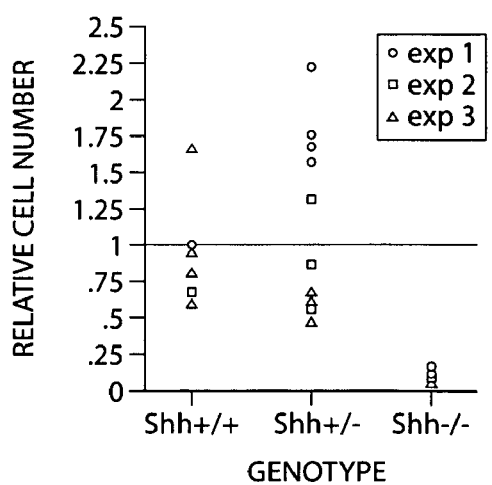
Figure 5C:
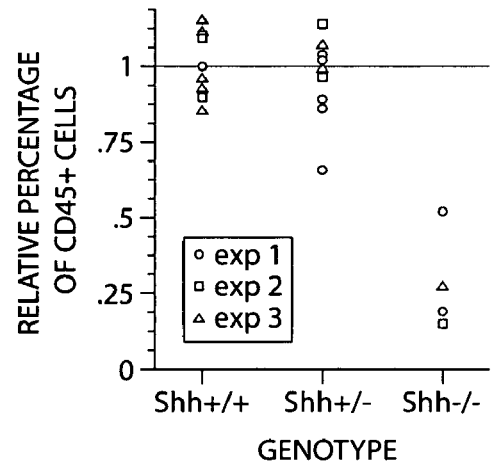
Figure 5D:
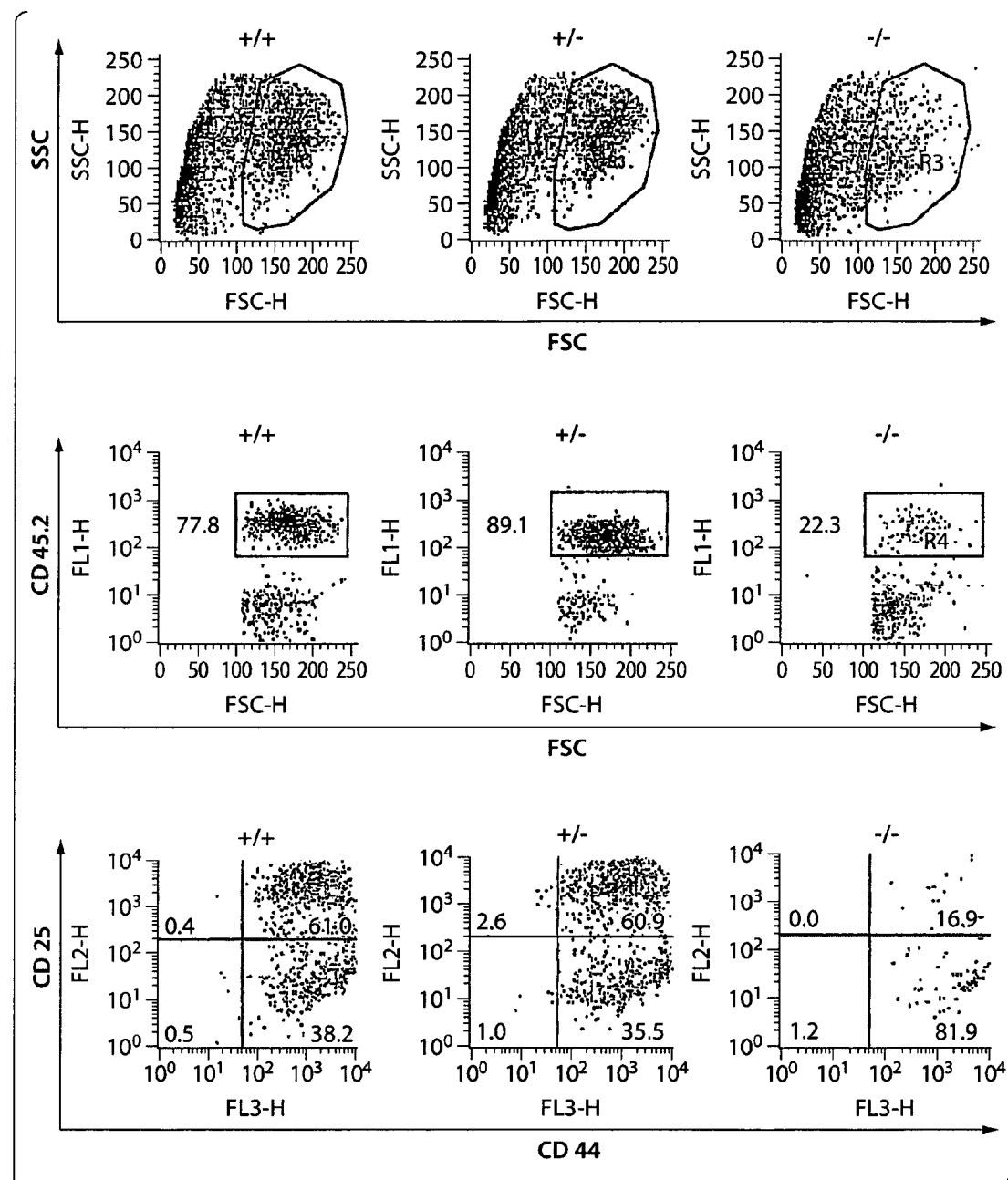
Figure 5E:
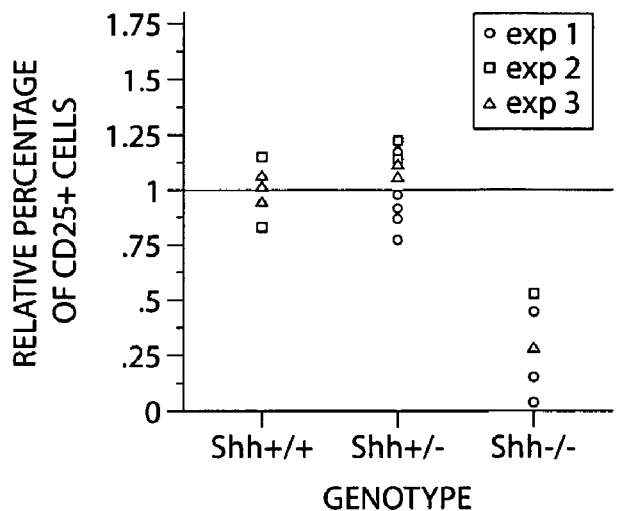
Figure 5F:
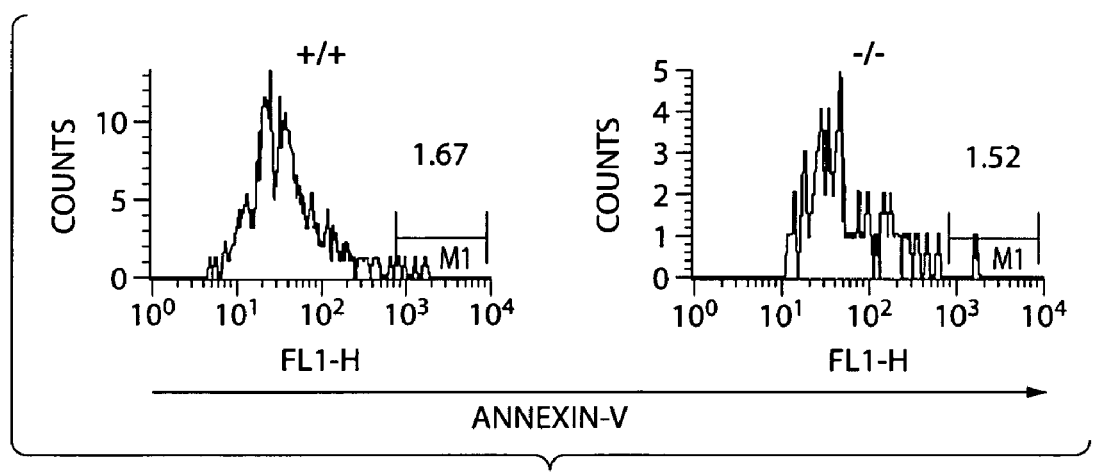

The present application is directed to the surprising discovery that different levels of activity of the hedgehog pathway are useful to regulate maturation of T lymphocytes. High levels of HH signaling block early T cell development, likely at the DN3 sub-stage. However, low levels of HH signaling are required for early T lymphocyte (T cell) development, especially development of T cell precursors from the DN1 sub-stage to the DN2 sub-stage, and again from the CD4CD8 double negative (DN) stage to the double positive (DP) stage. Therefore, by modulating HH signaling activity, either through the use of HH agonist or antagonist depending on specific circumstances, the level of activity of the HH signaling can be modulated to achieve the desired result, i.e., promotion or inhibition of host immune reaction.

To illustrate, to promote T cell development, and thus enhance host immune response, it is necessary to achieve a low level of HH signaling in target tissues/cells, especially thymus, where T cells mature. In a patient with a high level of HH activity in thymus, HH antagonists, preferably administered locally into the thymus (though optionally through systemic or other routes of administration), can be used to downregulate the amount of HH signaling to the range within which optimal T cell development can occur (see below). Alternatively, in cultured T cell precursor or thymus tissue/organ cultures, which may not itself produce sufficient HH, a low dose of HH peptide or agonist may be used to achieve a similarly low level of HH signaling to facilitate T cell development.

On the other hand, to inhibit T cell development, and thus inhibit host immune response, one can either induce high level of HH signaling resulting, for example, from administration of high amount of HH protein or agonists, or inhibit HH signalling to a low level (below the threshold level necessary for proper T cell development), such as by administration of an appropriate amount of a HH antagonist.

Therefore, certain aspects of the invention are directed to preparations of hedgehog polypeptides, or other molecules which regulate patched or smoothened signalling (agonists and antagonists), and their uses as immunomodulatory agents against diseases including both acquired and hereditary immunological disorders.

For instance, such compositions can be used to increase the population of T-helper cells to optimum levels in the host, e.g, to stimulate the immune system of the animal. Such uses of the subject compositions can be used in the treatment of bacterial or viral infections, as well as to help the body fight against cancer cells. Alternatively, these substances also enable the host to adjust to diseases arising from errant self-recognition processes in which there is excessive attack by host T-cells against endogenous tissues. In such instances, the subject compositions can be used to reduce T-cell population so that the signs and symptoms of self-directed inflammatory (autoimmune) diseases such rheumatoid arthritis and multiple sclerosis are ameliorated.

As described herein, a high dose of hedgehog proteins inhibits maturation of T lymphocytes, especially at the stage of DN3 T-cell precursors. While not wishing to be bound by any particular theory, this presumably occurs through activation of the HH signaling pathway to achieve high level of HH signaling activity in target tissues/cells. On the other hand, a high dose of hedgehog antagonist drops the level of HH signaling in target tissues/cells to below the threshold level necessary for early T cell development, thereby inhibiting T lymphocyte maturation. Based upon its inhibitory effect, the administration of a high dose of hedgehog or ptc agonists/antagonists (defined infra) is suggested herein as a treatment for several types of immunological disorders involving unwanted activation of cellular immunity, e.g., graft rejection, autoimmune disorders, and the like.

In other embodiments, a low dose of an inhibitor of hedgehog signalling pathways (HH antagonist) can be used as immunostimulatory agents, e.g., to counteract the effects of endogenous activation of a hedgehog/ptc pathway. Such antagonists may help to achieve an appropriately low level of HH activity in target tissues, such as the thymus, thus allowing efficient T-cell development at various stages, such as from DN1 to DN2, and/or from DN to DP cells. Similarly, in a host animal with insufficient level of HH signaling necessary for early T cell development, a low dose of HH agonist might help to upregulate the HH signaling to the level needed for proper T cell development, thus stimulating host immune response.

In general, the method of the present invention comprises administering to an animal, or to cultured lymphocytes in vitro, an amount of a hedgehog or ptc agonist/antagonist which produces a non-toxic response by the cell of inhibition of maturation (in the case of a high dose of hedgehog agonist or antagonist) or promotion of T cell maturation (in the case of a low dose of hedgehog antagonist or agonist). The subject method can be carried out on cells which may be either dispersed in culture or a part of an intact tissue or organ. Moreover, the method can be performed on cells which are provided in culture (in vitro), or on cells in a whole animal (in vivo).

In one aspect, the present invention provides pharmaceutical preparations and methods for treating or preventing hyperimmune or hypoimmune disorders utilizing, as an active ingredient, a hedgehog polypeptide or a hedgehog agonist. The invention also relates to methods of controlling the functional performance of T cells by use of the pharmaceutical preparations of the invention.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

Without wishing to be bound by any particular theory, the inhibitory effect of high dose of hedgehog proteins or agonists on T cell maturation may be due at least in part to the ability of hedgehog proteins/agonists to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In other tissue, the introduction of hedgehog relieves (derepresses) this inhibition conferred by patched, allowing expression of particular gene programs.

Recently, it has been reported that mutations in the human version of patched, a gene first identified in a fruit fly developmental pathway, cause a hereditary skin cancer and may contribute to sporadic skin cancers. See, for example, Hahn et al. (1996) *Cell* 86: 841-851; and Johnson et al. (1996) *Science* 272: 1668-1671. The demonstration that nevoid basal-cell carcinoma (NBCC) results from mutations in the human patched gene provided an example of the roles patched plays in post-embryonic development. These observations have led the art to understand one activity of patched to be a tumor suppressor gene, which may act by inhibiting proliferative signals from hedgehog. Our observations set forth below reveal potential new roles for the hedgehog/patched pathway in maintenance of mature T-cells and other lymphocytic cell lines. Accordingly, the present invention contemplates the use of other agents which are capable of mimicking or antagonizing, depending on the desired consequence, the effect of the hedgehog protein on patched signalling, e.g., as may be identified from the drug screening assays described below.

Without wishing to be bound by any particular theory, the stimulatory effect of low dose of hedgehog proteins or agonists on T cell maturation may be due at least in part to the need for a low level of hedgehog signaling during early stages of T-cell maturation, especially from the DN1 to the DN2 subpopulation of DN immature T-cells, and again from the DN to the DP immature T-cells. Low doses of hedgehog protein or agonist may also be needed for cellular expansion of the DN thymocyte population. Similarly, such a low level of HH signaling may also be achieved through the use of appropriate amount of HH antagonists, i.e., to down-regulate undesirably high levels of HH activity, to achieve a low level desirable for early T cell development. Therefore, the invention contemplates regulating the effective level of HH signaling in target tissues such as thymus, using, for example, certain HH agonists or antagonists, to achieve low levels of HH signalling that are optimal for T cell development. The method can be used to treat patients in need of T-cell function, such as in patients with bacterial or viral infection (including HIV infection), or cancer.

II. Definitions

For convenience, certain terms employed in the specification, examples, and appended claims are collected here.

The term "hedgehog therapeutic" refers to various forms of hedgehog polypeptides, HH agonists or antagonists, as well as peptidomimetics, which can modulate the proliferation/differentiation state of lymphocytes, by, as will be clear from the context of individual examples, mimicking or potentiating (agonizing) or inhibiting (antagonizing) the effects of a naturally-occurring hedgehog protein. A hedgehog therapeutic which mimics or potentiates the activity of a wild-type hedgehog protein is a "hedgehog agonist". Conversely, a hedgehog therapeutic which inhibits the activity of a wild-type hedgehog protein is a "hedgehog antagonist."

As used herein, "high dose of HH therapeutic agents" may include high doses of HH agonists effective to inhibit T cell development as described below; or high doses of HH antagonists effective to inhibit T cell development as described below, such as by down-regulating HH signaling level to below the minimal level required for T cell development.

As used herein, "low dose of HH therapeutic agents" may include a low dose of HH agonists sufficient to achieve the low level of HH signaling activity required for early T cell development; or an appropriate amount of HH antagonists effective to down regulate the overall level of HH signaling to within that range required for T cell development.

In particular, the term "hedgehog polypeptide" encompasses preparations of hedgehog proteins and peptidyl fragments thereof, both agonist and antagonist forms as the specific context will make clear.

As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog bioactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "ptc therapeutic" refers to agents which either (i) mimic the effect of hedgehog proteins on patched signalling, e.g., which antagonize the cell-cycle inhibitory and/or T-cell maturation promoting activity of patched, or (ii) activate or potentiate patched signalling. In other embodiments, the ptc therapeutic can be a hedgehog antagonist. The ptc therapeutic can be, e.g., a peptide, a nucleic acid, a carbohydrate, a small organic molecule, or natural product extract (or fraction thereof).

An "effective amount" of, e.g., a hedgehog or ptc agonist/antagonist, with respect to the subject method of treatment, refers to an amount of a composition, e.g., a hedgehog polypeptide, in a preparation which, when applied as part of a desired dosage regimen brings enhances or inhibits (as the case may be) T-cell maturation, relative to the absence of the hedgehog or ptc agonist/antagonist, according to clinically acceptable standards for the disorder to be treated. For different purposes, "an effective amount" of the same compound may have different concentrations. For example, an effective amount of hedgehog for inhibiting T-cell development may be 0.5 µg/ml in thymus, while an effective amount of hedgehog for stimulating T-cell development may be 0.0005 µg/ml in thymus.

A "patient" or "subject" to be treated by the subject method can mean either a human or non-human animal, including non-human mammal.

The "growth state" of a cell refers to the rate of proliferation of the cell and the state of differentiation of the cell.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a naturally occurring hedgehog sequence.

The term "corresponds to," when referring to a particular polypeptide or nucleic acid sequence is meant to indicate that the sequence of interest is identical or homologous to the reference sequence to which it is said to correspond.

The terms "recombinant protein," "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$-$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

The term "CD4$^+$ lymphocyte" is intended to mean a lymphocyte having a plurality of cell surface CD4 molecules as evidenced by binding of an antibody specific for CD4 to the cell surface, e.g., monoclonal antibody OKT4 (Ortho Diagnostics, Piscataway, N.J.).

The term "CD8$^+$ lymphocyte" is intended to mean a lymphocyte having a plurality of cell surface CD8 molecules as evidenced by binding of an antibody specific for CD8 to the cell surface, e.g., monoclonal antibody OKT8 (Ortho Diagnostics, Piscataway, N.J.).

"Peripheral blood leukocytes", abbreviated PBL, are intended to mean the cellular components of the immune system in blood, e.g., lymphocytes, monocytes, eosinophils, basophils, neutrophils, plasma cells, mast cell precursors, and the like.

"Lymphocytes" are intended to encompass T-lymphocytes, (also referred to as T-cells), B-lymphocytes (also referred to as B-cells), natural killer-lymphocytes (NK-cells), cytotoxic T lymphocytes (CTL), T-helper lymphocytes, delta gamma-T-cell receptor bearing cells as well as precursors and activated derivatives thereof.

"Activated lymphocyte" is intended to mean that subset of lymphocytes which has been i) exposed to a stimulus, and ii) has been triggered to change from a metabolically-quiescent cell into a cell with increased protein synthesis and/or DNA and RNA synthesis and possibly cell division. Illustrative stimuli and triggering pathways leading to activated lymphocytes include interaction of T cell receptors with antigens, interaction of interleukin receptors with interleukins, interaction of growth factor receptors with growth factors, interaction of lymphocyte cell surface determinants with antibody (e.g., anti-CD2) or mitogens (e.g., PHA), and the like.

"Subject in need thereof" is intended to mean a mammal having one or more clinical or laboratory indicia of a disorder or disease. The subject may exhibit clinical disease activity or may have a subclinical or latent infection. Subjects in need thereof include human and non-human primates, mammals, domestic animals, livestock, and the like, e.g., dogs, cats, rodents, birds, horses, cows, pigs and fish.

As used herein, the terms "agent" and "compound" include both protein and non-protein moieties. An agent may be a small organic molecule, a polypeptide, a protein, a peptide complex, a peptidomimetic, a non-peptidyl agent, or a polynucleotide.

As used herein, "ameliorates" means alleviate, lessen, or and decrease the extent of a symptom or decrease the number of occurrence of episodes of a disease manifestation.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. Optionally, an antibody can be labeled with a detectable marker. Detectable markers include, for example, radioactive or fluorescent markers. Antibodies may also be modified by coupling them to other biologically or chemically functional moieties such as cross-linking agents or peptides.

As used herein, the term "dsRNA" refers to small interference RNA (siRNA) molecules, or other RNA molecules including a double stranded feature and able to be processed to siRNA in cells, such as hairpin RNA moieties.

The term "ED50" means the dose of a drug which produces 50% of its maximum response or effect.

The term "gain-of-function," as it refers to genes inhibited by the subject RNAi method, refers to a increase in the level of expression of a gene when compared to the level in the absence of RNAi constructs.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "Hh agonist" refers to an agent which potentiates or recapitulates the bioactivity of Hh, such as to activate transcription of target genes, especially gli-1. The term "Hh agonist" as used herein refers not only to any agent that may act by directly activating the normal function of a Hh or smoothened polypeptide, but also to any agent that activates the Hh signaling pathway, including any agent that relieves repression or suppression of a negative regulatory element of the pathway, such as the Patched protein. Thus, an Hh agonist may be an inhibitor of a negative regulatory element of the Hh signaling pathway. As used herein, the term "Hh agonist" includes RNA interference (RNAi) modulators that suppress the expression of negative-control elements within the Hh signaling pathway. Preferred Hh agonists can be used to mimic or enhance the activity or effect of Hh polypeptide in a smoothened-dependent manner. Another type of preferred Hh agonists disrupt the association of the Smoothened and Patched polypeptides, relieving the repressive effect of Patched and activating the Hh pathway.

The term "Hh antagonist" refers to an agent which inhibits or attenuates the bioactivity of Hh, such as to inhibit transcription of target genes, especially gli-1. The term "Hh antagonist" as used herein refers not only to any agent that may act by directly inhibiting the normal function of a Hh or Smoothened polypeptide, but also to any agent that attenuates the Hh signaling pathway, including any agent that enhances repression or suppression of a negative regulatory element of the pathway, such as the Patched protein. Thus, an Hh antagonist may be an enhancer of a negative regulatory element of the Hh signaling pathway. Another type of preferred Hh antagonists enhances the association of the Smoothened and Patched polypeptides, enhancing the repressive effect of Patched and repressing the Hh pathway.

As used herein, the term "Hh antagonist" includes RNA interference (RNAi) modulators that suppress the expression of activating elements within the Hh signaling pathway. In most cases, an RNAi antagonist would inhibit the activity of the target protein by, for example, decreasing production of a protein encoded by a gene in the Hh pathway including genes that enhances the pathway, thus downregulating Hh signaling. Preferred Hh antagonists can be used to inhibit or attenuate the activity or effect of Hh polypeptide in a smoothened-dependent manner. The term "hh RNAi antagonist" refers to an RNAi agent that inhibits the bioactivity of a hh signaling component, such that it represses the expression of the target hh signaling component which normally acts as an activator of hh signaling. For example, certain preferred hh RNAi agonists can be used to inhibit hedgehog, smoothened or gli-1 mRNA.

The term "Hh polypeptide" refers any protein expressed from a gene belonging to the hh gene family, its mutants and functionally equivalent polypeptides. A "gene family" means a group of genes that share a common function and exhibit common sequence homology.

The term "hh RNAi agonist" refers to an RNAi agent that inhibits the bioactivity of a hh signaling component (for example gli-3), such that it represses the expression of the target hh signaling component which normally acts as a suppressor or a repressor of the hh signaling. For example, certain preferred hh RNAi agonists can be used to overcome a ptc gain-of-function and/or a gli-3 gain-of-function. Other preferred RNAi agonists can be used to relieve suppression in hh signal transduction. An RNAi agonist may be directed to a gene encoding a protein in the Hh signaling pathway. In most cases, the RNAi agonist would inhibit the activity of the target protein by, for example, decreasing production of a protein encoded by a gene in the Hh pathway which negatively regulates the pathway, thus upregulating Hh signaling.

As used herein, "inhibits" means that the amount is reduced as compared with the amount that would occur in a control sample. In a preferred embodiment, inhibits means that the amount is reduced by more than 50%, even more preferably by more than 75% or even 100%. As used herein, "instruction material" means a document or recorded media including a written or audible instruction for the use of a pharmaceutical composition. An instruction material includes a label on a bottle, a paper inserted a box, printing on the box or carton, instructions provided by a website at an address given in any of these locations, etc.

The term "$LD_{50}$" means the dose of a drug which is lethal in 50% of test subjects.

As used herein, the phrase "mediates RNAi" refers to the ability to distinguish which RNAs are to be degraded by the RNAi process, e.g., degradation occurs in a sequence-specific manner rather than by a sequence-independent dsRNA response, e.g., a PKR response.

The term "preventing" is art-recognized, and when used in relation to a condition, such as recurrence or onset of a disease, is well understood in the art, and includes administration of a composition which reduces the frequency of, or delays the onset of, symptoms of a medical condition in a subject relative to a subject which does not receive the composition. Thus, prevention of a disease includes, for example, reducing the occurrence and severity of the disease in a population of patients receiving a prophylactic treatment relative to an untreated control population, and/or delaying the onset of the disease in a treated population compared to untreated population.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "siRNA" stands for a small interfering RNA.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

A "subject" or "patient" to be treated by the subject method can mean either a human or non-human animal.

As used herein, "treating" means either slowing, stopping or reversing the progression of the disorder. In the preferred embodiment, "treating" means reversing the progression to the point of eliminating the disorder.

The term "acylamino" is art-recognized and refers to a moiety that can be represented by the general formula:

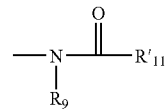

wherein $R_9$ is as defined above, and $R'_{11}$ represents a hydrogen, an alkyl, an alkenyl or $-(CH_2)_m-R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

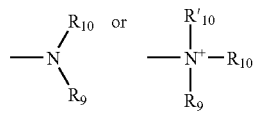

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term 'amine' does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

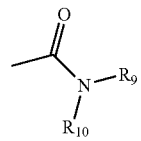

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

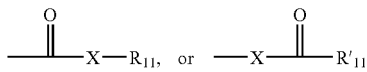

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R'_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

A "phosphonamidite" can be represented in general formula:

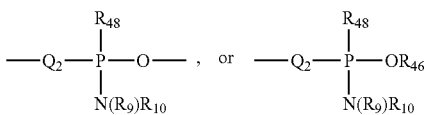

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in general formula:

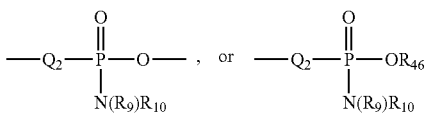

wherein $R_9$ and $R_{10}$ are as defined above, and $Q_2$ represents O, S or N.

A "phosphoryl" can in general be represented by the formula:

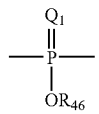

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

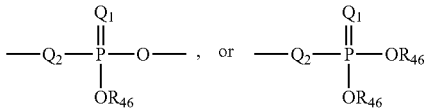

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

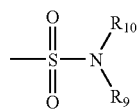

in which $R_9$ and $R_{10}$ are as defined above.

The term "sulfate" is art recognized and includes a moiety that can be represented by the general formula:

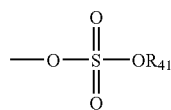

in which $R_{41}$ is as defined above.

The term "sulfonamido" is art recognized and includes a moiety that can be represented by the general formula:

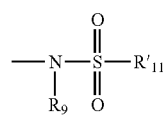

in which $R_9$ and $R'_{11}$ are as defined above.

The term "sulfonate" is art-recognized and includes a moiety that can be represented by the general formula:

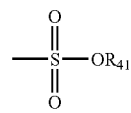

in which $R_{41}$ is an electron pair, hydrogen, alkyl, cycloalkyl, or aryl.

The terms "sulfoxido" or "sulfinyl", as used herein, refers to a moiety that can be represented by the general formula:

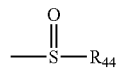

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

III. Exemplary Applications of Method and Compositions

According to the invention, preparations with ptc and hedgehog agonist/antagonists are used in immunoregulatory disorders and diseases in animals and humans, for the prevention or prophylaxis, control, diagnosis or treatment thereof.

The subject method has wide applicability to the treatment or prophylaxis of disorders affecting the regulation of lymphocytes, particularly maturation and/or activation of T lymphocytes. In general, the method can be characterized as including a step of administering to an animal an amount of a ptc or hedgehog agonist/antagonist effective to alter the proliferative and/or differentiation state of treated lymphocytes. Such agonist/antagonist compositions may be useful in treatments designed to modulate, e.g., increase or decrease, an immunological response. Such diseases and conditions include, but are not limited to, infection (such as bacterial or viral infection), metabolic disease such as diabetes, nutritional deficiency, toxic agents, graft rejection or other hyperacute response, or autoimmune disorders. The goals of treatment in each case can be twofold: (1) to eliminate the cause of the disease or unwanted immunological response, and/or (2) to relieve its symptoms.

In view of their immunosuppressant activity, the hedgehog proteins (and agonists thereof) are suitable for preventing and treating diseases and conditions which require a temporary or permanent reduction or suppression of an immune response. In particular, their use extends to suppressing the activation of the proliferation of lymphocytes or cytotoxic T-cells and/or immunocytes, e.g. for preventing or treating autoimmune diseases such as diseases of the rheumatic type, multiple sclerosis, psoriasis, atopic dermatitis, or for preventing the rejection of transplanted tissues or organs such as kidneys, heart, lungs, bone marrow, spleen, skin or cornea, in undesirable reactions during or after transfusions, allergic diseases, particularly those which affect the gastrointestinal tract and which may take the form of an inflammation, or inflammatory, proliferative and hyperproliferative diseases and cutaneous manifestations of immunological disorders such as eczematous dermatitis, urticaria, vasculitis and scleroderma.

Thus, it is particularly advantageous to use immunosuppressive forms of the subject hedgehog and ptc agonists/antagonists clinically for the disorders, diseases and conditions described above, i.e. when it is desirable to achieve immunosuppression in an animal or human body.

Depending on the nature and cause of the disease or disorder to be treated or the condition which is to be influenced in an animal or human body, it may be desirable to administer the hedgehog or ptc agonist/antagonist preparation systemically, locally or topically to the tissue or organ in question. Systemic action is desirable, for example, when various organs or organ systems are in need of treatment, as is the case for example in systemic autoimmune diseases or allergies or in transplants of large, foreign organs or tissues. By contrast, a local effect would be considered if only local manifestations of an immunological occurrence had to be treated, e.g. in small transplants of skin or cornea or in cases of local dermatitis.

Depending on the duration and intensity of the immunosuppressant activity required, the hedgehog or ptc agonist/antagonist preparations may be given one or more times a day, as well as intermittently, over a period of several days, weeks or months and in various dosages.

In still other embodiments, antagonist (lymphocyte maturation promoting) forms of the subject ptc and hedgehog therapeutics, or low dose of hedgehog agonists/antagonists, can be used to treat disorders involving hypoimmunity, e.g., immunosuppressed or immunocompromised patients. For instance, the effect of high-dose hedgehog-induced immunosuppression, e.g., possibly resulting from endogenous or heterologous activation of the hedgehog signalling pathway, can be counteracted using antagonist forms of the subject ptc and hedgehog agonists/antagonists.

Thus, the subject method contemplates the treatment of immunocompromised subjects to increase one or more indicia of cell mediated immunity (CMI), humoral immunity, or innate resistance to infection, by administering pharmaceutical preparations of an activating ptc or hedgehog agonist/antagonist. In certain embodiments, such immunity-promoting activities of antagonists forms of the subject ptc and hedgehog therapeutics can be identified, e.g., by i) increased E-rosette forming cells (E-RFC) in thymocyte cultures after incubation with the subject ptc or hedgehog agonist/antagonist agents; ii) increased E-RFC in cultures of thymocytes from aged animals after incubation with the subject ptc or hedgehog agonist/antagonist agents; and, iii) increased expression of OKT 4<+> in cultures of human peripheral blood T-lymphocytes from patients with secondary immunodeficiency syndromes following treatment with the subject ptc or hedgehog agonist/antagonist agents. Increased expression of CD2 and CD4 accessory molecules on T-lymphocytes is compatible with a heighten the state of innate or induced immunity to infection, e.g., by upregulating T-helper and cytotoxic T-lymphocytes to respond to lower levels of antigen.

Immunodeficiency states fall into three general etiologic categories. First, there is immunosuppression that occurs as a consequence of disease processes. Second, there are immunodeficiencies that arise because of therapy for other diseases, so-called iatrogenic immunodeficiencies. Third, immunodeficiencies may result from direct attack of T-lymphocytes by the human immunodeficiency virus (HIV) that causes the acquired immunodeficiency syndrome (AIDS).

Common disease processes that lead to immunodeficiency are malnutrition, neoplasias, aging, and infections. Malnourished people, patients with advanced widespread cancers and people with debilitating illnesses become sick and die more often because impaired cell-mediated and humoral immune responses increase susceptibility to infections by a variety of organisms. A state of generalized deficiency in immune responses is called anergy. Various types of infections, especially viral infections, lead to immunosuppression. A drug, such as a maturation-promoting form of a Ptc or hedgehog agonist/antagonist, e.g., capable of making the T-helper lymphocyte components of the immune system more robust, will be an important therapeutic agent for increasing the resistance of the patient to infections. For example, Ptc or hedgehog agonist/antagonist or its analogs, may be:

administered to patients, especially older patients, before or just after admissions to hospitals in order to reduce the risks of nosocomial (hospital-induced) infections, a common and severe clinical problem;

administered to burn victims, because such individuals are especially prone to infections;

administered to patients in anticipation of epidemic infections, for example, in conjunction with influenza vaccinations or hepatitis vaccinations, to invigorate the immune response to pathogens;

administered to patients with asymptomatic viral infections, in order to enhance immune surveillance of pathogenic organisms and reduce the likelihood of recurrence of disease, for example, for individuals who are carriers of herpes viruses, varicella viruses, hepatitis viruses and HIV.

Iatrogenic immunosuppression is most often due to drug therapies which either kill or functionally inactivate lymphocytes. Various chemotherapeutic drugs are administered to cancer patients, and these drugs are usually cytotoxic to both mature and developing lymphocytes as well as to granulocyte and monocyte precursors. Thus, cancer chemotherapy is almost always accompanied by a period of immunosuppression and increased risk of infections. Radiation treatment of cancer carries the same risks. Medications (granulocyte-colony stimulating factor) exist for increasing neutrophils in blood to combat infections that occur after cancer chemotherapy, but no medications are currently used for restoring lymphocytic functions. Major surgery, for example repair of aneurysms or by-pass operations, also decrease immune function in humans. The reasons for the decline in blood lymphocytes that occur because of major surgery are not clear, but an agent that elevates lymphocyte functions in such patients have therapeutic value in decreasing the likelihood of infections.

One final form of acquired immunosuppression that should be mentioned results from the absence of a spleen, caused by surgical removal of the organ after trauma or for the treatment of certain hematologic diseases or as a result of infarction in sickle cell disease. Patients without spleens are more susceptible to infections by some organisms, particularly encapsulated bacteria such as *Streptococcus pneumoniae*. The spleen is apparently required for the induction of protective humoral immune responses to such organisms. The subject Ptc or hedgehog agonists/antagonists can help individuals without a spleen or without a thymus in resistance against infection by micro-organisms.

Since very low dose of hedgehog protein is insufficient to sustain the progression of T-cell development from DN1 to DN2 cells, and from DN to DP cells, excessive amount of hedgehog antagonists may inhibit T-cell development (and thus becomes immunosuppressant). Therefore, it is contemplated that only a therapeutically effective (but not excessive) amount of hedgehog antagonist is provided to achieve the right amount of active hedgehog signaling at the target tissue such as thymus. On the other hand, excessive amount of HH antagonists, which is capable of reducing the active amount of HH to below the minimally required amount of HH for T cell development, can be used as immunosuppressant.

It is also contemplated that the HH protein, HH agonist, and HH antagonist could be delivered locally to thymus, preferably in a slow-release format, to maintain the active level of HH in thymus at desired concentration, so as to enhance or inhibit T cell development. There are numerous devices or implants suitable for sustained drug release in human body or bodies of other mammals; see, for example, U.S. Pat. No. 6,685,452; U.S. Pat. Application publication 20030153901A1, etc.

IV. Exemplary Hedgehog Agonist/Antagonist Compounds

The hedgehog agonist/antagonist compositions of the subject method includes various HH peptides, HH agonists and antagonists as described below. These compositions can be generated by any of a variety of techniques, including purification of naturally occurring proteins, recombinantly produced proteins and synthetic chemistry.

Hedgehog Polypeptides and Active Fragments Thereof

Polypeptide forms of the hedgehog agonists/antagonists are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject agonists/antagonists can be derived are characterized by a signal peptide, a highly conserved N-terminal region, and a more divergent C-terminal domain. In addition to signal sequence cleavage in the secretory pathway (Lee, J. J. et al. (1992) *Cell* 71: 33-50; Tabata, T. et al. (1992) *Genes Dev.* 2635-2645; Chang, D. E. et al. (1994) *Development* 120: 3339-3353), hedgehog precursor proteins naturally undergo an internal autoproteolytic cleavage which depends on conserved sequences in the C-terminal portion (Lee et al. (1994) *Science* 266: 1528-1537; Porter et al. (1995) *Nature* 374: 363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15: 2294-2303; Porter et al. (1995) supra; Ekker, S. C. et al. (1995) *Curr. Biol.* 5: 944-955; Lai, C. J. et al. (1995) *Development* 121: 2349-2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) *Development* 121: 2537-2547; Roelink, H. et al. (1995) *Cell* 81: 445-455). Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single *Drosophila* hedgehog gene (SEQ ID NO: 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID NO: 1; a mouse Dhh polypeptide is encoded by SEQ ID NO: 2; a mouse Ihh polypeptide is encoded by SEQ ID NO: 3; a mouse Shh polypeptide is encoded by SEQ ID NO: 4 a zebrafish Shh polypeptide is encoded by SEQ ID NO: 5; a human Shh polypeptide is encoded by SEQ ID NO: 6; a human Ihh polypeptide is encoded by SEQ ID NO: 7; a human Dhh polypeptide is encoded by SEQ ID NO: 8; and a zebrafish Thh is encoded by SEQ ID NO: 9.

TABLE 1

Guide to hedgehog sequences in Sequence Listing

| | Nucleotide | Amino Acid |
|---|---|---|
| Chicken Shh | SEQ ID NO: 1 | SEQ ID NO: 10 |
| Mouse Dhh | SEQ ID NO: 2 | SEQ ID NO: 11 |
| Mouse Ihh | SEQ ID NO: 3 | SEQ ID NO: 12 |
| Mouse Shh | SEQ ID NO: 4 | SEQ ID NO: 13 |
| Zebrafish Shh | SEQ ID NO: 5 | SEQ ID NO: 14 |
| Human Shh | SEQ ID NO: 6 | SEQ ID NO: 15 |
| Human Ihh | SEQ ID NO: 7 | SEQ ID NO: 16 |
| Human Dhh | SEQ ID NO: 8 | SEQ ID NO: 17 |
| Zebrafish Thh | SEQ ID NO: 9 | SEQ ID NO: 18 |
| *Drosophila* HH | SEQ ID NO: 19 | SEQ ID NO: 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein.

In addition to proteolytic fragmentation, the vertebrate hedgehog proteins can also be modified post-translationally, such as by glycosylation and/or addition of lipophilic moieties, such as stents, fatty acids, etc., though bacterially produced (e.g. unmodified) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

There are a wide range of lipophilic moieties with which hedgehog polypeptides can be derivatived. The term "lipophilic group", in the context of being attached to a hedgehog polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, sterols, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

In one embodiment, the hedgehog polypeptide is modified with one or more sterol moieties, such as cholesterol. See, for example, PCT publication WO 96/17924. In certain embodiments, the cholesterol is preferably added to the C-terminal glycine were the hedgehog polypeptide corresponds to the naturally-occurring N-terminal proteolytic fragment.

In another embodiment, the hedgehog polypeptide can be modified with a fatty acid moiety, such as a myrostoyl, palmitoyl, stearoyl, or arachidoyl moiety. See, e.g., Pepinsky et al. (1998) *J. Biol. Chem* 273: 14037.

In addition to those effects seen by cholesterol-addition to the C-terminus or fatty acid addition to the N-terminus of extracellular fragments of the protein, at least certain of the biological activities of the hedgehog gene products are unexpectedly potentiated by derivativation of the protein with lipophilic moieties at other sites on the protein and/or by moieties other than cholesterol or fatty acids. Certain aspects of the invention are directed to the use of preparations of hedgehog polypeptides which are modified at sites other than N-terminal or C-terminal residues of the natural processed form of the protein, and/or which are modified at such terminal residues with lipophilic moieties other than a sterol at the C-terminus or fatty acid at the N-terminus.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2-CH(OH)—O—(C12-C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc.

Other exemplary lipophilic moieties include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(−)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

The hedgehog polypeptide can be linked to the hydrophobic moiety in a number of ways including by chemical coupling means, or by genetic engineering.

There are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) *Bioconjugate Chemistry* 1: 2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2: 263, incorporated by reference herein). Ellman's Reagent can be used to calculate the quantity of sulfhydryls in a particular protein (see for example Ellman et al. (1958) Arch. Biochem. Biophys. 74: 443 and Riddles et al. (1979) Anal. Biochem. 94: 75, incorporated by reference herein).

The reaction buffer should be free of extraneous amines and sulfhydryls. The pH of the reaction buffer should be 7.0-7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the lipophilic group chosen for reaction with maleimides, activated halogens, or pyridyl disulfides must contain a free sulfhydryl. Alternatively, a primary amine may be modified with to add a sulfhydryl In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5-7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing lipophilic group under the appropriate buffer conditions. The conjugates can be isolated from the reaction mixture by methods such as gel filtration or by dialysis.

Exemplary activated lipophilic moieties for conjugation include: N-(1-pyrene)maleimide; 2,5-dimethoxystilbene-4'-maleimide, eosin-5-maleimide; fluorescein-5-maleimide; N-(4-(6-dimethylamino-2-benzofuranyl)phenyl)maleimide; benzophenone-4-maleimide; 4-dimethylaminophenylazophenyl-4'-maleimide (DABMI), tetramethylrhodamine-5-maleimide, tetramethylrhodamine-6-maleimide, Rhodamine Red™ C2 maleimide, N-(5-aminopentyl)maleimide, trifluoroacetic acid salt, N-(2-aminoethyl)maleimide, trifluoroacetic acid salt, Oregon Green™ 488 maleimide, N-(2-((2-(((4-azido-2,3,5,6-tetrafluoro)benzoyl) amino)ethyl)dithio)ethyl) maleimide (TFPAM-SS 1), 2-(1-(3-dimethylaminopropyl)-indol-3-yl)-3-(indol-3-yl) maleimide (bisindolylmaleimide; GF 109203x), BODIPY® FL N-(2-aminoethyl)maleimide, N-(7-dimethylamino-4-methylcoumarin-3-yl)maleimide (DACM), Alexa™ 488 C5 maleimide, Alexa™ 594 C5 maleimide, sodium salt N-(1-pyrene)maleimide, 2,5-dimethoxystilbene-4'-maleimide, eosin-5-maleimide, fluorescein-5-maleimide, N-(4-(6-dimethylamino-2-benzofuranyl)phenyl) maleimide, benzophenone-4-maleimide, 4-dimethylaminophenylazophenyl-4'-maleimide, 1-(2-maleimidylethyl)-4-(5-(4-methoxyphenyl)oxazol-2-yl)pyridinium methanesulfonate, tetramethylrhodamine-5-maleimide, tetramethylrhodamine-6-maleimide, Rhodamine Red™ C2 maleimide, N-(5-aminopentyl)maleimide, N-(2-aminoethyl)maleimide, N-(2-((2-(((4-azido-2,3,5,6-tetrafluoro)benzoyl)amino)ethyl)dithio)ethyl)maleimide, 2-(1-(3-dimethylaminopropyl)-indol-3-yl)-3-(indol-3-yl) maleimide, N-(7-dimethylamino-4-methylcoumarin-3-yl)maleimide (DACM), 11H-Benzo[a]fluorene, Benzo[a]pyrene.

In one embodiment, the hedgehog polypeptide can be derivatived using pyrene maleimide, which can be purchased from Molecular Probes (Eugene, Oreg.), e.g., N-(1-pyrene) maleimide or 1-pyrenemethyl iodoacetate (PMIA ester).

For those embodiments wherein the hydrophobic moiety is a polypeptide, the modified hedgehog polypeptide of this invention can be constructed as a fusion protein, containing the hedgehog polypeptide and the hydrophobic moiety as one contiguous polypeptide chain.

In certain embodiments, the lipophilic moiety is an amphipathic polypeptide, such as magainin, cecropin, attacin, melittin, gramicidin S, alpha-toxin of Staph. aureus, alamethicin or a synthetic amphipathic polypeptide. Fusogenic coat proteins from viral particles can also be a convenient source of amphipathic sequences for the subject hedgehog proteins Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog agonist/antagonist is a polypeptide encodable by a nucleotide sequence that hybridizes under stringent conditions to a hedgehog coding sequence represented in one or more of SEQ ID NOs: 1-7. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous or identical, more preferably 70% homologous or identical, and most preferably 80% homologous or identical with an amino acid sequence selected from the group consisting of SEQ ID NOs: 8-14. Nucleic acids which encode polypeptides at least about 90%, more preferably at least about 95%, and most preferably at least about 98-99% homology or identity with an amino acid sequence represented in one of SEQ ID NOs: 8-14 are also within the scope of the invention.

In addition to native hedgehog proteins, hedgehog polypeptides preferred by the present invention are at least 60% homologous or identical, more preferably 70% homologous or identical and most preferably 80% homologous or identical with an amino acid sequence represented by any of SEQ ID NOs: 8-14. Polypeptides which are at least 90%, more preferably at least 95%, and most preferably at least about 98-99% homologous or identical with a sequence selected from the group consisting of SEQ ID NOs: 8-14 are also within the scope of the invention. The only prerequisite is that the hedgehog polypeptide is capable of modulating the growth state of T lymphocytes.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID NOs: 1-7.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169: 751-757) and *Salmonella typhimurium* and its in vitro activity has been demonstrated on recombinant proteins (Miller et al. (1987) *PNAS* 84: 2718-1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-5-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J Chromatography* 411: 177; and Janknecht et al. *PNAS* 88: 8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (SEQ ID NO: 31) (Pierschbacher et al. (1984) *Nature* 309: 30-3; and Kornblihtt et al. (1985) *EMBO* 4: 1755-9) can be added to the hedgehog polypeptide to support attachment of the chimeric molecule to a cell through binding ECM components (Ruoslahti et al. (1987) *Science* 238: 491-497; Pierschbacher et al. (1987) *J. Biol. Chem.* 262: 17294-8; Hynes (1987) *Cell* 48: 549-54; and Hynes (1992) *Cell* 69: 11-25).

In a preferred embodiment, the hedgehog polypeptide is isolated from, or is otherwise substantially free of, other cellular proteins, especially other extracellular or cell surface associated proteins which may normally be associated with the hedgehog polypeptide, unless provided in the form of fusion protein with the hedgehog polypeptide. The term "substantially free of other cellular or extracellular proteins" (also referred to herein as "contaminating proteins") or "substantially pure preparations" or "purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID NOs: 10-18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioactive fragments of hedgehog polypeptide, preferred hedgehog agonists/antagonists include at least 50 (contiguous) amino acid residues of a hedgehog polypeptide, more preferably at least 100 (contiguous), and even more preferably at least 150 (contiguous) residues.

Another preferred hedgehog polypeptide which can be included in the hedgehog agonist/antagonist is an N-terminal fragment of the mature protein having a molecular weight of approximately 19 kDa.

Preferred human hedgehog proteins include N-terminal fragments corresponding approximately to residues 24-197 of SEQ ID NO: 15, 28-202 of SEQ ID NO: 16, and 23-198 of SEQ ID NO: 17. By "corresponding approximately" it is meant that the sequence of interest is at most 20 amino acid residues different in length to the reference sequence, though more preferably at most 5, 10 or 15 amino acid different in length.

As described above for recombinant polypeptides, isolated hedgehog polypeptides can include all or a portion of the amino acid sequences represented in SEQ ID NO: 8, SEQ ID NO: 9, SEQ ID NO: 10, SEQ ID NO: 11, SEQ ID NO: 12, SEQ ID NO: 13 or SEQ ID NO: 14, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

Still other preferred hedgehog polypeptides includes an amino acid sequence represented by the formula A-B wherein: (i) A represents all or the portion of the amino acid sequence designated by residues 1-168 of SEQ ID NO: 21; and B represents at least one amino acid residue of the amino acid sequence designated by residues 169-221 of SEQ ID NO: 21; (ii) A represents all or the portion of the amino acid sequence designated by residues 24-193 of SEQ ID NO: 15; and B represents at least one amino acid residue of the amino acid sequence designated by residues 194-250 of SEQ ID NO: 15; (iii) A represents all or the portion of the amino acid sequence designated by residues 25-193 of SEQ ID NO: 13; and B represents at least one amino acid residue of the amino acid sequence designated by residues 194-250 of SEQ ID NO: 13; (iv) A represents all or the portion of the amino acid sequence designated by residues 23-193 of SEQ ID NO: 11; and B represents at least one amino acid residue of the amino acid sequence designated by residues 194-250 of SEQ ID NO: 11; (v) A represents all or the portion of the amino acid sequence designated by residues 28-197 of SEQ ID NO: 12; and B represents at least one amino acid residue of the amino acid sequence designated by residues 198-250 of SEQ ID NO: 12; (vi) A represents all or the portion of the amino acid sequence designated by residues 29-197 of SEQ ID NO: 16; and B represents at least one amino acid residue of the amino acid sequence designated by residues 198-250 of SEQ ID NO: 16; or (vii) A represents all or the portion of the amino acid sequence designated by residues 23-193 of SEQ ID NO: 17, and B represents at least one amino acid residue of the amino acid sequence designated by residues 194-250 of SEQ ID NO: 17. In certain preferred embodiments, A and B together represent a contiguous polypeptide sequence designated sequence, A represents at least 25, 50, 75, 100, 125 or 150 (contiguous) amino acids of the designated sequence, and B represents at least 5, 10, or 20 (contiguous) amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above. In preferred embodiments, the hedgehog polypeptide includes a C-terminal glycine (or other appropriate residue) which is derivatized with a cholesterol.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Roman et al. (1994) *Eur J Biochem* 222: 65-73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that one could reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37: 1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193: 653, and Bass et al. (1990) *Proteins: Structure, Function and Genetics* 8: 309-314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

```
                                          (SEQ ID NO: 21)
C-G-P-G-R-G-X(1)-G-X(2)-R-R-H-P-K-K-L-T-P-L-A-Y-K-

Q-F-I-P-N-V-A-E-K-T-L-G-A-S-G-R-Y-E-G-K-I-X(3)-R-

N-S-E-R-F-K-E-L-T-P-N-Y-N-P-D-I-I-F-K-D-E-E-N-T-G-

A-D-R-L-M-T-Q-R-C-K-D-K-L-N-X(4)-L-A-I-S-V-M-N-

X(5)-W-P-G-V-X(6)-L-R-V-T-E-G-W-D-E-D-G-H-H-X(7)-

E-E-S-L-H-Y-E-G-R-A-V-D-I-T-T-S-D-R-D-X(8)-S-K-Y-

G-X(9)-L-X(10)-R-L-A-V-E-A-G-F-D-W-V-Y-Y-E-S-K-A-

H-I-H-C-S-V-K-A-E-N-S-V-A-A-K-S-G-G-C-F-P-G-S-A-

X(11)-V-X(12)-L-X(13)-X(14)-G-G-X(15)-K-X-(16)-V-
K-D-L-X(17)-P-G-D-X(18)-V-L-A-A-D-X(19)-X(20)-G-
X(21)-L-X(22)-X(23)-S-D-F-X(24)-X(25)-F-X(26)-D-R
``` wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gln, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gln, Ser, Thr or Cys; Xaa(18) represents Arg, Lys, Met or Ile; Xaa(19) represents Ala, Gly, Cys, Asp, Glu, Gln, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22) represent Leu, Val, Met or Ile; Xaa(23) represents Phe, Tyr, Thr, His or Trp; Xaa(24) represents Ile, Val, Leu or Met; Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

(SEQ ID No: 22)
C-G-P-G-R-G-X(1)-X(2)-X(3)-R-R-X(4)-X(5)-X(6)-P-K-X(7)-L-X(8)-P-L-X(9)-Y-K-Q-F-X(10)-P-X(11)-X(12)-X(13)-E-X(14)-T-L-G-A-S-G-X(15)-X(16)-E-G-X(17)-X(18)-X(19)-R-X(20)-S-E-R-F-X(21)-X(22)-L-T-P-N-Y-N-P-D-I-I-F-K-D-E-E-N-X(23)-G-A-D-R-L-M-T-X(24)-R-C-K-X(25)-X(26)-X(27)-N-X(28)-L-A-I-S-V-M-N-X(29)-W-P-G-V-X(30)-L-R-V-T-E-G-X(31)-D-E-D-G-H-H-X(32)-X(33)-X(34)-S-L-H-Y-E-G-R-A-X(35)-D-I-T-T-S-D-R-D-X(36)-X(37)-K-Y-G-X(38)-L-X(39)-R-L-A-V-E-A-G-F-D-W-V-Y-Y-E-S-X(40)-X(41)-H-X(42)-H-X(43)-S-V-K-X(44)-X(45)

wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa (21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) *Tetrahedron* 39: 3; Itakura et al. (1981) *Recombinant DNA, Proc 3rd Cleveland Sympos. Macromolecules*, ed. AG Walton, Amsterdam: Elsevier pp 273-289; Itakura et al. (1984) *Annu. Rev. Biochem.* 53: 323; Itakura et al. (1984) *Science* 198: 1056; Ike et al. (1983) *Nucleic Acid Res.* 11: 477. Such techniques have been employed in the directed evolution of other proteins (see, for example, Scott et al. (1990) *Science* 249: 386-390; Roberts et al. (1992) *PNAS* 89: 2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with peripheral nerve cells. A functional hedgehog protein secreted by the cells expressing the combinatorial library will diffuse to neighboring T lymphocytes and induce a particular biological response, such as proliferation or differentiation. The pattern of detection of such a change in phenotype will resemble a gradient function, and will allow the isolation (generally after several repetitive rounds of selection) of cells producing hedgehog homologs active as neurotrophic agents. Likewise, hedgehog antagonists can be selected in similar fashion by the ability of the cell producing a functional antagonist to protect neighboring cells (e.g., to inhibit proliferation) from the effect of wild-type hedgehog added to the culture media.

To illustrate, target T lymphocytes are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as growth state, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) Bio/Technology 9: 1370-1371; and Goward et al. (1992) TIBS 18: 136-140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267: 16007-16010; Griffths et al. (1993) EMBO J. 12: 725-734; Clackson et al. (1991) Nature 352: 624-628; and Barbas et al. (1992) PNAS 89: 4457-4461).

In an illustrative embodiment, the recombinant phage antibody system (RPAS, Pharamacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89: 7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3): 327-331).

The invention also provides for reduction of the hedgehog protein to generate mimetics, e.g. peptide or non-peptide agents, which are able to disrupt binding of a hedgehog polypeptide of the present invention with an hedgehog receptor. Thus, such mutagenic techniques as described above are also useful to map the determinants of the hedgehog proteins which participate in protein-protein interactions involved in, for example, binding of the subject hedgehog polypeptide to other extracellular matrix components. To illustrate, the critical residues of a subject hedgehog polypeptide which are involved in molecular recognition of an hedgehog receptor such as patched can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29: 295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26: 647; and Sato et al. (1986) J Chem Soc Perkin Trans 1: 1231), and β-aminoalcohols (Gordon et al. (1985) Biochem Biophys Res Commun 126: 419; and Dann et al. (1986) Biochem Biophys Res Commun 134: 71).

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo transfection of a hedgehog polypeptide in particular cell types so as cause ectopic expression of a hedgehog polypeptide in an T lymphocytes or other cells associated therewith.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76: 271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including T lymphocytes, in vitro and/or in vivo (see for example Eglitis, et al. (1985) *Science* 230: 1395-1398; Danos and Mulligan (1988) *Proc. Natl. Acad. Sci. USA* 85: 6460-6464; Wilson et al. (1988) *Proc. Natl. Acad. Sci. USA* 85: 3014-3018; Armentano et al. (1990) *Proc. Natl. Acad. Sci. USA* 87: 6141-6145; Huber et al. (1991) *Proc. Natl. Acad. Sci. USA* 88: 8039-8043; Ferry et al. (1991) *Proc. Natl. Acad. Sci. USA* 88: 8377-8381; Chowdhury et al. (1991) *Science* 254: 1802-1805; van Beusechem et al. (1992) *Proc. Natl. Acad. Sci. USA* 89: 7640-7644; Kay et al. (1992) *Human Gene Therapy* 3: 641-647; Dai et al. (1992) *Proc. Natl. Acad. Sci. USA* 89: 10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86: 9079-9083; Julan et al. (1992) *J Gen Virol* 73: 3251-3255; and Goud et al. (1983) *Virology* 163: 251-254); or coupling cell surface receptor ligands to the viral env proteins (Neda et al. (1991) *J Biol Chem* 266: 14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6: 616;

Rosenfeld et al. (1991) *Science* 252: 431-434; and Rosenfeld et al. (1992) *Cell* 68: 143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including T lymphocytes. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57: 267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16: 683; Berkner et al., supra; and Graham et al. in Methods in *Molecular Biology*, E. J. Murray, Ed. (Humana, Clifton, N.J., 1991) vol. 7. pp. 109-127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057). A hedgehog expression construct can be delivered in a gene therapy construct to dermal cells by, e.g., electroporation using techniques described, for example, by Dev et al. ((1994) *Cancer Treat Rev* 20: 105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the hedgehog or ptc agonist/antagonist can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes constitutive expression of the hedgehog gene or which causes inducible expression of the gene under conditions different from the normal expression pattern of the gene. Other genes in the patched signaling pathway can be similarly targeted. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequence(s) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J. Exp. Med.*, 169: 13), the human β-actin promoter (Gunning et al. (1987) *PNAS* 84: 4831-4835), the glucocorticoid-inducible promoter present in the mouse mammary tumor virus long terminal repeat (MMTV LTR) (Klessig et al. (1984) *Mol. Cell Biol.* 4: 1354-1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bemoist et al. (1981) *Nature* 290: 304-310; Templeton et al. (1984) *Mol. Cell Biol.*, 4: 817; and Sprague et al. (1983) *J. Virol.*, 45: 773), the promoter contained in the 3' long terminal repeat of Rous sarcoma virus (RSV) (Yamamoto et al., 1980, *Cell*, 22: 787-797), the herpes simplex virus (HSV) thymidine kinase promoter/enhancer (Wagner et al. (1981) *PNAS* 82: 3567-71), and the herpes simplex virus LAT promoter (Wolfe et al. (1992) *Nature Genetics*, 1: 379-384).

In an exemplary embodiment, portions of the 5' flanking region of the human Shh gene are amplified using primers which add restriction sites, to generate the following fragments

```
5'-gcgcgcttcgaaGCGAGGCAGCCAGCGAGGGAGAGAGCGAGCGGGCGAGCCGGAGC-
GAGGAAatcgatgcgcgc (primer 1) (SEQ ID NO: 23)

5'-gcgcgcagatctGGGAAAGCGCAAGAGAGAGCGCACACGCACACACCCGCCGCGCG-
CACTCGggatccgcgcgc (primer 2) (SEQ ID NO: 24)
```

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pcDNA1.1 (Invitrogen) includes a CMV promoter. The plasmid is cut with with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, a cut with AsuII and BamHI to produce the gene activation construct the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

After having determined which amino acid residues contribute to the receptor-binding domain, synthetic peptides may be designed that have amino acid sequences that define a pre-selected receptor-binding motif. A computer program useful in designing potentially bioactive peptidomimetics is described in U.S. Pat. No. 5,331,573, the disclosure of which is incorporated by reference herein. To design HH antagonists, one may preserve the receptor-binding motif so that the mutant proteins would bind to the receptor but not invoke Hh signaling.

In addition to choosing a desirable amino acid sequence, if necessary, a skilled artisan using standard molecular modeling software packages, can design specific peptides having, for example, additional cysteine amino acids located at pre-selected positions to facilitate cyclization of the peptide of interest. Oxidation of the additional cysteine residues results in cyclization of the peptide thereby constraining the peptide in a conformation that mimics the conformation of the corresponding amino acid sequence in the native protein. It is contemplated, that any standard covalent linkage, for example, disulfide bonds, typically used to cyclize synthetic

```
cgaagcgaggcagccagcgagggagagagcgagcgggcgagccggagcgaggaaATCGAAGGTTC

GAATCCTTCCCCCACCACCATCACTTTCAAAAGTCCGAAAGAATCTGCTCCCTGCTTGTGTGTTG

GAGGTCGCTGAGTAGTGCGCGAGTAAAATTTAAGCTACAACAAGGCAAGGCTTGACCGACAATTG

CATGAAGAATCTGCTTAGGGTTAGGCGTTTTGCGCTGCTTCGCGATGTACGGGCCAGATATACGC

GTTGACATTGATTATTGACTAGTTATTAATAGTAATCAATTACGGGGTCATTAGTTCATAGCCCA

TATATGGAGTTCCGCGTTACATAACTTACGGTAAATGGCCCGCCTGGCTGACCGCCCAACGACCC

CCGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCCA

AGTACGCCCCCTATTGACGTCAATGACGGTAAATGGCCCGCCTGGCATTATGCCCAGTACATGAC

CTTATGGGACTTTCCTACTTGGCAGTACATCTACGTATTAGTCATCGCTATTACCATGGTGATGC

GGTTTTGGCAGTACATCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAAAATGTCGTAA

CAACTCCGCCCCATTGACGCAAATGGGCGGTAGGCGTGTACGGTGGGAGGTCTATATAAGCAGAG

CTCTCTGGCTAACTAGAGAACCCACTGCTTACTGGCTTATCGAAATTAATACGACTCACTATAGG

GAGACCCAAGCTTGGTACCGAGCTCGGATCgatctgggaaagcgcaagagagagcgcacacgcac acacccgccgcgcgcactcgg (SEQ ID NO: 25)
```

In this construct, the flanking primer 1 and primer 2 sequences provide the recombination region which permits peptides may be useful in the practice of the instant invention. Alternative cyclization chemistries are discussed in International Application PCT/WO 95/01800, the disclosure of which is incorporated herein by reference.

Alternatively, analogs which are small peptides, usually up to 50 amino acids in length, may be synthesized using standard solid-phase peptide synthesis procedures, for example, procedures similar to those described in Merrifield (1963) *J. Am. Chem. Soc.*, 85:2149. Polypeptides are now routinely synthesized by automated synthesizing apparatuses. See, for example, a review by Veggeberg (1995) *The Scientist* 9[2]:17. Details of appropriate chemistries, resins, protecting groups, protected amino acids and reagents are well known in the art and so are not discussed in detail herein. See, for example, Atherton et al. (1963) Solid Phase Peptide Synthesis: A Practical Approach (IRL Press), and Bodanszky (1993) Peptide Chemistry, A Practical Textbook, 2nd Ed., Springer-Verlag, and Fields et al. (1990) *Int. J. Peptide Protein Res.* 35:161-214, the disclosures of which are incorporated herein by reference.

The dose or therapeutically effective amount of the hedgehog therapeutic agents to be delivered depends on the specific use. In the fetal thymic organ culture (FTOC), if Shh concentration is more than 0.1 μg/ml, especially more than 0.5 μg/ml, Hedgehog functions as an immunosuppressant (see FIG. 12B). In contrast, if the HH concentration is between 0.00005 and 0.05 μg/ml, especially between 0.0005 and 0.005 μg/ml, Hedgehog functions to enhance T cell development (immunostimulant). However, when Hedgehog level drops below 0.00005 μg/ml, not sufficient HH signaling can be maintained for T cell development.

Based on this model, to exploit the Hedgehog pathway for immuno-suppression, either high level of HH protein (or HH agonist that could induce similar high levels of HH protein, at least in thymus), or high dose of HH antagonist can be used. Here, high level of HH protein or HH agonist is expected to produce the level of HH signaling equivalent to that produced by about 0.5 μg/ml of HH peptide in thymus; high level of HH antagonist is equivalent to the level of antagonist that is capable of dropping HH signaling to below the level equivalent to that produced by about 0.00005 μg/ml of HH protein in thymus (the concentration that is below the threshold level required for normal T cell development).

Similarly, to exploit the Hedgehog pathway for immunostimulation, either appropriate levels of HH protein, or HH agonist, may be used to achieve HH signaling equivalent to that level by about 0.0005-0.005 μg/ml of HH peptide. Alternatively, in patients with high endogenous level of HH expression, appropriate amount of HH antagonists may be used to down-regulate the active HH signaling to below that minimal level required to promote T cell development (e.g., about 0.00005 μg/ml in thymus).

The exact dose of the compounds and compositions of the invention (HH antagonists and agonists) may be administered by any suitable route, and the person skilled in the art will readily be able to determine the most suitable route and dose for the condition to be treated, depends on a number of factors. Dosage will be at the discretion of the attendant physician or veterinarian, based on the guideline provided, and will depend on the nature and state of the condition to be treated, the age, gender, weight class, and general state of health of the subject to be treated, the route of administration, the nature of the agonist/antagonist used, and any previous treatment which may have been administered.

For example, to determine the proper dose of hedgehog agonist or antagonist for a mammal of a specific age, gender, weight class, etc., different dosages of agonist or antagonists may be administered, either systematically or locally. Results from these different treatment groups would tend to show that at certain threshold dose, the host T cell response would be enhanced/suppressed. These data may be used to build a database, which is useful as a general guidance for future use in patients of different age, gender, weight class, and physical conditions, etc.

The mammal to be treated may be a human, or may be a domestic or companion animal. While it is particularly contemplated that the compounds of the invention are suitable for use in medical treatment of humans, they are also applicable to veterinary treatment, including treatment of companion animals such as dogs and cats, and domestic animals such as horses, cattle and sheep, or zoo animals such as non-human primates, felids, canids, bovids, and ungulates. The carrier or diluent, and other excipients, will depend on the route of administration, and again the person skilled in the art will readily be able to determine the most suitable formulation for each particular use.

The same approach can be adapted to determine the appropriate dose for any of the following HH agonists, antagonists.

It will be clearly understood that the method of the invention may be used in conjunction with one or more other treatments, such as other therapeutic agents.

Small Molecule Agonists of HH Pathway

As described in further detail below, it is contemplated that the subject methods can be carried out using a variety of different small molecules which can be readily identified, for example, by such drug screening assays as described herein. For example, compounds useful in the subject methods include compounds represented by general formula (I):

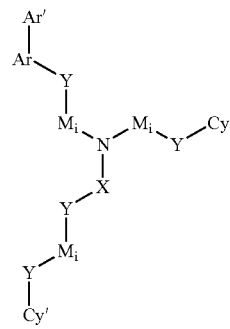

Formula I wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S(O$_2$)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p and n, individually for each occurrence, represent integers from 0 to 10, preferably from 0 to 5.

In certain embodiments, compounds useful in the present invention may be represented by general formula (II):

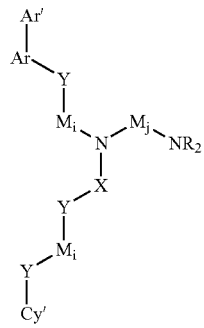

Formula II wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne, wherein some or all occurrences of M in $M_j$ form all or part of a cyclic structure;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or NR$_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(═O)—, —C(═S)—, and —S($O_2$)—.

In certain embodiments, R represents H or lower alkyl, e.g., H or Me.

In certain embodiments, $NR_2$ represents a primary amine or a secondary or tertiary amine substituted with one or two lower alkyl groups, aryl groups, or aralkyl groups, respectively, preferably a primary amine or secondary amine.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N$(R)_2$, —$(CH_2)_p$NR-lower alkyl, —$(CH_2)_p$NR-lower alkenyl, —NR$(CH_2)_n$R, and protected forms of the above, wherein p and n, individually for each occurrence, represent integers from 0 to 10, preferably from 0 to 5.

In certain embodiments, compounds useful in the present invention may be represented by general formula (III):

Formula III

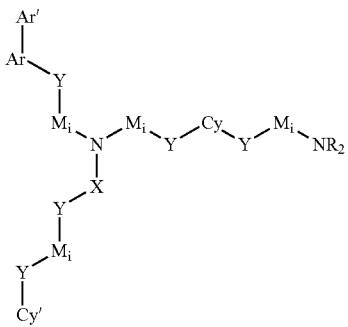

wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(═O)—, —C(═S)—, —S($O_2$)—, —S(O)—, —C(═NCN)—, —P(═O)(OR)—, and a methylene group optionally substituted with 1-2 groups such as lower alkyl, alkenyl, or alkynyl groups;

M represents, independently for each occurrence, a substituted or unsubstituted methylene group, such as —$CH_2$—, —CHF—, —CHOH—, —CH(Me)—, —C(═O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —$CH_2$—, —CHF—, —CHOH—, —CH(Me)—, —C(═O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or $NR_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S(O₂)—.

In certain embodiments, R represents H or lower alkyl, e.g., H or Me.

In certain embodiments, NR₂ represents a primary amine or a secondary or tertiary amine substituted with one or two lower alkyl groups, aryl groups, or aralkyl groups, respectively, preferably a primary amine or a secondary amine.

In certain embodiments, Cy represents a substituted or unsubstituted non-aromatic carbocyclic or heterocyclic ring, i.e., including at least one sp³ hybridized atom, and preferably a plurality of sp³ hybridized atoms. In certain embodiments, Cy is directly attached to N and/or to NR₂. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH₂)$_p$alkyl, —(CH₂)$_p$alkenyl, —(CH₂)$_p$alkynyl, —(CH₂)$_p$aryl, —(CH₂)$_p$aralkyl, —(CH₂)$_p$OH, —(CH₂)$_p$O-lower alkyl, —(CH₂)$_p$O-lower alkenyl, —O(CH₂)$_n$R, —(CH₂)$_p$SH, —(CH₂)$_p$S-lower alkyl, —(CH₂)$_p$S-lower alkenyl, —S(CH₂)$_n$R, —(CH₂)$_p$N(R)₂, —(CH₂)$_p$NR-lower alkyl, —(CH₂)$_p$NR-lower alkenyl, —NR(CH₂)$_n$R, and protected forms of the above, wherein n and p, individually for each occurrence, represent integers from 0 to 10, preferably from 0 to 5.

In certain embodiments, compounds useful in the subject methods include compounds represented by general formula (IV):

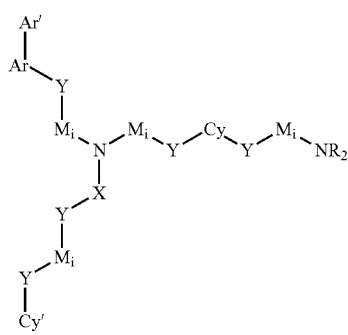

Formula IV wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O₂)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH₂—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R₁ and R₂ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH₂)$_p$alkyl, —(CH₂)$_p$alkenyl, —(CH₂)$_p$alkynyl, —(CH₂)$_p$aryl, —(CH₂)$_p$aralkyl, —(CH₂)$_p$OH, —(CH₂)$_p$O-lower alkyl, —(CH₂)$_p$O-lower alkenyl, —O(CH₂)$_n$R, —(CH₂)$_p$SH, —(CH₂)$_p$S-lower alkyl, —(CH₂)$_p$S-lower alkenyl, —S(CH₂)$_n$R, —(CH₂)$_p$N(R)₂, —(CH₂)$_p$NR-lower alkyl, —(CH₂)$_p$NR-lower alkenyl, —NR(CH₂)$_n$R, and protected forms of the above;

Cy represents substituted or unsubstituted aryl, heterocyclyl, heteroaryl, or cycloalkyl, including polycyclic groups;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH₂—, —CHF—, —CHOH—, —CH(Me)—, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl₂ and CF₃), and ethyl (e.g., including haloethyl, such as CH₂CCl₃, C₂F₅, etc.), preferably from halogen and methyl (e.g., including halomethyl, such as CHCl₂ and CF₃). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N.

In certain embodiments, X is selected from —C(=O)—, —C(=S)—, and —S(O₂)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp³ hybridized atom, and preferably a plurality of sp³ hybridized atoms. In certain embodiments, Cy is directly attached to N. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)_2$, —$(CH_2)_p$NR-lower alkyl, —$(CH_2)_p$NR-lower alkenyl, —$NR(CH_2)_n$R, and protected forms of the above.

In certain embodiments, compounds useful in the present invention may be represented by general formula (V):

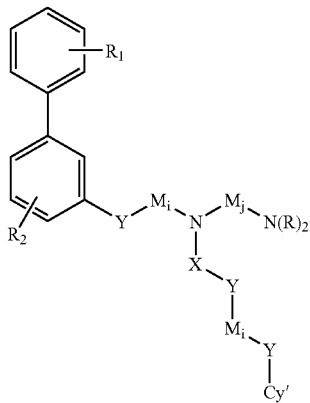

Formula V wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O_2)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —$CH_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)_2$, —$(CH_2)_p$NR-lower alkyl, —$(CH_2)_p$NR-lower alkenyl, —$NR(CH_2)_n$R, and protected forms of the above;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —$CH_2$—, —CHF—, —CHOH—, —CH(Me)—, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or $NR_2$.

In certain embodiments, X is selected from —C(=O)—, —C(=S)—, and —S(O_2)—.

In certain embodiments, $NR_2$ represents a primary amine or a secondary or tertiary amine substituted with one or two lower alkyl groups, aryl groups, or aralkyl groups, respectively, preferably a primary or secondary amine.

In certain embodiments, R represents H or lower alkyl, e.g., H or Me.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, compounds useful in the present invention may be represented by general formula (VI):

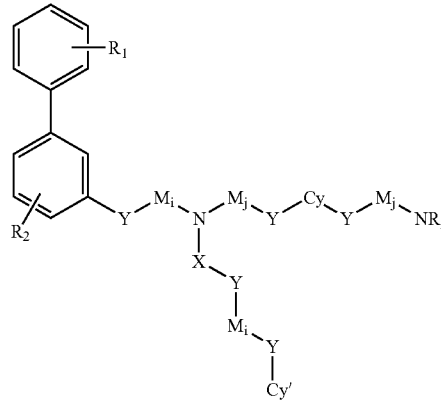

Formula VI wherein, as valence and stability permit,

Cy' represents a substituted or unsubstituted aryl or heteroaryl ring, including polycyclics; Y, independently for each occurrence, is absent or represents —N(R)—, —O—, —S—, or —Se—;

X is selected from —C(═O)—, —C(═S)—, —S(O$_2$)—, —S(O)—, —C(═NCN)—, —P(═O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(═O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy represents substituted or unsubstituted aryl, heterocyclyl, heteroaryl, or cycloalkyl, including polycyclic groups;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

i represents, independently for each occurrence, an integer from 0 to 5, preferably from 0 to 2; and n and p, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(═O)—, etc.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, X is selected from —C(═O)—, —C(═S)—, and —S(O$_2$)—.

In certain embodiments, —NR$_2$ represents a primary amine or a secondary or tertiary amine substituted with one or two lower alkyl groups, aryl groups, or aralkyl groups, respectively, preferably a primary amine.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N and/or to NR$_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, a subject compound has the structure of Formula VII:

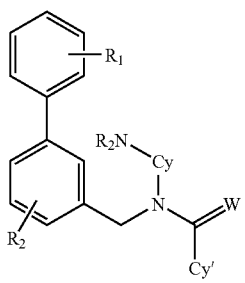

Formula VII wherein, as valence and stability permit,

Cy represents a substituted or unsubstituted heterocyclyl or cycloalkyl;

Cy' is a substituted or unsubstituted aryl or heteroaryl ring, including polycyclics;

W is O or S;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N(R)$_2$, —$(CH_2)_p$NR-lower alkyl, —$(CH_2)_p$NR-lower alkenyl, —NR$(CH_2)_n$R, and protected forms of the above;

n and p, individually for each occurrence, represent integers from 0 to 10, preferably from 0 to 5.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain other embodiments, Cy' represents an aryl or heteroaryl ring substituted at least with a substituted or unsubstituted aryl or heteroaryl ring, i.e., to form a biaryl ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, $NR_2$ represents a primary amine or a secondary or tertiary amine substituted with one or two lower alkyl groups, aryl groups, or aralkyl groups, respectively, preferably a primary or secondary amine.

In certain embodiments, Cy represents a substituted or unsubstituted saturated carbocyclic or heterocyclic ring, i.e., composed of a plurality of sp$^3$ hybridized atoms. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N(R)$_2$, —$(CH_2)_p$NR-lower alkyl, —$(CH_2)_p$NR-lower alkenyl, —NR$(CH_2)_n$R, and protected forms of the above.

In certain embodiments, a subject compound has a structure of Formula VIII:

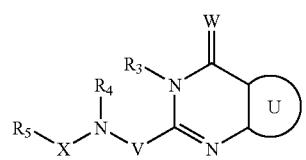

Formula VIII wherein, as valence and stability permit,

U represents a substituted or unsubstituted aryl or heteroaryl ring fused to the nitrogen-containing ring;

V represents a lower alkylene group, such as methylene, 1,2-ethylene, 1,1-ethylene, 1,1-propylene, 1,2-propylene, 1,3-propylene, etc.;

W represents S or O, preferably O;

X represents C=O, C=S, or SO$_2$;

$R_3$ represents substituted or unsubstituted aryl, heteroaryl, lower alkyl, lower alkenyl, lower alkynyl, carbocyclyl, carbocyclylalkyl, heterocyclyl, heterocyclylalkyl, aralkyl, or heteroaralkyl;

$R_4$ represents substituted or unsubstituted aralkyl or lower alkyl, such as phenethyl, benzyl, or aminoalkyl, etc.;

$R_5$ represents substituted or unsubstituted aryl, heteroaryl, aralkyl, or heteroaralkyl, including polycyclic aromatic or heteroaromatic groups.

In certain embodiments, U represents a phenyl ring fused to the nitrogen-containing ring.

In certain embodiments, $R_3$ is selected from substituted or unsubstituted aryl, heteroaryl, lower alkyl, lower alkenyl, aralkyl, and heteroaralkyl.

In certain embodiments, $R_4$ is an unsubstituted lower alkyl group, or is a lower alkyl group substituted with a secondary or tertiary amine.

In certain embodiments, $R_5$ is selected from substituted or unsubstituted phenyl or naphthyl, or is a diarylalkyl group, such as 2,2-diphenylethyl, diphenylmethyl, etc.

In embodiments, subject compounds include compounds represented by general formula (IX):

Formula IX

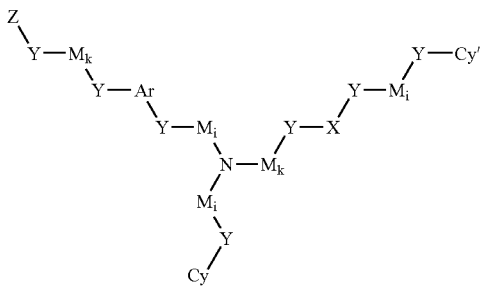

wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups;

i represents, independently for each occurrence, an integer from 0 to 5, preferably from 0 to 2; and k represents an integer from 0 to 3, preferably from 0 to 2.

In certain embodiments, M represents, independently for each occurrence, a substituted or unsubstituted methylene group, such as —CH$_2$—, —CHF—, —CHOH—, —CH(Me)—, —C(=O)—, etc. In certain embodiments, i represents 0 for all occurrences except in the sequence N-M$_i$-Y—Ar, where i represents 1.

In certain embodiments, Ar and X independently represent substituted or unsubstituted aryl or heteroaryl rings, e.g., unsubstituted or substituted with one or more groups optionally including heteroatoms such as O, N, and S. In certain embodiments, Ar represents a phenyl ring. In certain embodiments, at least one of Ar represents a heteroaryl ring, e.g., a pyridyl, thiazolyl, thienyl, pyrimidyl, furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to M$_k$. In embodiments wherein Y is present in a position, i or k preferably represents 2 in an adjacent M$_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S(O$_2$)—.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)nR, —(CH$_2$)$_p$SH, —(CH$_2$)$_p$S-lower alkyl, —(CH$_2$)$_p$S-lower alkenyl, —S(CH$_2$)$_n$ R, —(CH$_2$)$_p$N(R)$_2$, —(CH$_2$)$_p$NR-lower alkyl, —(CH$_2$)$_p$ NR-lower alkenyl, —NR(CH$_2$)$_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (X):

Formula X

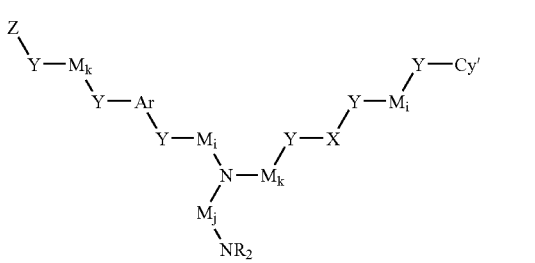

wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne, wherein some or all occurrences of M in M$_j$ form all or part of a cyclic structure;

j represents, independently for each occurrence, an integer from 2 to 10, preferably from 2 to 7;

i represents, independently for each occurrence, an integer from 0 to 5, preferably from 0 to 2; and k represents an integer from 0 to 3, preferably from 0 to 2.

In certain embodiments, NR$_2$ represents a primary amine or a secondary or tertiary amine substituted with one or two lower alkyl groups, aryl groups, or aralkyl groups, respectively, preferably a primary or secondary amine.

In certain embodiments, M represents, independently for each occurrence, a substituted or unsubstituted methylene group, such as —CH$_2$—, —CHF—, —CHOH—, —CH(Me)—, —C(=O)—, etc. In certain embodiments, i represents 0 for all occurrences except in the sequence N-M$_i$-Y—Ar, where i represents 1.

In certain embodiments, Ar and X independently represent substituted or unsubstituted aryl or heteroaryl rings, e.g., unsubstituted or substituted with one or more groups optionally including heteroatoms such as O, N, and S. In certain embodiments, Ar represents a phenyl ring. In certain embodiments, Ar represents a heteroaryl ring, e.g., a pyridyl, thiazolyl, thienyl, pyrimidyl, furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to M$_k$. In embodiments wherein Y is present in a position, i or k preferably represents 2 in an adjacent M$_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S(O$_2$)—.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)nR, —(CH$_2$)$_p$SH, —(CH$_2$)$_p$S-lower alkyl, —(CH$_2$)$_p$S-lower alkenyl, —S(CH$_2$)$_n$ R, —(CH$_2$)$_p$N(R)$_2$, —(CH$_2$)$_p$NR-lower alkyl, —(CH$_2$)$_p$ R-lower alkenyl, —NR(CH$_2$)$_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (XI):

Formula XI

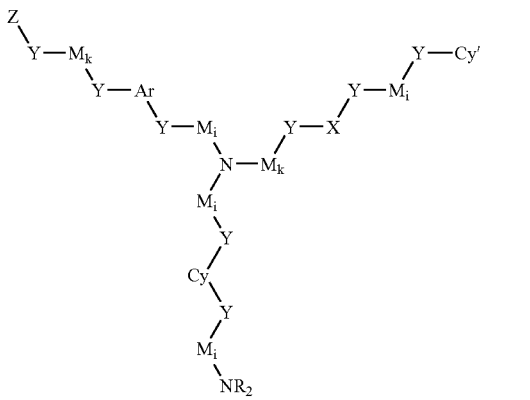

wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups;

i represents, independently for each occurrence, an integer from 0 to 5, preferably from 0 to 2; and k represents an integer from 0 to 3, preferably from 0 to 2.

In certain embodiments, NR$_2$ represents a primary amine or a secondary or tertiary amine substituted with one or two lower alkyl groups, aryl groups, or aralkyl groups, respectively, preferably a primary or secondary amine.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Z independently represent substituted or unsubstituted aryl or heteroaryl rings, e.g., unsubstituted or substituted with one or more groups optionally including heteroatoms such as O, N, and S. In certain embodiments, at least one of Ar and Z represents a phenyl ring. In certain embodiments, at least one of Ar and Z represents a heteroaryl ring, e.g., a pyridyl, thiazolyl, thienyl, pyrimidyl, furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to M$_k$. In embodiments wherein Y is present in a position, i or k preferably represents 2 in an adjacent M$_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is a 5- to 7-membered ring. In certain embodiments, Cy is directly attached to N and/or to NR$_2$. In embodiments wherein Cy is a six-membered ring directly attached to N and bears an amino substituent at the 4 position of the ring relative to N, the N and amine substituents may be disposed trans on the ring.

In certain embodiments, X is selected from —C(=O)—, —C(=S)—, and —S(O$_2$)—.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (XII):

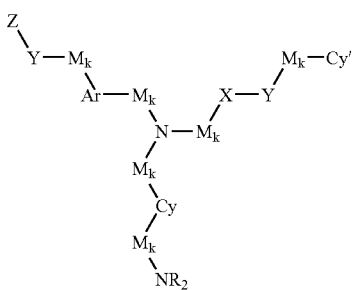

Formula XII wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R, independently for each occurrence, represents H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl;

Cy and Cy' independently represent substituted or unsubstituted aryl, heterocyclyl, heteroaryl, or cycloalkyl, including polycyclic groups; and k represents an integer from 0 to 1.

In certain embodiments, NR$_2$ represents a primary amine or a secondary or tertiary amine substituted with one or two lower alkyl groups, respectively, preferably a primary or secondary amine, most preferably a secondary amine.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Y is absent from all positions. In certain embodiments, where Y is adjacent to M$_k$, either Y is absent or k=0. In certain embodiments, for at least one occurrence of M$_k$ attached to Cy, k=0, optionally for both occurrences. In certain embodiments, for M$_k$ attached to Ar and N, k=1.

In certain embodiments, Ar and Z independently represent substituted or unsubstituted aryl or heteroaryl rings, e.g., unsubstituted or substituted with one or more groups optionally including heteroatoms such as O, N, and S. In certain embodiments, at least one of Ar and Z represents a phenyl ring. In certain embodiments, at least one of Ar and Z represents a heteroaryl ring, e.g., a pyridyl, thiazolyl, thienyl, pyrimidyl, furanyl, etc. In certain embodiments, the occurrences of M$_k$ attached to Ar are disposed in a meta and/or 1,3-relationship.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo(b)thien-2-yl, preferably a 3-chloro-benzo(b)thien-2-yl, 3-fluoro-benzo(b)thien-2-yl, or 3-methyl-benzo(b)thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo(b)thien-2-yl, or 3-methyl-benzo(b)thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is a 5- to 7-membered ring. In certain embodiments, Cy is directly attached to N and/or to NR$_2$. In embodiments wherein Cy is a six-membered ring directly attached to N and bears an amino substituent at the 4 position of the ring relative to N, the N and amino substituents may be disposed trans on the ring.

In certain embodiments, X is selected from —C(=O)—, —C(=S)—, and —S(O$_2$)—.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, the subject agonists can be chosen on the basis of their selectively for the hedgehog pathway. This selectivity can be for the hedgehog pathway versus other pathways, or for selectivity between particular hedgehog pathways, e.g., ptc-1, ptc-2, etc.

In certain preferred embodiments, the subject agonists modulate ptc-smo mediated signal transduction with an ED$_{50}$ of 1 mM or less, more preferably of 1 µM or less, and even more preferably of 1 nM or less. For hedgehog-dependent agonists, the subject agonists increase the activity of hedgehog 10-fold, 100-fold, or even 1000-fold.

In particular embodiments, the small molecule is chosen for use because it is more selective for one patched isoform over the next, e.g., 10-fold, and more preferably at least 100- or even 1000-fold more selective for one patched pathway (ptc-1, ptc-2) over another.

In certain embodiments, a compound which is an agonist of the hedgehog pathway is chosen to selectively agonize hedgehog activity over protein kinases other than PKA, such as PKC, e.g., the compound modulates the activity of the PKA/hedgehog pathway at least an order of magnitude more strongly than it modulates the activity of another protein kinase, preferably at least two orders of magnitude more strongly, even more preferably at least three orders of magnitude more strongly. Thus, for example, a preferred activator of the hedgehog pathway may activate hedgehog activity with a $K_i$ at least an order of magnitude lower than its $K_i$ for activation of PKC, preferably at least two orders of magnitude lower, even more preferably at least three orders of magnitude lower. In certain embodiments, the $K_i$ for PKA/hedgehog activation is less than 10 nM, preferably less than 1 nM, even more preferably less than 0.1 nM.

Antibodies as HH Agonists

In one embodiment of the invention described herein, the agent to stimulate the Hh signaling pathway is an antibody or fragment thereof.

One embodiment of the invention is an antibody raised against an inhibitor of a Hh polypeptide that binds to a Hh polypeptide in competition with a Patched protein, a proposed Hh receptor. Certain antibodies against such an inhibitor mimic the region of a Hh polypeptide which binds to the inhibitor, which may be a region that binds to the Hh receptor. Consequently, such antibodies bind to a Patched protein and elicit similar kind of response in a cell as a Hh polypeptide does.

Another embodiment of the invention is an anti-idiotypic antibody. An anti-idiotypic antibody is raised against a primary antibody. Certain anti-idiotypic antibodies mimic the internal image of the epitope for the primary antibody, thereby also mimicking the activity of the antigen against which the primary antibody has been raised. See, for example, Ma, J. et al., (2002) *Japan. J. Cancer Res.* 93(1):78-84; Depraetere, H. et al., (2000) *Eur. J. Biochem.* 267(8):2260-7; Rajeshwari, K. and Karande, A. A., (1999) *Immunol. Invest.* 28(2-3):103-14. Anti-idiotypic antibodies against an antibody that is specific to the site of a Hh polypeptide involved in functional binding to its receptor, mirror the structure of such a site on a Hh polypeptide. Therefore, such anti-idiotypic antibodies also bind to a receptor for a Hh polypeptide and elicit biologically relevant responses. Anti-idiotypic antibodies are produced in a similar manner to producing any antibody.

Antibodies useful in the present invention may be monoclonal or polyclonal antibodies. As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art. In addition, methods exist to produce monoclonal antibodies in transgenic animals or plants (Pollock et al., *J. Immunol. Methods,* 231:147, 1999; Russell, *Curr. Top. Microbiol. Immunol.* 240:119, 1999).

In one embodiment, the portion of the antibody comprises a light chain of the antibody. As used herein, "light chain" means the smaller polypeptide of an antibody molecule composed of one variable domain (VL) and one constant domain (CL), or fragments thereof. In one embodiment, the portion of the antibody comprises a heavy chain of the antibody. As used herein, "heavy chain" means the larger polypeptide of an antibody molecule composed of one variable domain (VH) and three or four constant domains (CH1, CH2, CH3, and CH4), or fragments thereof. In one embodiment, the portion of the antibody comprises a Fab portion of the antibody. As used herein, "Fab" means a monovalent antigen binding fragment of an immunoglobulin that consists of one light chain and part of a heavy chain. In one embodiment, the portion of the antibody comprises a F(ab')2 portion of the antibody. As used herein, "F(ab')2 fragment" means a bivalent antigen binding fragment of an immunoglobulin that consists of both light chains and part of both heavy chains. Fab and F(ab')2 can be obtained by brief pepsin digestion or recombinant methods. In one embodiment, the portion of the antibody comprises one or more CDR domains of the antibody. As used herein, "CDR" or "complementarity determining region" means a highly variable sequence of amino acids in the variable domain of an antibody, which directly interacts with the epitope of the antigen. Variable domains of an antibody also contains framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

The antibody may be a human or nonhuman antibody. The nonhuman antibody may be "humanized" by recombinant methods to reduce its immunogenicity in man. Methods for humanizing antibodies are known to those skilled in the art. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody.

Methods of humanization include, but are not limited to, those described in U.S. Pat. Nos. 4,816,567, 5,225,539, 5,585,089, 5,693,761, 5,693,762 and 5,859,205, which are hereby incorporated by reference. One of ordinary skill in the art will be familiar with other methods for antibody humanization.

Using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150, 584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

RNA Interference as HH Agonist

In one embodiment the Hh agonists are RNA interference (RNAi) molecules. RNAi constructs comprise double stranded RNA that can specifically block expression of a target gene. Accordingly, RNAi constructs that specifically block expression of a gene that negatively regulates the Hh signaling pathway can act as an agonist of the Hh signaling pathway. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation; however, the biochemical mechanisms are currently an active area of research. Despite some uncertainty regarding the mechanism of action, RNAi provides a useful method of inhibiting gene expression in vitro or in vivo.

In preferred embodiments, hh RNAi agonists of the invention are siRNA, either transcribed from a DNA vector encoding a short hairpin (stem-loop) siRNA, a synthetic siRNA, or longer dsRNA which can be further processed to shorter siRNA (such as 21-23 nucleotides), encoding sequences that interfere with the expression of negative control elements of the Hh signaling pathway, such as Patched or Gli-3.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 base pairs, or 1 in 10 base pairs, or 1 in 20 base pairs, or 1 in 50 base pairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Exemplary Targets of RNAi

The genes listed below are negative regulators of the Hh signaling pathway. A hh RNAi agonist inhibiting a negative regulator will be useful to up-regulate the Hh signaling, for example, in conditions involving hypoactivity of Hh signaling, or when it is desirable to upregulate Hh pathway signaling.

TABLE 2

Negative Regulators of Hedgehog Signaling

| Drosophila (Acc. No.) | Other Species (Acc. No.) |
|---|---|
| Ptc (M28999) | Human PTC1 (U59464); human PTC2 (AF091501); mouse Ptc1 (U46155); rat Ptc1 (AF079162); *Xenopus* Ptc1 (AF302765); chicken Ptc1 (U40074); zebrafish Ptc1 (X98883); Japanese firebelly newt Ptc1 (AB000848); mouse Ptc2 (AB010833); chicken Ptc2 (AF409095); *Xenopus* Ptc2 (AB037688); zebrafish Ptc2 (AJ007742); Japanese firebelly newt Ptc2 (AB000846) |
| Cos2 (AF019250) | Human homolog (AY237538); rat homolog (XM_218828); mouse homolog (XM_133575); *Anopheles gambiae* str. PEST homolog (XM_309818). |
| Su(fu) (NM_080502) | Human SUFU (NM_016169); mouse homolog (AJ131692); rat homolog (XM_219957); chicken homolog (AF487888); *Anopheles gambiae* str. PEST homolog (XM_321114); zebrafish homolog (BC045348). |
| Sgg (X70862) | Human GSK3α (L33801); mouse GSK3α (AF156099); rat GSK3α (X53428); zebrafish GSK3α (AB032265); *Xenopus* GSK3α (U31862). |
| Pka-C1 (AY069425) | Human PKA-C1 (X07767, M34181, M34182); rat homolog (X57986); mouse homolog (BC003238); sheep homolog (AF238979); bovine homolog (X67154); pig homolog (X05998); rabbit homolog (AF367428;); hamster homolog (M63311); *Xenopus* homolog (AJ413219). |
| CK1α Aψ069346) | Human homolog (X80693); mouse homolog (BC019740); rat homolog (U77582); chicken homolog (AF042862); sheep homolog (AB050945); bovine homolog (AB050944); pig homolog (F22872). |
| Slmb (AF032878) | Human homolog (AF101784; AF176022); mouse homolog (AF391190); *Xenopus* (M98268); chicken (AF113946). | i) Nucleotide sequence accession numbers from the public databases are listed in "( )."

Patched inhibits a second membrane-bound protein, Smoothened, in the absence of Hh polypeptide. The association of Patched and Smoothened enables an intracellular high-molecular-weight protein complex, which includes the kinesin-related molecule Costal2 (Cos2), a serine-threonine protein kinase Fused (Fu), and the protein Suppressor of Fused [Su(fu)], to promote the proteolytic processing of full-length Cubitus interruptus (Ci155), thereby generating a transcriptional repressor Ci75. Although not yet proven to interact directly with this high-molecular weight complex, protein kinase A (PKA), glycogen synthase kinase 3 (GSK3), and casein kinase 1α (CK1α) also modify Ci to regulate its cleavage. This process also depends on Slimb. Binding of Hh to Ptc relieves inhibition of Smo and, by an unknown mechanism, Smo suppresses the Ci-processing activity of the cytoplasmic complex. Unprocessed Ci155 then translocates to the nucleus, where it activates the expression of specific target genes.

Sporadic tumors in humans demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). Most of the identified mutations resulted in premature stop codons or frame shifts (Lench, N. J. et al. (1997) *Hum. Genet.* 100 (5-6): 497-502). In addition, there are several identified mutations that are point mutations leading to amino acid substitutions in either extracellular or cytoplasmic domains. The alterations did not occur in the corresponding germ line DNA. An example of *Drosophila* patched gene is represented in SEQ ID No:23.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

Recently, Lum et al. (*Science* (2003) 299: 2039-2045) identified several additional members of the Hh signaling pathway. Using both in vitro and in vivo assays, these authors identified four genes whose products were not previously recognized as having specific roles in Hh signaling: Among the four, CK1α is a negative regulator, while other three are positive regulators. CK1α is a positive regulator of Ci cleavage, a process that generates its repressor form (Price and Kalderon (2002) *Cell* 108: 823-835, FIG. 1). ThusCK1α is a negative regulator of Hh signaling.

All Hh signaling pathway genes in various species can be routinely obtained from public and proprietary databases, such as GenBank, EMBL, FlyBase, to name but a few. In certain organisms, such as human and *Drosophila*, the whole genome is sequenced, and sequence comparison programs, such as the BLAST series of programs offered online at the NCBI website can be used to retrieve the most updated sequences of any known Hh signaling pathway genes. The following table list several representative members of the known Hh signaling pathway genes in various species. It is by no means exhaustive, and should not be viewed as limiting in any sense. Rather, it serves as a useful starting point for an exhaustive search, which a skilled artisan would be able to perform these searches' using routine biotechniques. Some genes may have several different database entries with different accession numbers, but are nonetheless same or almost the same in sequence. Regardless, only one entry for each gene is provided in the table above.

Hedgehog Mutants as HH Antagonists

In one embodiment, the agent to inhibit the pathway is a mutant HH polypeptide that binds to a physiological target of a HH polypeptide but has lost its ability to stimulate the HH signaling pathway. It is well known that a polypeptide may retain its physiological binding capabilities even as a mutation abolishes the activity that the binding to a target normally induces. Thus, such mutant polypeptide competes with wild-type polypeptide for binding to the target and competitively inhibits the wild-type polypeptide. A mutant HH polypeptide may be naturally occurring mutant, or it can be engineered from any exemplary HH polypeptide described above, such as those encoded by SEQ ID NOs: 1-9 and 19.

These negative mutants can be identified through recombinant techniques well known in the art and described in detail in U.S. patent application Ser. No. 10/652,298 and PCT/US03/27279. Briefly, a nucleic acid encoding a HH polypeptide is subjected to random mutagenesis by combinatorial mutagenesis and the resulting mutant pool is screened for the ability to bind to Patched polypeptide, a natural receptor for HH, or to inhibit wild-type HH from binding to Patched, but without an ability to induce activities that HH specifically induces.

In one embodiment, the agent to practice the methods of the invention is a fusion protein or can be produced as a fusion protein, which comprises all or a portion of a negative mutant HH polypeptide and any other peptide portion, such as a marker or another biologically active protein. Additional domains may be included in the subject fusion proteins of this invention. It is widely appreciated that fusion proteins can also facilitate the expression of proteins, and accordingly, can be used in the expression of the mutant HH polypeptides of the present invention. For example, the fusion proteins may include domains that facilitate their purification, e.g., "histidine tags" or a glutathione-5-transferase domain. They may include "epitope tags" encoding peptides recognized by known monoclonal antibodies for the detection of proteins within cells or the capture of proteins by antibodies in vitro. In a preferred embodiment, the recombinant HH polypeptide is a fusion protein containing a domain that facilitates its purification, such as a HH/GST fusion protein.

It may be necessary in some instances to introduce an unstructured polypeptide linker region between an analog peptide and other portions of the chimeric protein. The linker can facilitate enhanced flexibility of the fusion protein. The linker can also reduce steric hindrance between any two fragments of the fusion protein. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the 1cI and LexA proteins. Alternatively, the linker can be of synthetic origin. For instance, the sequence $(Gly_4Ser)_3$ can be used as a synthetic unstructured linker. Linkers of this type are described in Huston et al. (1988) *Proc. Nat. Acad. Sci. USA* 85:4879; and U.S. Pat. No. 5,091,513. In some embodiments it is preferable that the design of a linker involve an arrangement of domains which requires the linker to span a relatively short distance, preferably less than about 10 Å. However, in certain embodiments, depending, e.g., upon the selected domains and the configuration, the linker may span a distance of up to about 50 Å.

Small Molecule Antagonists of HH Pathway

Hh antagonist compounds for use in certain embodiments of the invention are described in the formulas below and in U.S. patent application Ser. No. 10/652,298, and the methods of making the compositions are described in detail in the following U.S. patent application Ser. Nos. 09/724,277 09/688,076, 09/708,974, 09/708,964, 09/890,975, 09/977, 096, and 10/407,551, and U.S. Pat. Nos. 6,545,005, 6,552, 016, and 6,432,970, the contents of which are incorporated herein in their entireties. For each of the parts below, the variable groups and numbers (e.g., $R_1$, L, $Z_2$) are individually and distinctly defined, and are internally consistent but not necessarily consistent from part to part. These five parts are described in detail below.

In certain embodiments, the subject antagonists can be chosen on the basis of their selectively for the Hh pathway, or more specifically, the smoothened pathway. A preferred embodiment of such antagonists is an antagonist of a Smoothened protein.

In particular embodiments, the antagonist is chosen for use because it is more selective for one Patched isoform over the next, e.g., 10-fold, and more preferably at least 100- or even 1000-fold more selective for one Patched pathway (ptc-1, ptc-2) over another. Likewise, the antagonist may be chosen for use because it is more selective for one Smoothened isoform over the next, e.g., 10-fold, and more preferably at least 100- or even 1000-fold more selective for one wild-type Smoothened protein (should various isoforms exist) or for activated smoothened mutants relative to wild-type Smoothened.

In certain embodiments, the subject method can be carried out conjointly with the administration of growth and/or trophic factors, or compositions that also act on other parts of the Hedgehog/Smoothened pathway. For instance, it is contemplated that the subject methods can include treatment with an agent that modulates cAMP levels, e.g., increasing or decreasing intracellular levels of cAMP. In one embodiment, the subject method utilizes a Smoothened antagonist, and the conjoint agent elevates cAMP levels in order to enhance the efficacy of the smoothened antagonist.

For example, compounds that may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, norepinephrine, oxyfedrine, pirbuterol, prenalterol, procaterol, propranolol, protokylol, quinterenol, reproterol, rimiterol, ritodrine, salmefamol, soterenol, salmeterol, terbutaline, tretoquinol, tulobuterol, and xamoterol.

Compounds which may inhibit a cAMP phosphodiesterase include anrinone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, papverine, MDL 12330A, SQ 22536, GDPssS, clonidine, type III and type IV phosphodiesterase inhibitors, methylxanthines such as pentoxifylline, theophylline, theobromine, pyrrolidinones and phenyl cycloalkane and cycloalkene derivatives (described in PCT publications Nos. WO 92/19594 and WO 92/10190), lisophylline, and fenoxamine.

Analogs of cAMP which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Sp-adenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-O-monobutyryl-cAMP, 2'-O-monobutryl-8-bromo-cAMP, $N^6$-monobutryl-2'-deoxy-cAMP, and 2'-O-monosuccinyl-cAMP.

Compounds which may reduce the levels or activity of cAMP include prostaglandylinositol cyclic phosphate (cyclic PIP), endothelins (ET)-1 and -3, norepinepurine, K252a, dideoxyadenosine, dynorphins, melatonin, pertussis toxin, staurosporine, Gi agonists, MDL 12330A, SQ 22536, GDPssS and clonidine, beta-blockers, and ligands of G-protein coupled receptors. Additional compounds are disclosed in U.S. Pat. Nos. 5,891,875, 5,260,210, and 5,795,756.

Exemplary Compounds Part 1:

As described in further detail below, it is contemplated that the subject methods can be carried out using any of a variety of different steroidal alkaloids which can be readily identified, e.g., by such drug screening assays as described herein. Steroidal alkaloids have a fairly complex nitrogen-containing nucleus. Two exemplary classes of steroidal alkaloids for use in the subject methods are the *Solanum* type and the *Veratrum* type. The above notwithstanding, in a preferred embodiment, the methods and compositions of the present invention make use of compounds having a steroidal alkaloid ring system of cyclopamine.

There are more than 50 naturally occurring *veratrum* alkaloids including veratramine, cyclopamine, cycloposine, jervine, and muldamine occurring in plants of the *Veratrum* spp. The *Zigadenus* spp., death camas, also produces several *veratrum*-type of steroidal alkaloids including zygacine. In general, many of the *veratrum* alkaloids (e.g., jervine, cyclopamine and cycloposine) consist of a modified steroid skeleton attached spiro to a furanopiperidine. A typical *veratrum*-type alkaloid may be represented by:

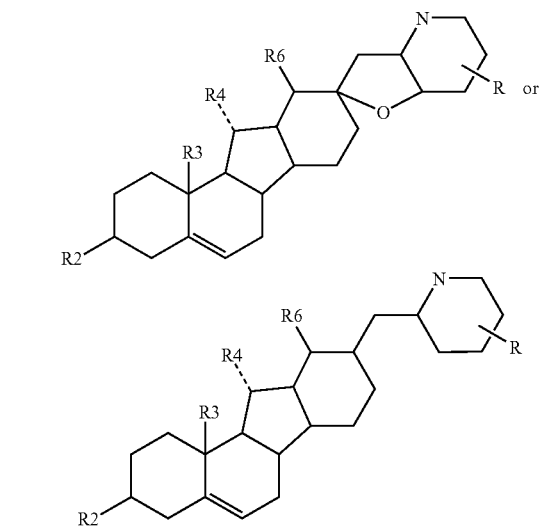

An example of the *Solanum* type is solanidine. This steroidal alkaloid is the nucleus (i.e., aglycone) for two important glycoalkaloids, solanine and chaconine, found in potatoes. Other plants in the *Solanum* family including various nightshades, Jerusalem cherries, and tomatoes also contain *solanum*-type glycoalkaloids. Glycoalkaloids are glycosides of alkaloids. A typical *solanum*-type alkaloid may be represented by:

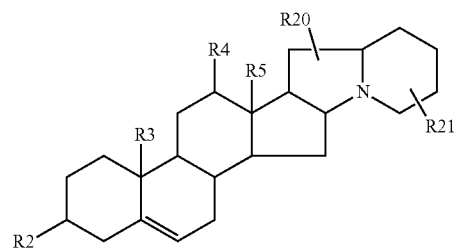

Based on these structures, and the possibility that certain unwanted side effects can be reduced by some manipulation of the structure, a wide range of steroidal alkaloids are contemplated as potential smoothened antagonists for use in the subject method. For example, compounds useful in the subject methods include steroidal alkaloids represented in the general formulas (I), or unsaturated forms thereof and/or seco-, nor- or homo-derivatives thereof:

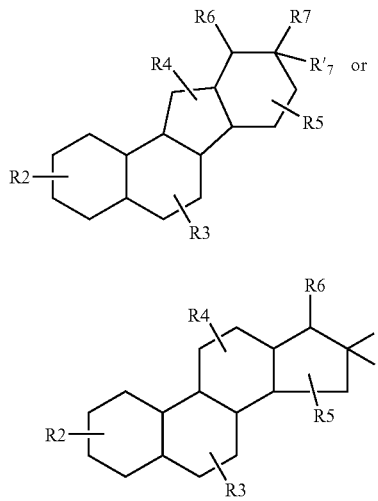

Formula I wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —(CH$_2$)$_m$—R$_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes an amine, e.g., as one of the atoms which makes up the ring;

$R_8$ represents an aryl, a cycloalkyl, a cycloalkenyl, a heterocycle, or a polycycle; and m is an integer in the range 0 to 8 inclusive.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of $R_6$, $R_7$, or $R'_7$ is a tertiary amine.

In particular embodiments, $R_3$, for each occurrence, is an —OH, alkyl, —O-alkyl, —C(O)-alkyl, or —C(O)—R$_8$.

In particular embodiments, $R_4$, for each occurrence, is an absent, or represents —OH, =O, alkyl, —O-alkyl, —C(O)-alkyl, or —C(O)—R$_8$.

In particular embodiments, two of $R_6$, $R_7$, and $R'_7$ taken together form a nitrogen-containing ring, such as a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine.

In certain embodiments, the nitrogen-containing ring comprises a tertiary amine, e.g., by having an extraannular substituent on the nitrogen atom, e.g., an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In particular embodiments, $R_8$ represents an aryl, a cycloalkyl, a cycloalkenyl, a heterocycle, or a polycycle, and preferably $R_8$ is a piperidine, pyrrolidine, pyridine, pyrimidine, morpholine, thiomorpholine, pyridazine, etc.

In certain preferred embodiments, the definitions outlined above apply, and the subject compounds are represented by general formula Ia or unsaturated forms thereof and/or seco-, nor- or homo-derivatives thereof:

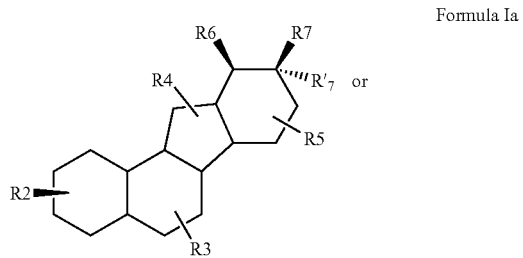

Formula Ia

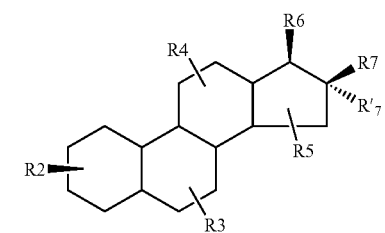

In certain embodiments, the steroidal alkaloid is represented in the general formula (II), or unsaturated forms thereof and/or seco-, nor- or homo-derivatives thereof:

Formula II

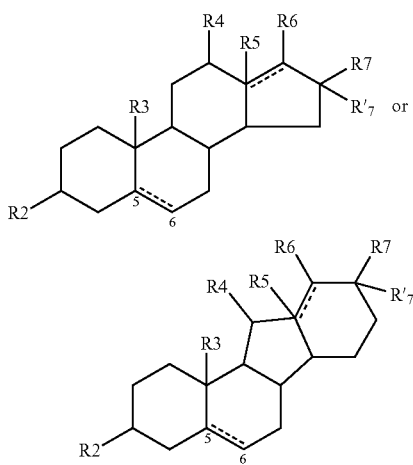

wherein R$_2$, R$_3$, R$_4$, R$_5$, R$_6$, R$_7$, and R'$_7$ are as defined above, and X represents O or S, though preferably O.

In certain embodiments, R$_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of R$_6$, R$_7$, or R'$_7$ is a tertiary amine, e.g., substituted with a substituted or unsubstituted alkyl. In certain embodiments, the amine is part of a bicyclic ring system formed from R$_7$ and R'$_7$, e.g., a furanopiperidine system, and the third substituent is an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IIa or unsaturated forms thereof and/or seco-, nor- or homo-derivatives thereof:

Formula IIa

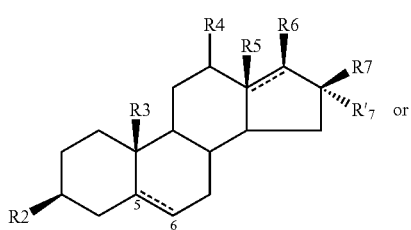

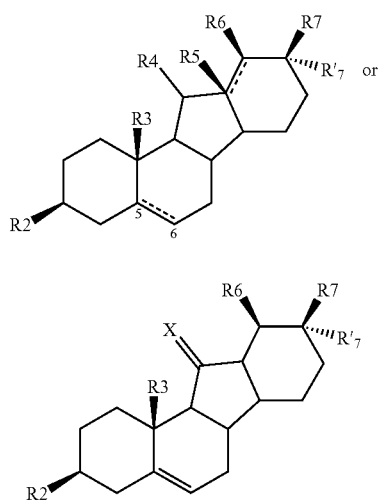

In certain embodiments, the steroidal alkaloid is represented in the general formula (III), or unsaturated forms thereof and/or seco-, nor- or homo-derivatives thereof:

Formula III

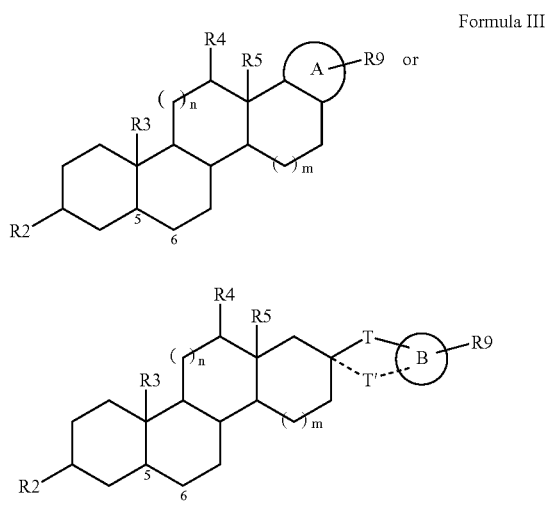

wherein
R$_2$, R$_3$, R$_4$, R$_5$ and R$_8$ are as defined above;
A and B represent monocyclic or polycyclic groups;
T represents an alkyl, an aminoalkyl, a carboxyl, an ester, an amide, ether or amine linkage of 1-10 bond lengths;
T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;
R$_9$ represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$; and n and m are, independently, zero, 1 or 2;

with the proviso that A, or T, T', and B, taken together, include at least one amine. In certain embodiments, R$_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of A, or T, T', and B, is a tertiary amine, e.g., substituted with a substituted or unsubstituted alkyl, e.g., substituted with aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IIIa or unsaturated forms thereof and/or seco-, nor- or homo-derivatives thereof:

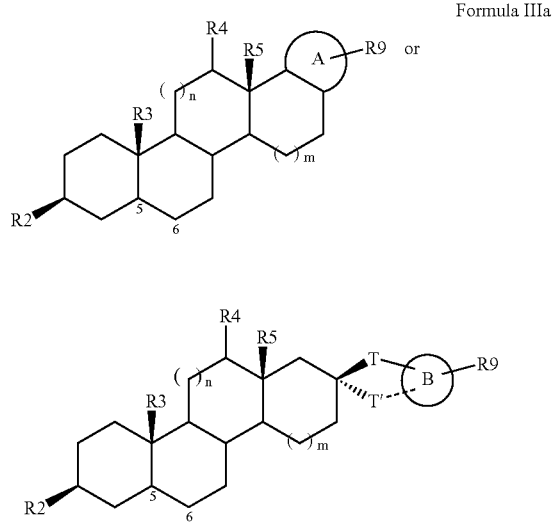

Formula IIIa

For example, the subject methods can utilize smoothened antagonists based on the *veratrum*-type steroidal alkaloids jervine, cyclopamine, cycloposine, mukiamine or veratramine, e.g., which may be represented in the general formula (IV), or unsaturated forms thereof and/or seco-, nor- or homo-derivatives thereof:

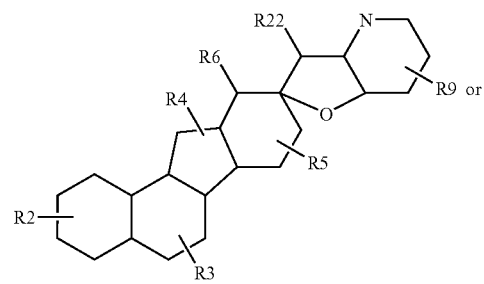

Formula IV

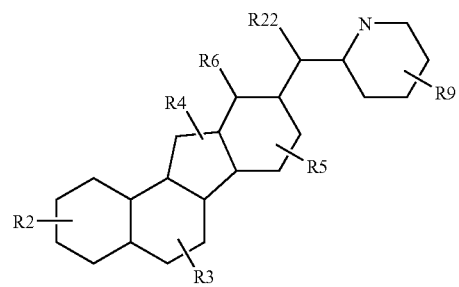

wherein

R$_2$, R$_3$, R$_4$, R$_5$, R$_6$ and R$_9$ are as defined above;

R$_{22}$ is absent or represents an alkyl, an alkoxyl or —OH.

In certain embodiments, R$_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, R9 includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc. In certain embodiments, the extraannular substituent (e.g., R9) of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IVa or unsaturated forms thereof and/or seco-, nor- or homo-derivatives thereof:

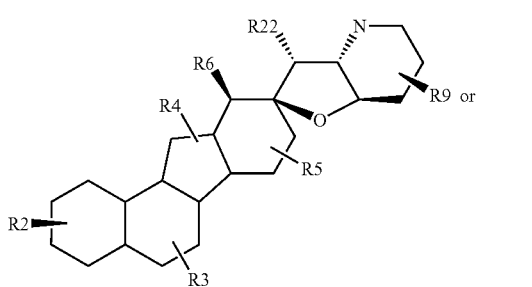

Formula IVa

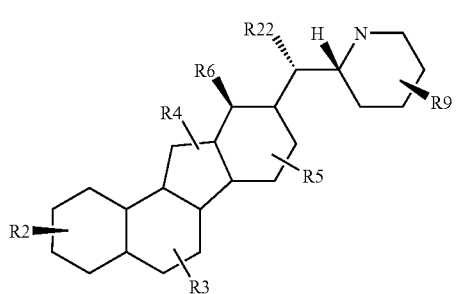

In certain embodiments, the steroidal alkaloid is represented in the general formula (V) or unsaturated forms thereof and/or seco-, nor- or homo-derivatives thereof:

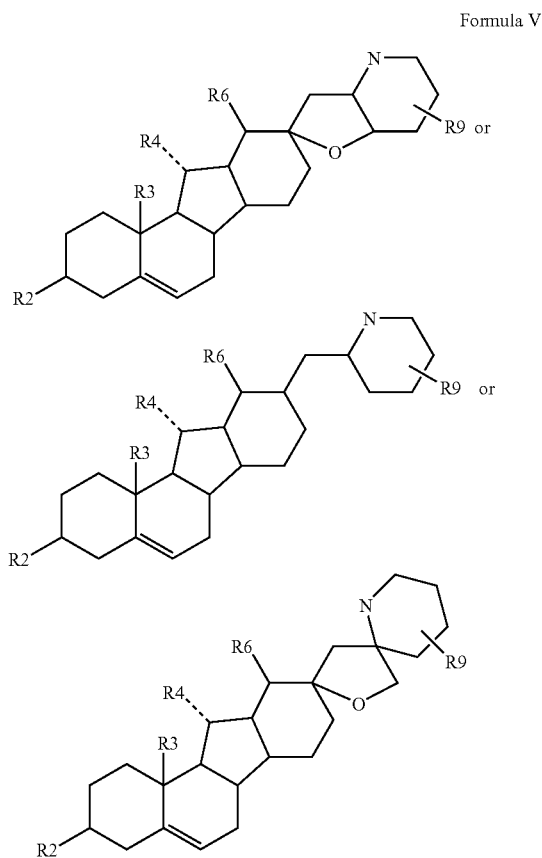

Formula V wherein $R_2$, $R_3$, $R_4$, $R_6$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, $R_9$ includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc.

In certain embodiments, the extraannular substituent of the tertiary amine (e.g., $R_9$) is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula Va or unsaturated forms thereof and/or seco-, nor- or homo-derivatives thereof:

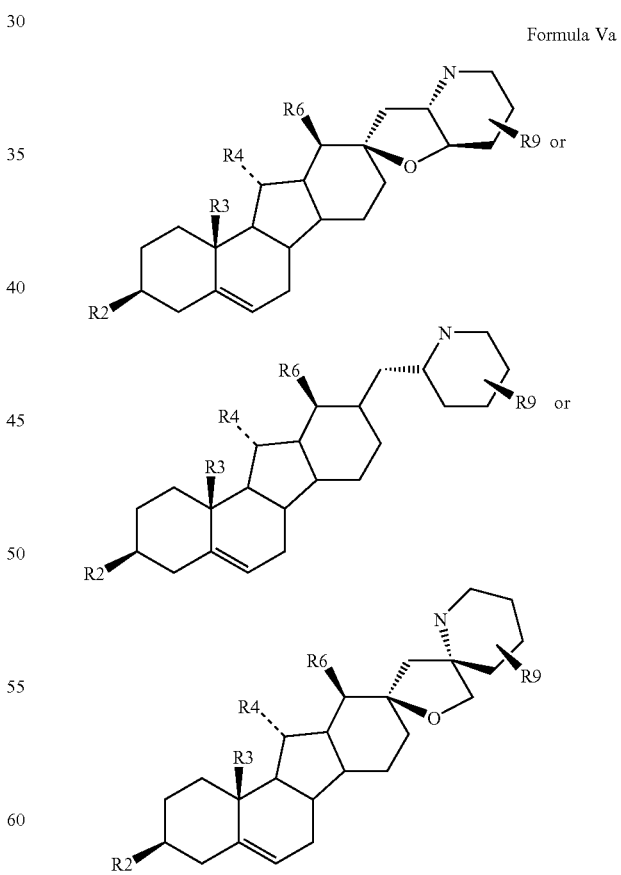

Formula Va

Another class of Smoothened antagonists can be based on the *veratrum*-type steroidal alkaloids resembling verticine and zygacine, e.g., general formula (VI), or unsaturated forms thereof and/or seco-, nor- or homo-derivatives thereof:

Formula VI

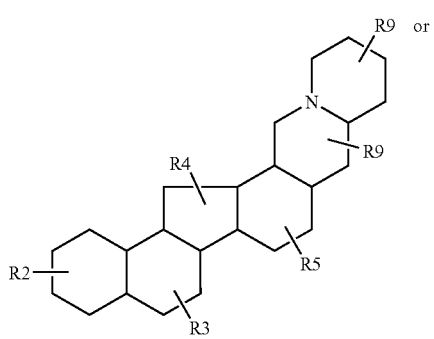

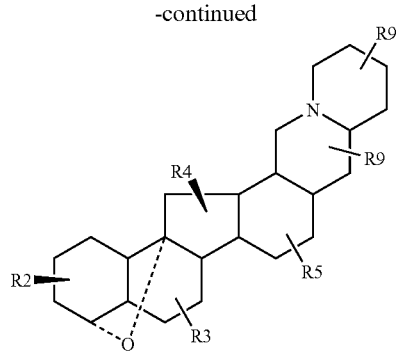

In certain embodiments, the steroidal alkaloid is represented in the general formula (VII) or unsaturated forms thereof and/or seco-, nor- or homo-derivatives thereof:

Formula VII

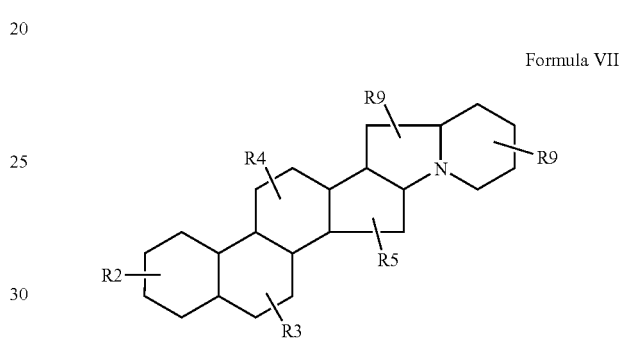

wherein $R_2$, $R_3$, $R_4$, $R_5$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

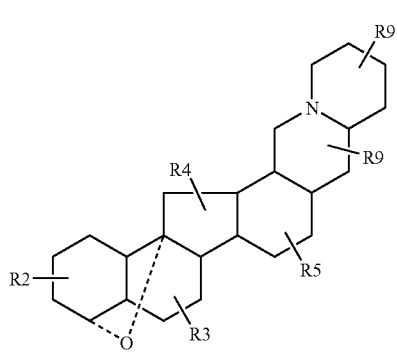

wherein $R_2$, $R_3$, $R_4$, $R_5$ and $R_9$ are as defined above.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain preferred embodiments, the definitions outlined above apply, and the subject compounds are represented by general formula VIa or unsaturated forms thereof and/or seco-, nor- or homo-derivatives thereof:

Formula VIa

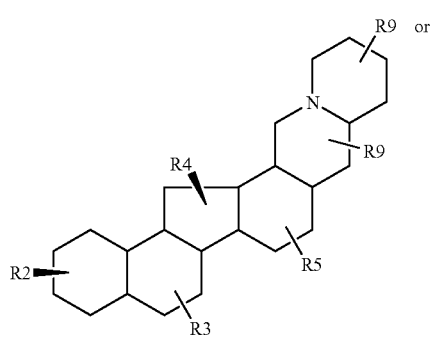

In certain preferred embodiments, the definitions outlined above apply, and the subject compounds are represented by general formula VIIa or unsaturated forms thereof and/or seco-, nor- or homo-derivatives thereof:

Formula VIIa

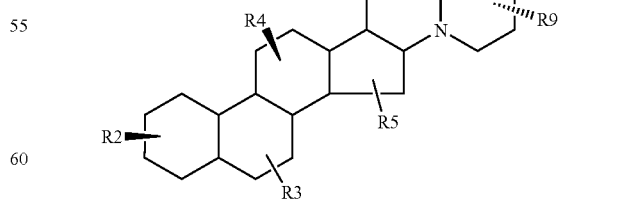

Above-listed compounds useful in the subject methods may be modified to increase the bioavailability, activity, or other pharmacologically relevant property of the compound. For example, forskolin has the formula:

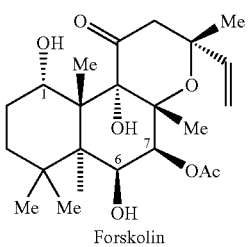
Forskolin

Modifications of forskolin that have been found to increase the hydrophilic character of forskolin without severely attenuating the desired biological activity include acylation of the hydroxyls at C6 and/or C7 (after removal of the acetyl group) with hydrophilic acyl groups. In compounds wherein C6 is acylated with a hydrophilic acyl group, C7 may optionally be deacetylated. Suitable hydrophilic acyl groups include groups having the structure —(CO)(CH$_2$)$_n$X, wherein X is OH or NR$_2$; R is hydrogen, a C$_1$-C$_4$ alkyl group, or two Rs taken together form a ring comprising 3-8 atoms, preferably 5-7 atoms, which may include heteroatoms (e.g., piperazine or morpholine rings); and n is an integer from 1-6, preferably from 1-4, even more preferably from 1-2. Other suitable hydrophilic acyl groups include hydrophilic amino acids or derivatives thereof, such as aspartic acid, glutamic acid, asparagine, glutamine, serine, threonine, tyrosine, etc., including amino acids having a heterocyclic side chain. Forskolin, or other compounds listed above, modified by other possible hydrophilic acyl side chains known to those of skill in the art may be readily synthesized and tested for activity in the present method. Similarly, variants or derivatives of any of the above-listed compounds may be effective as cAMP antagonists in the subject method, e.g., in order to decrease cAMP levels and potentiate the activity of a smoothened activator. Those skilled in the art will readily be able to synthesize and test such derivatives for suitable activity.

Exemplary Compounds Part II:

Additional steroidal alkaloids are contemplated as potential Hh antagonists for use in the subject method. For example, compounds useful in the subject methods include steroidal alkaloids represented in the general formulas (VIII), or unsaturated forms thereof and/or seco-, nor- or homo-derivatives thereof:

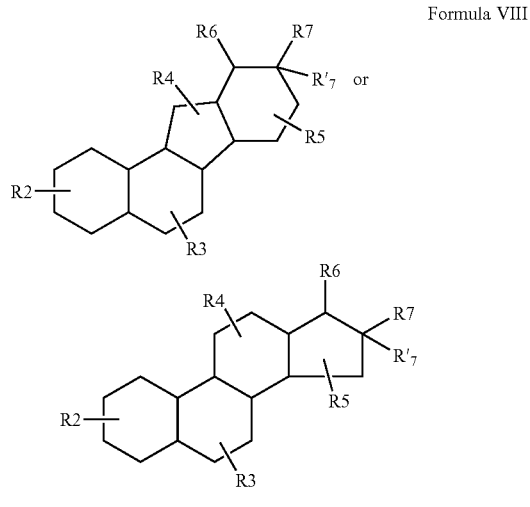

wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —(CH$_2$)$_m$—R$_8$;

$R_6$, $R_7$, and R'$_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$, or $R_6$ and $R_7$, or $R_7$ and R'$_7$, taken together form a ring or polycyclic ring, e.g., which is substituted or unsubstituted, with the proviso that at least one of $R_6$, $R_7$, or R'$_7$ is present and includes a primary or secondary amine;

$R_8$ represents an aryl, a cycloalkyl, a cycloalkenyl, a heterocycle, or a polycycle; and m is an integer in the range 0 to 8 inclusive.

In preferred embodiments, $R_2$ and $R_3$, for each occurrence, is an —OH, alkyl, —O-alkyl, —C(O)-alkyl, or —C(O)—R$_8$;

$R_4$, for each occurrence, is an absent, or represents —OH, =O, alkyl, —O-alkyl, —C(O)-alkyl, or —C(O)—R$_8$;

$R_6$, $R_7$, and R'$_7$ each independently represent, hydrogen, alkyls, alkenyls, alkynyls, amines, imines, amides, carbonyls, carboxyls, carboxamides, ethers, thioethers, esters, or —(CH$_2$)$_m$—R$_8$, or $R_7$, and R'$_7$ taken together form a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine with the proviso that at least one of $R_6$, $R_7$, or R'$_7$ is present and includes a primary or secondary amine;

R8 represents an aryl, a cycloalkyl, a cycloalkenyl, a heterocycle, or a polycycle, and preferably R8 is a piperidine, pyrimidine, morpholine, thiomorpholine, pyridazine, In certain preferred embodiments, the definitions outlined above apply, and the subject compounds are represented by general formula VIIIa or unsaturated forms thereof and/or seco-, nor- or homo-derivatives thereof:

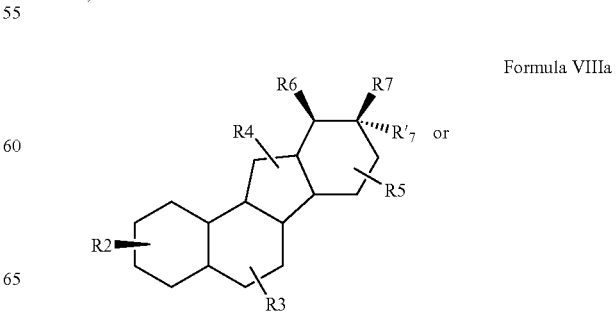

-continued

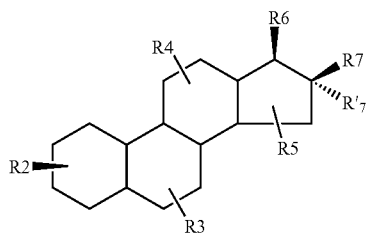

In preferred embodiments, the subject hedgehog antagonists can be represented in one of the following general formulas (IX) or unsaturated forms thereof and/or seco-, nor- or homo-derivatives thereof:

Formula IX

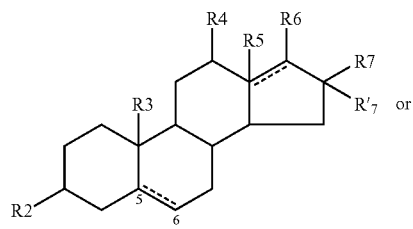

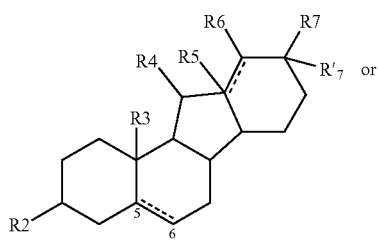

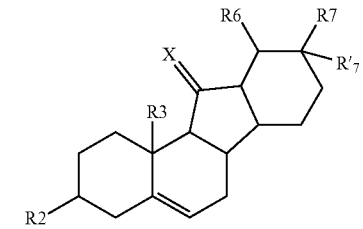

wherein $R_2$, $R_3$, $R_4$, $R_5$, $R_6$, $R_7$, and $R'_7$ are as defined above, and X represents O or S, though preferably O.

In certain preferred embodiments, the definitions outlined above apply, and the subject compounds are represented by general formula IXa or unsaturated forms thereof and/or seco-, nor- or homo-derivatives thereof:

Formula IXa

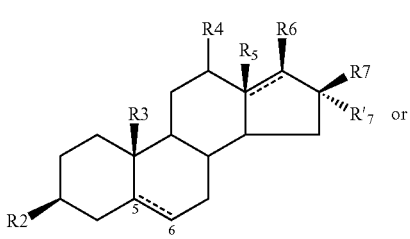

-continued

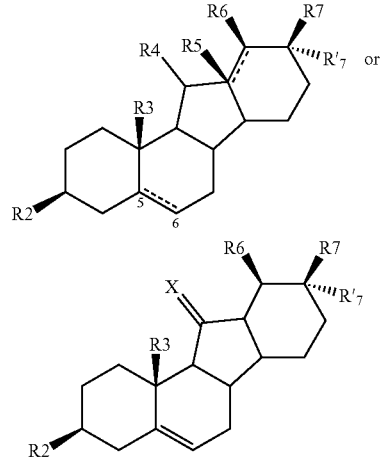

In certain embodiments, the subject hedgehog antagonists are represented by the general formula (X) or unsaturated forms thereof and/or seco-, nor- or homo-derivatives thereof:

Formula X

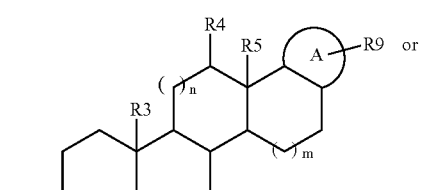

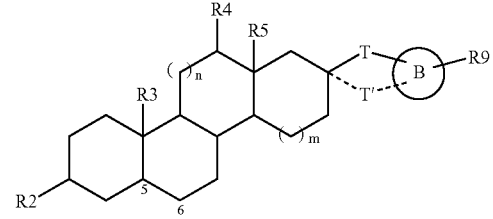

wherein
$R_2$, $R_3$, $R_4$, $R_5$ and $R_8$ are as defined above;
A and B represent monocyclic or polycyclic groups;
T represents an alkyl, an aminoalkyl, a carboxyl, an ester, an amide, ether or amine linkage of 1-10 bond lengths;
T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;
R9 represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or $-(CH_2)_m-R_8$; and
n and m are, independently, zero, 1 or 2;
with the proviso that A and $R_9$, or T, T' B and $R_9$, taken together include at least one primary or secondary amine.

In certain preferred embodiments, the definitions outlined above apply, and the subject compounds are represented by general formula Xa or unsaturated forms thereof and/or seco-, nor- or homo-derivatives thereof:

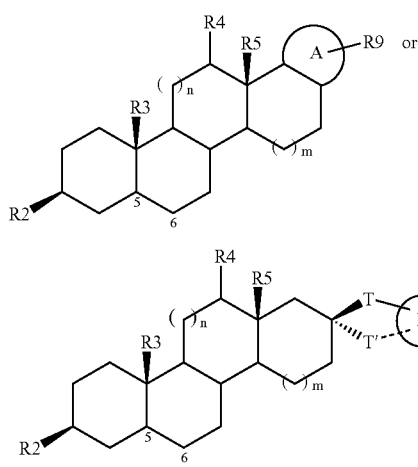

Formula Xa

For example, the subject methods can utilize hedgehog antagonists based on the *veratrum*-type steroidal alkaloids jervine, cyclopamine, cycloposine, mukiamine or veratramine, e.g., which may be represented in the general formula (XI) or unsaturated forms thereof and/or seco-, nor- or homo-derivatives thereof:

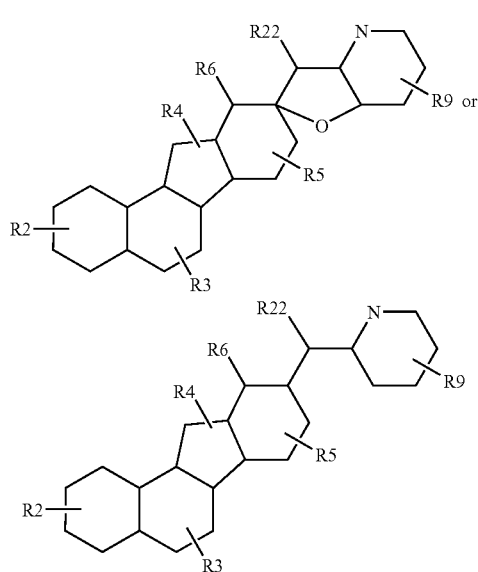

Formula XI wherein

R2, R3, R4, R5, R6 and R9 are as defined above;

R22 is absent or represents an alkyl, an alkoxyl or —OH.

In certain preferred embodiments, the definitions outlined above apply, and the subject compounds are represented by general formula XIa or unsaturated forms thereof and/or seco-, nor- or homo-derivatives thereof:

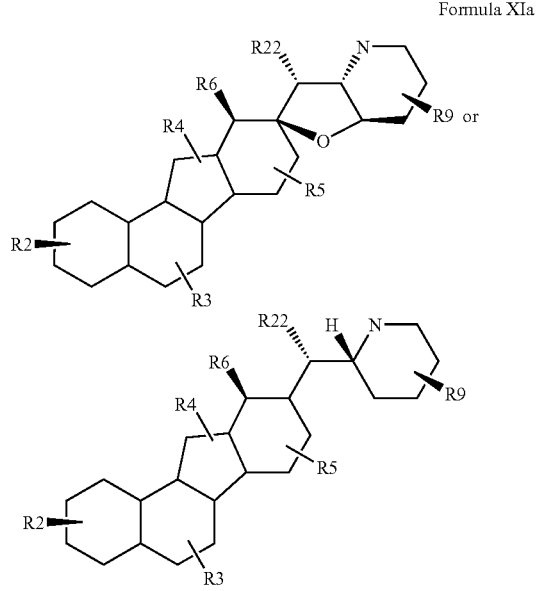

Formula XIa

In even more preferred embodiments, the subject antagonists are represented in the formulas (XII) or unsaturated forms thereof and/or seco-, nor- or homo-derivatives thereof:

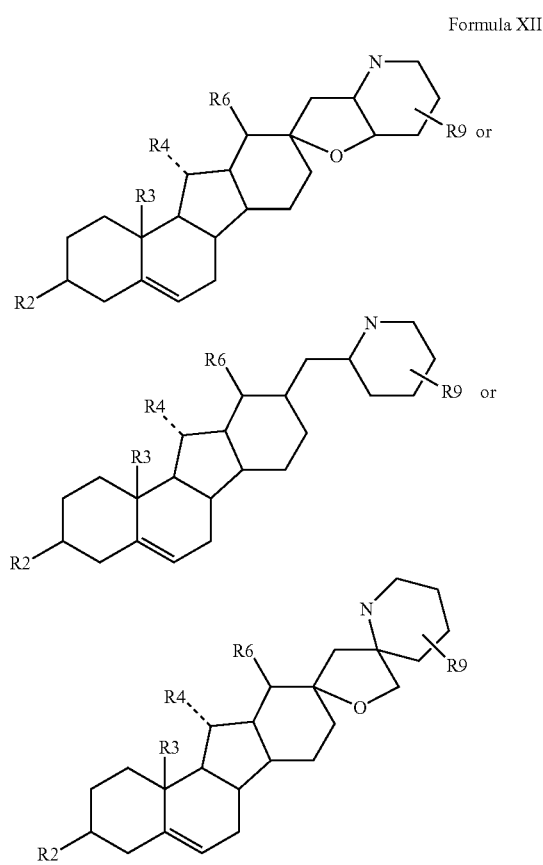

Formula XII wherein $R_2$, $R_3$, $R_4$, $R_6$ and $R_9$ are as defined above;

In certain preferred embodiments, the definitions outlined above apply, and the subject compounds are represented by general formula XIIa or unsaturated forms thereof and/or seco-, nor- or homo-derivatives thereof:

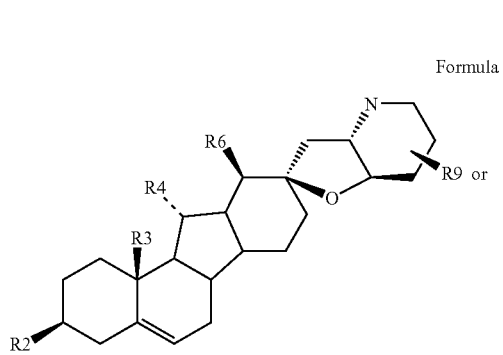
Formula XIIa

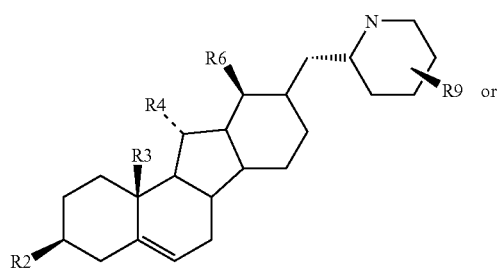

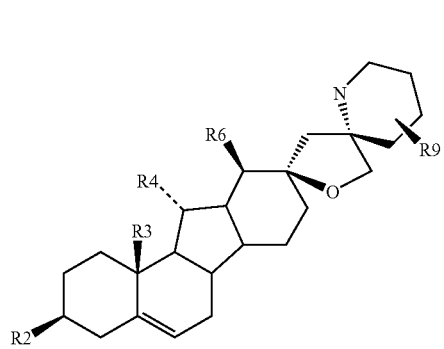

Another class of Hh antagonists can be based on the *veratrum*-type steroidal alkaloids resembling verticine and zygacine, e.g., represented in the general formulas (VI) or unsaturated forms thereof and/or seco-, nor- or homo-derivatives thereof:

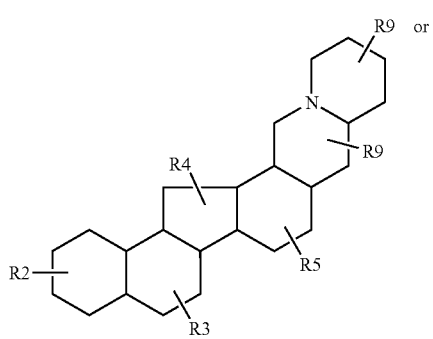
Formula XIII

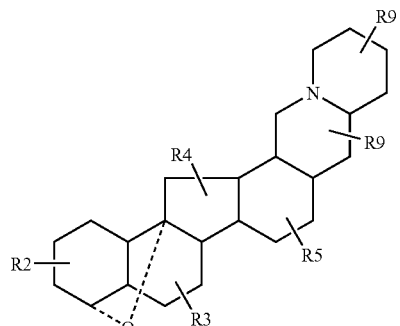

wherein $R_2$, $R_3$, $R_4$, $R_5$ and $R_9$ are as defined above.

In certain preferred embodiments, the definitions outlined above apply, and the subject compounds are represented by general formula XIIIa or unsaturated forms thereof and/or seco-, nor- or homo-derivatives thereof:

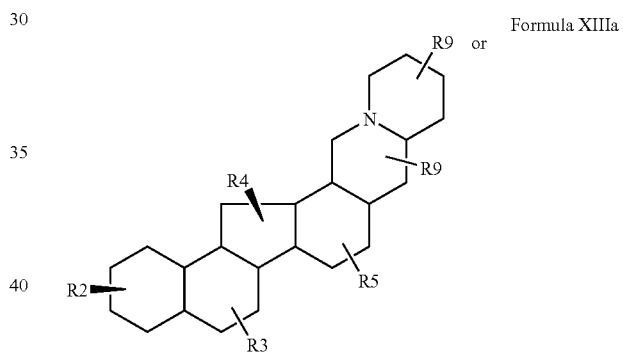
Formula XIIIa

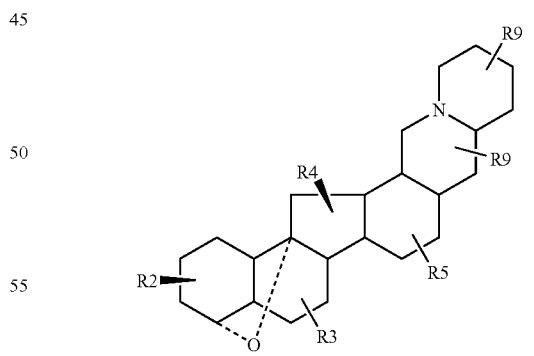

Still another class of potential Hh antagonists are based on the *solanum*-type steroidal alkaloids, e.g., solanidine, which may be represented in the general formula (XIV) or unsaturated forms thereof and/or seco-, nor- or homo-derivatives thereof:

Formula XIV

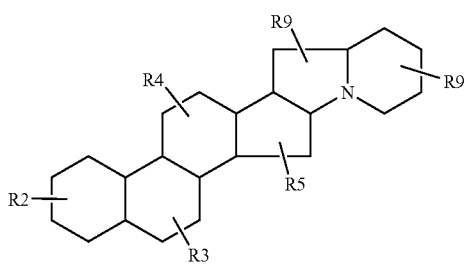

wherein $R_2$, $R_3$, $R_4$, $R_5$ and $R_9$ are as defined above.

In certain preferred embodiments, the definitions outlined above apply, and the subject compounds are represented by general formula XIVa or unsaturated forms thereof and/or seco-, nor- or homo-derivatives thereof:

Formula XIVa

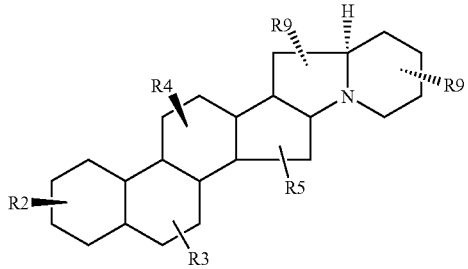

Exemplary Compounds Part III:

As described in further detail below, it is contemplated that the subject methods can be carried out using a variety of different small molecules which can be readily identified, for example, by such drug screening assays as described herein. For example, compounds useful in the subject methods include compounds may be represented by general formula (XV):

Formula XV

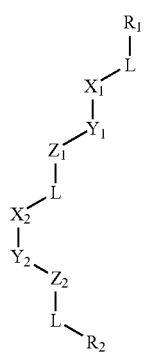

wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —(CH$_2$)$_n$aryl), or heteroaryl (e.g., substituted or unsubstituted), or heteroaralkyl (e.g., substituted or unsubstituted, e.g., —(CH$_2$)$_n$heteroaralkyl-);

L, independently for each occurrence, is absent or represents —(CH$_2$)$_n$-alkyl, -alkenyl-, -alkynyl-, —(CH$_2$)$_n$alkenyl-, —(CH$_2$)$_n$alkynyl-, —(CH$_2$)$_n$O(CH$_2$)$_p$—, —(CH$_2$)$_n$NR$_2$(CH$_2$)$_p$—, —(CH$_2$)$_n$S(CH$_2$)$_p$—, —(CH$_2$)$_n$alkenyl(CH$_2$)$_p$—, —(CH$_2$)$_n$alkynyl(CH$_2$)$_p$—, —O(CH$_2$)$_n$—, —NR$_2$(CH$_2$)$_n$—, or —S(CH$_2$)$_n$—;

$X_1$ and $X_2$ can be selected, independently, from —N(R$_8$)—, —O—, —S—, —Se—, —N=N—, —ON=CH—, —(R$_8$)N—N(R$_8$)—, —ON(R$_8$)—, a heterocycle, or a direct bond between L and $Y_1$ or $Y_2$, respectively;

$Y_1$ and $Y_2$ can be selected, independently, from —C(=O)—, —C(=S)—, —S(O$_2$)—, —S(O)—, —C(=NCN)—, —P(=O)(OR$_2$)—, a heteroaromatic group, or a direct bond between $X_1$ and $Z_1$ or $X_2$ and $Z_2$, respectively;

$Z_1$ and $Z_2$ can be selected, independently, from —N(R$_8$)—, —O—, —S—, —Se—, —N=N—, —ON=CH—, —R$_8$N—NR$_8$—, —ONR$_8$—, a heterocycle, or a direct bond between $Y_1$ or $Y_2$, respectively, and L;

$R_8$, independently for each occurrence, represents H, lower alkyl, —(CH$_2$)$_n$aryl (e.g., substituted or unsubstituted), —(CH$_2$)$_n$heteroaryl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted heteroaryl group.

In certain embodiments, $X_1$ and $X_2$ can be selected from —N(R$_8$)—, —O—, —S—, a direct bond, and a heterocycle, $Y_1$ and $Y_2$ can be selected from —C(=O)—, —C(=S)—, and —S(O$_2$)—, and $Z_1$ or $Z_2$ can be selected from —N(R$_8$)—, —O—, —S—, a direct bond, and a heterocycle.

In certain related embodiments, X1-Y1-Z1 or X2-Y2-Z2 taken together represents a urea (N—C(O)—N) or an amide (N—C(O) or C(O)—N).

In certain embodiments, $X_1$ or $X_2$ represents a diazacarbocycle, such as a piperazine.

In certain embodiments, $R_1$ represents a fused cycloalkyl-aryl or cycloalkyl-heteroaryl system, for example:

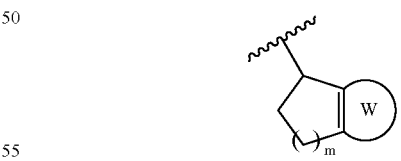

wherein W is a substituted or unsubstituted aryl or heteroaryl ring fused to the cycloalkyl ring and m is an integer from 1-4 inclusive, e.g., from 1-3, or from 1-2. The fused system may be bound to L from any carbon of the fused system, including the position depicted above. In certain embodiments, $R_1$ may represent a tetrahydronaphthyl group, and preferably $Y_1$—$X_1$-L-$R_1$ taken together represent a tetrahydronaphthyl amide group, such as:

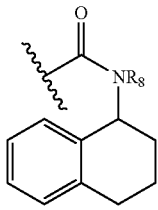

In embodiments wherein $Y_1$ and $Z_1$ are absent and $X_1$ comprises a pyrimidone, compounds useful in the present invention may be represented by general formula (XVI):

Formula XVI

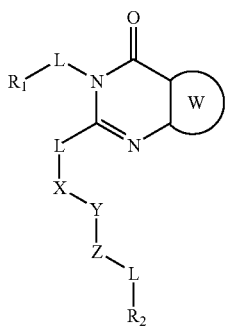

wherein, as valence and stability permit, $R_1$ and $R_2$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—;

X can be selected from —$N(R_8)$—, —O—, —S—, —Se—, —N═N—, —ON═CH—, —$(R_8)N$—$N(R_8)$—, —$ON(R_8)$—, a heterocycle, or a direct bond between L and Y;

Y can be selected from —C(═O)—, —C(═S)—, —$S(O_2)$—, —S(O)—, —C(═NCN)—, —P(═O)($OR_2$)—, a heteroaromatic group, or a direct bond between X and Z;

Z can be selected from —$N(R_8)$—, —O—, —S—, —Se—, —N═N—, —ON═CH—, —$R_8N$—$NR_8$—, —$ONR_8$—, a heterocycle, or a direct bond between Y and L;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In embodiments wherein $Y_1$ and $Z_1$ are absent and $X_1$ comprises a pyrimidone, compounds useful in the present invention may be represented by general formula (XVII):

Formula XVII

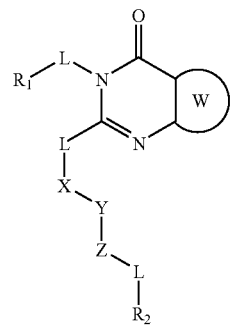

wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—, which may optionally be substituted with a group selected from H, substituted or unsubstituted lower alkyl, alkenyl, or alkynyl, cycloalkylalkyl (e.g., substituted or unsubstituted, e.g., —$(CH_2)_n$cycloalkyl), (e.g., substituted or unsubstituted), aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), preferably from H, lower alkyl, —$(CH_2)_n$aryl (e.g., substituted or unsubstituted), or —$(CH_2)_n$heteroaryl (e.g., substituted or unsubstituted);

X can be selected from —$N(R_8)$—, —O—, —S—, —Se—, —N═N—, —ON═CH—, —$(R_8)N$—$N(R_8)$—, —$ON(R_8)$—, a heterocycle, or a direct bond between L and Y;

Y can be selected from —C(═O)—, —C(═S)—, —$S(O_2)$—, —S(O)—, —C(═NCN)—, —P(═O)($OR_2$)—, a heteroaromatic group, or a direct bond between X and Z;

Z can be selected from —$N(R_8)$—, —O—, —S—, —Se—, —N═N—, —ON═CH—, —$R_8N$—$NR_8$—, —$ONR_8$—, a heterocycle, or a direct bond between Y and L;

$R_8$, independently for each occurrence, represents H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted aryl or heteroaryl group, e.g., a phenyl ring, a pyridine ring, etc. In certain embodiments wherein -$LR_1$ represents a substituted aryl or heteroaryl group, $R_1$ is preferably not substituted with an isopropoxy (Me$_2$CHO—) group. In certain embodiments wherein -LR$_1$ represents a substituted aryl or heteroaryl group, R$_1$ is preferably not substituted with an ether group. In certain embodiments, substituents on R$_1$ (e.g., other than hydrogen) are selected from halogen, cyano, alkyl, alkenyl, alkynyl, aryl, hydroxyl, (unbranched alkyl-O—), silyloxy, amino, nitro, thiol, amino, imino, amido, phosphoryl, phosphonate, phosphine, carbonyl, carboxyl, carboxamide, anhydride, silyl, thioether, alkylsulfonyl, arylsulfonyl, sulfoxide, selenoether, ketone, aldehyde, ester, or —(CH$_2$)$_m$—R$_8$. In certain embodiments, non-hydrogen substituents are selected from halogen, cyano, alkyl, alkenyl, alkynyl, aryl, nitro, thiol, imino, amido, carbonyl, carboxyl, anhydride, thioether, alkylsulfonyl, arylsulfonyl, ketone, aldehyde, and ester. In certain embodiments, non-hydrogen substituents are selected from halogen, cyano, alkyl, alkenyl, alkynyl, nitro, amido, carboxyl, anhydride, alkylsulfonyl, ketone, aldehyde, and ester.

In certain embodiments, X can be selected from —N(R$_8$)—, —O—, —S—, a direct bond, and a heterocycle, Y can be selected from —C(=O)—, —C(=S)—, and —S(O$_2$)—, and Z can be selected from —N(R$_8$)—, —O—, —S—, a direct bond, and a heterocycle. In certain such embodiments, at least one of Z and X is present.

In certain related embodiments, X—Y—Z taken together represents a urea (NC(O)N) or an amide (NC(O) or C(O)N).

In certain embodiments, W is a substituted or unsubstituted benzene ring.

In certain embodiments, X represents a diazacarbocycle, such as a piperazine, e.g., substituted or unsubstituted.

In certain embodiments, X can be selected from —N(R$_8$)—, —O—, —S—, and a direct bond, Y can be selected from —C(=O)—, —C(=S)—, and —S(O$_2$)—, and Z can be selected from —N(R$_8$)—, —O—, —S—, and a direct bond, such that at least one of X and Z is present.

In certain embodiments R$_8$ represents H, lower alkyl, aralkyl, heteroaralkyl, aryl, or heteroaryl, e.g., H or lower alkyl.

In certain embodiments, X represents —NH—.

In certain embodiments, -L-X— represents -(unbranched lower alkyl)-NH—, e.g., —CH$_2$—NH—, —CH$_2$CH$_2$—NH—, etc.

In certain embodiments, the subject antagonists can be chosen on the basis of their selectively for the hedgehog pathway. This selectivity can be for the hedgehog pathway versus other pathways, or for selectivity between particular hedgehog pathways, e.g., e.g., ptc-1, ptc-2, etc.

In certain preferred embodiments, the subject inhibitors inhibit hedgehog-mediated signal transduction with an ED$_{50}$ of 1 mM or less, more preferably of 1 µM or less, and even more preferably of 1 nM or less.

In particular embodiments, the small molecule is chosen for use because it is more selective for one patched isoform over the next, e.g., 10 fold, and more preferably at least 100 or even 1000 fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a K$_i$ at least an order of magnitude lower than its K$_i$ for inhibition of PKC, preferably at least two orders of magnitude lower, even more preferably at least three orders of magnitude lower. In certain embodiments, the K$_i$ for PKA inhibition is less than 10 nM, preferably less than 1 nM, even more preferably less than 0.1 nM.

In certain embodiments, compounds useful in the present invention may be represented by general formula (IV):

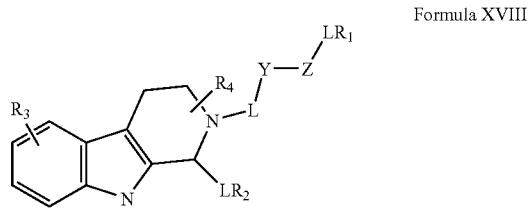

Formula XVIII wherein, as valence and stability permit,

R$_1$ and R$_2$, independently for each occurrence, represent H, substituted or unsubstituted lower alkyl, alkenyl, or alkynyl, —(CH$_2$)$_n$cycloalkyl (e.g., substituted or unsubstituted), —(CH$_2$)$_n$aryl (e.g., substituted or unsubstituted), or —(CH$_2$)$_n$ heterocyclyl (e.g., substituted or unsubstituted);

L, independently for each occurrence, is absent or represents —(CH$_2$)$_n$-alkyl, -alkenyl-, -alkynyl-, —(CH$_2$)$_n$alkenyl-, —(CH$_2$)$_n$alkynyl-, —(CH$_2$)$_n$O(CH$_2$)$_p$—, —(CH$_2$)$_n$NR$_2$(CH$_2$)$_p$—, —(CH$_2$)$_n$S(CH$_2$)$_p$—, —(CH$_2$)$_n$alkenyl(CH$_2$)$_p$—, —(CH$_2$)$_n$alkynyl(CH$_2$)$_p$—, —O(CH$_2$)$_n$—, —NR$_2$(CH$_2$)$_n$—, or —S(CH$_2$)$_n$—;

X and Z, independently, can be selected from —CH—, —N(R$_8$)—, —O—, —S—, or —Se—;

Y can be selected from —C(=O)—, —C(=S)—, —S(O$_2$)—, —S(O)—, —C(=NCN)—, or —P(=O)(OR$_2$)—;

R$_8$, independently for each occurrence, represents H, substituted or unsubstituted lower alkyl, —(CH$_2$)$_n$cycloalkyl (e.g., substituted or unsubstituted), —(CH$_2$)$_n$aryl (e.g., substituted or unsubstituted), —(CH$_2$)$_n$heterocyclyl (e.g., substituted or unsubstituted), or two R$_8$ taken together may form a 4- to 8-membered ring, e.g., with X$_1$ and Z$_1$ or X$_2$ and Z$_1$, which ring may include one or more carbonyls;

R$_3$ and R$_4$, independently represent from 1-4 substituents on the ring to which they are attached, selected from, independently for each occurrence, hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$;

p represents, independently for each occurrence, an integer from 0 to 10, preferably from 0 to 3; and n, individually for each occurrence, represents an integer from 0 to 10, preferably from 0 to 5.

In certain embodiments, R$_1$ and R$_2$ are independently selected from substituted or unsubstituted aryl, heterocyclyl, branched or unbranched alkyl, or cycloalkyl. In embodiments wherein R$_1$ or R$_2$ is aryl or heterocyclyl, substituents are preferably selected from H, alkyl, acyl, carboxy, ester, amide, cyano, ether, thioether, amino, halogen, nitro, and trihalomethyl.

In certain embodiments, R$_3$ is absent or represents one or two substituents selected from alkyl, acyl, carboxy, ester, amide, cyano, ether, thioether, amino, acyl, halogen, nitro, and trihalomethyl.

In certain embodiments, $R_4$ is absent or represents one or two substituents selected from ether, amino, thioether, alkyl, aryl, (=O), or carbonyl (e.g., carboxy, ester, ketone, aldehyde, etc.).

In certain embodiments, L is absent for each occurrence, or represents —$CH_2$— or —$CH_2CH_2$—

In certain embodiments, X represents $NR_8$. $R_8$ preferably represents H.

In certain embodiments, Z represents $NR_8$. $R_8$ preferably represents H.

In certain embodiments, Y represents —C(=O)—, —C(=S)—, or —S($O_2$)—.

Exemplary Compounds Part 4:

As described in further detail below, it is contemplated that the subject methods can be carried out using a variety of different small molecules which can be readily identified, for example, by such drug screening assays as described herein. For example, compounds useful in the subject methods include compounds may be represented by general formula (XVIII):

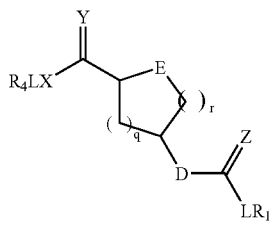

Formula XVIII wherein, as valence and stability permit, $R_1$, $R_2$, $R_3$, and $R_4$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —$(CH_2)_n$—, -alkenyl-, -alkynyl-, —$(CH_2)_n$alkenyl-, —$(CH_2)_n$alkynyl-, —$(CH_2)_nO(CH_2)_p$—, —$(CH_2)_nNR_8(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_8(CH_2)_n$—, or —$S(CH_2)_n$—;

X and D, independently, can be selected from —N($R_8$)—, —O—, —S—, —($R_8$)N—N($R_8$)—, —ON($R_8$)— or a direct bond;

Y and Z, independently, can be selected from O or S;

E represents O, S, or $NR_5$, wherein $R_5$ represents $LR_8$ or —C(=O)$LR_8$.

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring;

p represents, independently for each occurrence, an integer from 0 to 10, preferably from 0 to 3;

n, individually for each occurrence, represents an integer from 0 to 10, preferably from 0 to 5; and q and r represent, independently for each occurrence, an integer from 0-2.

In certain embodiments, D does not represent N-lower alkyl. In certain embodiments, D represents an aralkyl- or heteroaralkyl-substituted amine.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, Y and Z are O.

In certain embodiments, the sum of q and r is less than 4, e.g., is 2 or 3.

In certain embodiments, $XLR_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, E is $NR_8$. In certain embodiments, E represents an aralkyl- or heteroaralkyl-substituted amine, e.g., including polycyclic $R_8$.

In certain embodiments, X is not NH. In certain embodiments, X is included in a ring, or, taken together with —C(=Y)—, represents a tertiary amide.

In certain embodiments, compounds useful in the present invention may be represented by general formula (XIX):

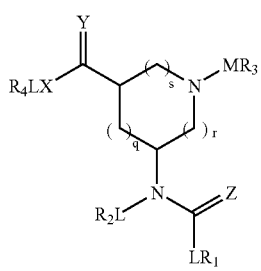

Formula XIX wherein, as valence and stability permit, $R_1$, $R_2$, $R_3$, $R_4$, $R_8$, L, X, Y, Z, n, p, q, and r are as defined above;

M is absent or represents L, —$SO_2$L-, or —(C=O)L-; and s represents, independently for each occurrence, an integer from 0-2.

In certain embodiments, Y and Z are O.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q, r, and s is less than 5, e.g., is 2, 3, or 4.

In certain embodiments, $XLR_4$, taken together, include a cyclic amine, such as a piperazine, a morpholine, a piperidine, a pyrrolidine, etc.

In certain embodiments, L attached to $R_1$ represents O, S, or $NR_8$, such as NH.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (XX):

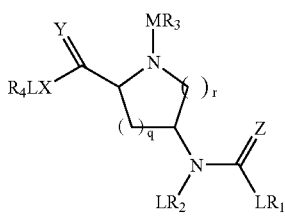

Formula XX wherein, as valence and stability permit, $R_1$, $R_2$, $R_3$, $R_4$, $R_8$, L, M, X, Y, Z, n, p, q, and r are as defined above.

In certain embodiments, Y and Z are O.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q and r is less than 4, e.g., is 2 or 3.

In certain embodiments, $XLR_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (XXI):

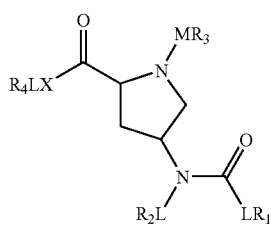

Formula XXI wherein, as valence and stability permit, $R_1$, $R_2$, $R_3$, $R_4$, $R_8$, L, M, X, n, and p are as defined above.

In certain embodiments, $XLR_4$, taken together, include a cyclic amine, such as a piperazine, a morpholine, a piperidine, a pyrrolidine, etc.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments L represents a direct bond for all occurrences.

In certain embodiments, compounds useful in the present invention may be represented by general formula (XXII):

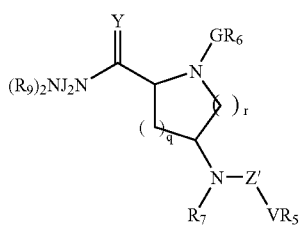

Formula XXII wherein, as valence and stability permit,

Y, n, p, q, and r are as defined above;

Z' represents —C(=O)—, —C(=S)—, —C(=NH)—, $SO_2$, or SO, preferably —C(=O)—, —C(=S)—;

V is absent or represents O, S, or $NR_8$;

G is absent or represents —C(=O)— or —$SO_2$—;

J, independently for each occurrence, represents H or substituted or unsubstituted lower alkyl or alkylene, such as methyl, ethyl, methylene, ethylene, etc., attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 7 members, which ring includes one or both occurrences of N;

$R_5$ represents substituted or unsubstituted alkyl (e.g., branched or unbranched), alkenyl (e.g., branched or unbranched), alkynyl (e.g., branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl, including polycyclic groups; and $R_7$ represents substituted or unsubstituted aryl, aralkyl, heteroaryl, or heteroaralkyl.

In certain embodiments, Y is O. In certain embodiments, Z' represents $SO_2$, —C(=O)—, or —C(=S)—.

In certain embodiments, the sum of q and r is less than 4.

In certain embodiments, $NJ_2N$, taken together, represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring that comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain embodiments, compounds useful in the present invention may be represented by general formula (XXIII):

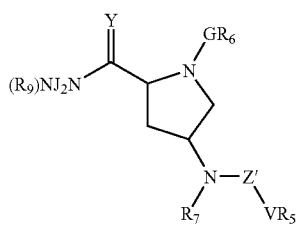

Formula XXIII wherein, as valence and stability permit, $R_5$, $R_6$, $R_7$, $R_8$, $R_9$, $R_{10}$, G, J, V, Y, Z', n, and p are as defined above.

In certain embodiments, Y is O. In certain embodiments, Z' represents $SO_2$, —C(=O)—, or —C(=S)—.

In certain embodiments, $NJ_2N$, taken together, represent a heterocyclic ring, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring that comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

Exemplary Compounds Part 5:

As described in further detail below, it is contemplated that the subject methods can be carried out using a variety of different small molecules which can be readily identified, for example, by such drug screening assays as described herein. For example, compounds useful in the subject methods include compounds may be represented by general formula (XXIV):

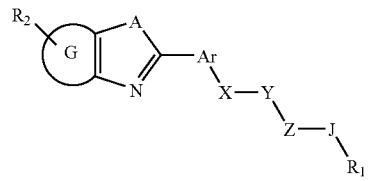

Formula XXIV wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O)—, $SO_2$, or —C(=S)—;

A represents O, S, or $NR_7$, preferably O or NH, and most preferably NH;

G represents a cycloalkyl, heterocyclyl, aryl, or heteroaryl ring fused to the ring to which it is attached, preferably an aryl or heteroaryl ring.

Ar represents a substituted or unsubstituted aryl or heteroaryl ring, such as a substituted or unsubstituted phenyl ring;

$R_1$ represents H or substituted or unsubstituted alkyl, alkenyl, alkynyl, aryl, heteroaryl, heterocyclyl, or cycloalkyl, including polycyclic groups;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes an aryl or heteroaryl ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the aryl or heteroaryl ring.

In certain embodiments, X and the ring comprising A are disposed on Ar in a meta (i.e., 1,3) relationship.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, compounds useful in the present invention may be represented by general formula (XXV):

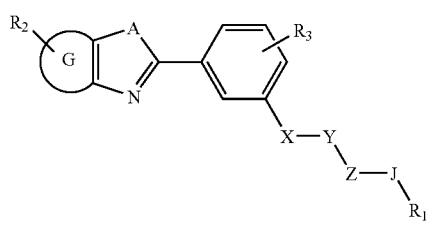

Formula XXV wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O)—, $SO_2$, or —C(=S)—;

A represents O, S, or N$R_7$, preferably O or NH, and most preferably NH;

G represents a cycloalkyl, heterocyclyl, aryl, or heteroaryl ring fused to the ring to which it is attached, preferably an aryl or heteroaryl ring.

$R_1$ represents H or substituted or unsubstituted alkyl, alkenyl, alkynyl, aryl, heteroaryl, heterocyclyl, or cycloalkyl, including polycyclic groups;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-NH$_2$, protected forms of the above, or any two $R_2$, when occurring more than once in a cyclic or polycyclic structure, can be taken together form a 4- to 8-membered cycloalkyl, aryl, or heteroaryl;

$R_3$ represents from 0-4 substituents on the ring to which it is attached, such as halogen, hydroxyl, alkoxy, amino, alkylamino, cyano, nitro, substituted or unsubstituted lower alkyl, and acyl, preferably halogen or substituted or unsubstituted lower alkyl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes an aryl or heteroaryl ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the aryl or heteroaryl ring.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, $R_3$ includes a substituent, such as a substituted or unsubstituted alkyl or a halogen, at a position para either to X or to the ring including A.

Antibodies as HH Antagonists

In one embodiment of the invention described herein, the agent to inhibit the Hh signaling pathway is an antibody or fragment thereof. One embodiment of the invention is an anti-Hh antibody raised against a Hh polypeptide that binds to a Hh polypeptide in competition with a Patched protein, a proposed Hh receptor. Antibodies useful in the present invention may be monoclonal or polyclonal antibodies. As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art. In addition, methods exist to produce monoclonal antibodies in transgenic animals or plants (Pollock et al., J. Immunol. Methods, 231: 147, 1999; Russell, Curr. Top. Microbiol. Immunol. 240:119, 1999).

In one embodiment, the portion of the antibody comprises a light chain of the antibody. As used herein, "light chain" means the smaller polypeptide of an antibody molecule composed of one variable domain (VL) and one constant domain (CL), or fragments thereof. In one embodiment, the portion of the antibody comprises a heavy chain of the antibody. As used herein, "heavy chain" means the larger polypeptide of an antibody molecule composed of one variable domain (VH) and three or four constant domains (CH1, CH2, CH3, and CH4), or fragments thereof. In one embodiment, the portion of the antibody comprises a Fab portion of the antibody. As used herein, "Fab" means a monovalent antigen binding fragment of an immunoglobulin that consists of one light chain and part of a heavy chain. In one embodiment, the portion of the antibody comprises a F(ab')$_2$ portion of the antibody. As used herein, "F(ab')2 fragment" means a bivalent antigen binding fragment of an immunoglobulin that consists of both light chains and part of both heavy chains. Fab and F(ab')2 can be obtained by brief pepsin digestion or recombinant methods. In one embodiment, the portion of the antibody comprises one or more CDR domains of the antibody. As used herein, "CDR" or "complementarity determining region" means a highly variable sequence of amino acids in the variable domain of an antibody, which directly interacts with the epitope of the antigen. Variable domains of an antibody also contain framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity-determining regions (CDR1 through CDR3). The CDRs, in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

The antibody may be a human or nonhuman antibody. The nonhuman antibody may be "humanized" by recombinant methods to reduce its immunogenicity in man. Methods for humanizing antibodies are known to those skilled in the art. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody.

Methods of humanization include, but are not limited to, those described in U.S. Pat. Nos. 4,816,567, 5,225,539, 5,585,089, 5,693,761, 5,693,762 and 5,859,205, which are hereby incorporated by reference. One of ordinary skill in the art will be familiar with other methods for antibody humanization.

Using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

RNA Interference as HH Antagonists

In one embodiment the Hh antagonists are RNA interference (RNAi) molecules. RNAi constructs comprise double stranded RNA that can specifically block expression of a target gene. Accordingly, RNAi constructs that specifically block expression of a gene that positively regulates the Hh signaling pathway can act as an antagonist of the Hh signaling pathway. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation; however, the biochemical mechanisms are currently an active area of research. Despite some uncertainty regarding the mechanism of action, RNAi provides a useful method of inhibiting gene expression in vitro or in vivo.

In preferred embodiments, hh RNAi antagonists of the invention are siRNA, either transcribed from a DNA vector encoding a short hairpin (stem-loop) siRNA, a synthetic siRNA, or longer dsRNA which can be further processed to shorter siRNA (such as 21-23 nucleotides), encoding sequences that interfere with the expression of positive control elements of the Hh signaling pathway, such as Hh itself or Smoothened.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 base pairs, or 1 in 10 base pairs, or 1 in 20 base pairs, or 1 in 50 base pairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Exemplary Targets of RNAi

The genes listed below are positive regulators of the Hh signaling pathway. Suppressing or negating their activities will result in inhibition of Hh signaling.

| Drosophila (Acc. No.) | Other Species (Acc. No.) |
|---|---|
| Hh (NM_079735) | Human Shh (NM_000193); human Ihh (XM_050846); human Dhh (NM_021044). mouse Shh (NM_009170); rat Shh (NM_017221); cow Shh (AF144100); house shrew Shh (AB081406); chicken Shh (L28099); Japanese firebelly newt Shh (D63339); bastard halibut Shh (AB029748); smaller spotted catshark Shh (AF393835); *Eleutherodactylus coqui* Shh (AF113403); Iberian ribbed newt Shh-related protein (AF003532); *Xenopus* Shh (L39213); *Takifugu rubripes* Shh (AJ507296); Zebrafish Shh (NM_131063); mouse Ihh (NM_010544.); rat Ihh (XM_237298); chicken Ihh (U58511); *Xenopus* banded HH (U26404); zebrafish Twhh (NM_131199). |
| Smo (NM_078719) | Human Smo (U84401); rat Smo (U84402); mouse Smo (XM_133018); *Xenopus* Smo (AF302766); zebrafish Smo (AF395809); chicken Smo (AF019977). |
| dlp (AF317090) | Human homolog (AF030186); mouse homolog (X83577); Rat homolog (L02896); Zebrafish homolog (AF354754); chicken homolog (L29089). |
| CG9211 (Protein: AAF52461; see AE003615 for nucleotide) | Human homolog (AY027658); Mouse homolog (AF388037); rat homolog (U68726); *Xenopus* homolog (AF388036); zebrafish homolog (AF461120). |
| Caup (X95178) | Human homolog (AF124733); mouse homolog (AF124732); *Xenopus* homolog (AF338157); chicken homolog (AF091504); zebrafish homolog (AY017309). |
| Ci (X54360) | Human Gli (NM_005269); human Gli2 (4 variants: NM_030379, NM_030380, NM_030381, NM_005270); human Gli3 (NM_000168); human Gli4 (NM_138465); Mouse Gli (NM_010296); rat Gli1 (XM_235221); horse Gli1 (AF510668); chicken Gli1 (U60762); *Xenopus* Gli1 (U57454); zebrafish Gli1 (NM_178296); mouse Gli2 (XM_196215); rat Gli2 (XM_222557); chicken Gli2 (AF022818); zebrafish Gli2 (AF085746); mouse Gli3 (NM_008130); rat Gli3 (XM_225412); chicken Gli3 (U60763); common quail Gli3 (AF231112); Xenopus Gli3 (U42461); eastern newt Gli3 (AF316110); *Xenopus* Gli4 (U42462). |
| Fu (Protein P23647, see X80468 for gene) | Human homolog (AF200815); Mouse homolog (AF195272, AK006827, AF124142); rat homolog (NM_019232, D49836); rabbit homolog (AF139639); *Xenopus* homolog (AF057138); spiny dogfish homolog (AJ223715); chicken homolog (AF039943); cow homolog (X61036); zebrafish homolog (BC052134). |

All Hh signaling pathway genes in various species can be routinely obtained from public and proprietary databases, such as GenBank, EMBL, FlyBase, to name but a few. In certain organisms, such as human and *Drosophila*, the whole genome is sequenced, and sequence comparison programs, such as the BLAST series of programs offered online at the NCBI website can be used to retrieve the most updated sequences of any known Hh signaling pathway genes. The following table list several representative members of the known Hh signaling pathway genes in various species. It is by no means exhaustive, and should not be viewed as limiting in any sense. Rather, it serves as a useful starting point for an exhaustive search, which a skilled artisan would be able to perform these searches using routine biotechniques. Some genes may have several different database entries with different accession numbers, but are nonetheless same or almost the same in sequence. Regardless, only one entry for each gene is provided in the table above.

Exemplary RNAi Constructs

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNA are double stranded, and may include short overhangs at each end. Preferably, the overhangs are 1-6 nucleotides in length at the 3' end. It is known in the art that the siRNAs can be chemically synthesized, or derived from a longer double-stranded RNA or a hairpin RNA. The siRNAs have significant sequence similarity to a target RNA so that the siRNAs can pair to the target RNA and result in sequence-specific degradation of the target RNA through an RNA interference mechanism. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine is tolerated and does not affect the efficiency of RNAi. The absence of a 2' hydroxyl significantly enhances the nuclease resistance of the overhang in tissue culture medium and may be beneficial in vivo.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

In certain embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (i.e., hairpin RNA). The hairpin RNAs can be synthesized exogenously or can be formed by transcribing from RNA polymerase III promoters in vivo.

Examples of making and using such hairpin RNAs for gene silencing in mammalian cells are described in, for example, Paddison et al. (2002) *Genes Dev.*, 16:948-58; McCaffrey et al. (2002) *Nature*, 418:38-9; McManus et al., (2002) *RNA*, 8:842-50; Yu et al. (2002) *Proc. Natl. Acad. Sci. USA*, 99:6047-52). Preferably, such hairpin RNAs are engineered in cells or in an animal to ensure continuous and stable suppression of a desired gene. It is known in the art that siRNAs can be produced by processing a hairpin RNA in the cell.

Preparation of RNAi Constructs

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc. Natl. Acad. Sci. USA*, 98:9742-9747; Elbashir, et al. (2001) *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The double-stranded structure may be formed by a single self-complementary RNA strand or two complementary RNA strands. RNA duplex formation may be initiated either inside or outside the cell.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res.*, 25:776-780; Wilson et al. (1994) *J. Mol. Recog.*, 7:89-98; Chen et al. (1995) *Nucleic Acids Res.*, 23:2661-2668; Hirschbein et al. (1997) *Antisense Nucleic Acid Drug Dev.* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, α-configuration).

Delivery of RNAi Constructs

The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional (or convergent) transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell. Also see Tran et al., (2003) *BMC Biotechnology* 3: 21 (incorporated herein by reference).

HH Antagonist Compositions

One aspect of the present invention provides pharmaceutical compositions comprising an antagonist of the Hh signaling pathways. The pharmaceutical compositions comprise an antagonist of Hh activity, which may be a small molecule of less than 2000 daltons, a Hh antibody, a Smoothened antibody, a mutant Hh protein that binds to a physiological target of an Hh polypeptide without invoking the physiological response normally induced by a functional Hh polypeptide, an antisense nucleic acid against the members of the Hh signaling pathway, an RNAi construct to inhibit the Hh signaling pathway, and a ribozyme. The pharmaceutical compositions may also comprise an agonist of the negative regulatory elements of the Hh signaling pathway. The pharmaceutical compositions may further comprise additional therapeutic agents, such as additional HH activity-lowering drugs.

In still another aspect, the invention relates to a method for preparing a pharmaceutical composition, comprising combining a Hh antagonist, optionally an additional pharmaceutically active component, and a pharmaceutically acceptable excipient in a composition for simultaneous administration of the drugs.

This invention provides such agents described herein, and the pharmaceutical compositions may additionally comprise pharmaceutically acceptable carriers. Pharmaceutically acceptable carriers are well known to those skilled in the art. Such pharmaceutically acceptable carriers may include but are not limited to a diluent, an aerosol, a topical carrier, an aqueous solution, a non-aqueous solution or a solid carrier.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

For embodiments wherein the agents are polypeptides and antibodies, the pharmaceutical composition may be formulated for administration with a biologically acceptable medium, such as water, buffered saline, polyol (for example, glycerol, propylene glycol, liquid polyethylene glycol and the like) or suitable mixtures thereof. In preferred embodiments, the polypeptide is dispersed in lipid formulations, such as micelles, which closely resemble the lipid composition of natural cell membranes to which the protein is to be delivered. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the Hh signaling pathway agonist, its use in the pharmaceutical preparation of the invention is contemplated. Suitable vehicles and their formulation inclusive of various proteins are described, for example, in the book *Remington's Pharmaceutical Sciences* (Mack Publishing Company, Easton, Pa., USA 1985) or *Handbook of Pharmaceutical Excipients*, 4$^{th}$ ed. (Ed. Rowe et al., Pharmaceutical Press, Grayslake, Ill., USA 2003), the contents of which are incorporated herein by reference.

For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the proteins of the invention are formulated into ointments, salves, gels, or creams as generally known in the art.

In accordance with the subject method, expression constructs of the subject polypeptides (and endothelialization polypeptide as appropriate) may be administered in any biologically effective carrier, e.g. any formulation or composition capable of effectively transfecting cells in vivo with a recombinant fusion gene. Approaches include insertion of the subject fusion gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

The optimum concentration of the agent(s) in the chosen medium can be determined empirically, according to procedures well known to medicinal chemists.

Gene Therapy using HH Antagonists

One aspect of the present invention provides for methods of treatment using gene therapy. As used herein, "gene therapy" refers to a therapeutic introduction of nucleic acid into a subject cell so that the nucleic acid may be expressed, resulting in alleviation of ailment.

In another preferred embodiment, the invention feature a nucleic acid which encodes a polypeptide that antagonizes the biological activity of a Hh polypeptide, which nucleic acid comprises variation of the nucleotide sequence designated by one of SEQ ID No:1, SEQ ID No:2, SEQ ID No:3, SEQ ID No:4, SEQ ID No:5, SEQ ID No:6, SEQ ID No:7, SEQ ID No:8, or SEQ ID No:9. Preferably, the nucleic acid comprises a variant of Hh-encoding portion that hybridizes under stringent conditions to a coding portion of one or more of the nucleic acids designated by SEQ ID No:1-9. Another preferred embodiment is a nucleic acid which encodes a Patched polypeptide.

The term "equivalent" is understood to include nucleotide sequences encoding polypeptides with similar binding capacities and resulting in the same or similar effect on the regulation of the Hh signaling pathway. Thus, an equivalent nucleotide sequence of a mutant Hh polypeptide desirable to conduct the methods of the present invention will act as an inhibitor of Hh signaling, possibly by binding to a physiological receptor of a Hh polypeptide but failing to invoke the physiological response induced by active Hh polypeptide. An equivalent will include sequences that differ by one or more nucleotide substitutions, additions or deletions, such as allelic variants; and will, therefore, include sequences that differ from the nucleotide sequence of the vertebrate hh cDNAs shown in SEQ ID Nos:1-9. The sequence may further differ due to the degeneracy of the genetic code.

Preferred nucleic acids for use in gene therapy of the present invention encode a mutant of a vertebrate Hh polypeptide lacking the normal Hh activity. Such mutant polypeptide comprises an amino acid sequence at least 60%, 70%, 80%, 90%, or even 95% homologous with an amino acid sequence selected from SEQ ID Nos:10-18, but without the physiological activity of a Hh polypeptide are also within the scope of the invention. Preferably, the nucleic acid includes a portion of the nucleotide sequence corresponding to the coding region of SEQ ID Nos:1-9, which has substitution, deletion, inversion, truncation, or other mutation so that the polypeptide encoded by such coding sequence does not have Hh activity.

With respect to functionally equivalent fragments of sonic clones, a preferred nucleic acid encodes a polypeptide including a Hh portion having molecular weight of approximately 19 kDa and which polypeptide can antagonize a Hh biological activity. Preferably, the polypeptide encoded by the nucleic acid comprises an amino acid sequence homologous to an amino acid sequence designated in one of SEQ ID No:10, SEQ ID No:11, SEQ ID No:12, SEQ ID No:13, SEQ ID No:14, SEQ ID No:15, SEQ ID No:16, SEQ ID No:17, or SEQ ID No:18.

A preferred nucleic acid encodes a mutant Hh polypeptide comprising a variation of an amino acid sequence represented by the formula A-B wherein, A represents all or the portion of the amino acid sequence designated by residues 1-168 of SEQ ID No:21; and B represents at least one amino acid residue of the amino acid sequence designated by residues 169-221 of SEQ ID No:21; wherein A and B together represent a contiguous polypeptide sequence designated by SEQ ID No:21. Preferably, B can represent at least five, ten or twenty amino acid residues of the amino acid sequence designated by residues 169-221 of SEQ ID No:21.

To further illustrate, another preferred nucleic acid encodes a mutant polypeptide comprising a variation of an amino acid sequence represented by the formula A-B, wherein A represents all or the portion of the amino acid sequence designated by residues 24-193 of SEQ ID No:15; and B represents at least one amino acid residue of the amino acid sequence designated by residues 194-250 of SEQ ID No:15; wherein A and B together represent a contiguous polypeptide sequence designated in SEQ ID No:15, and the polypeptide antagonizes the biological activity of a Hh polypeptide.

Yet another preferred nucleic acid encodes a mutant polypeptide comprising a variant of an amino acid sequence represented by the formula A-B, wherein A represents all or the portion, e.g., 25, 50, 75 or 100 residues, of the amino acid sequence designated by residues 25-193, or analogous residues thereof, of a vertebrate Hh polypeptide identical or homologous to SEQ ID No:13; and B represents at least one amino acid residue of the amino acid sequence designated by residues 194-250, or analogous residues thereof, of a vertebrate Hh polypeptide identical or homologous to SEQ ID No:13; wherein A and B together represent a contiguous polypeptide sequence designated in SEQ ID No:13.

Another preferred nucleic acid encodes a polypeptide comprising an amino acid sequence represented by the formula A-B, wherein A represents all or the portion, e.g., 25, 50, 75 or 100 residues, of the amino acid sequence designated by residues 23-193 of SEQ ID No:11; and B represents at least one amino acid residue of the amino acid sequence designated by residues 194-250 of SEQ ID No:11; wherein A and B together represent a contiguous polypeptide sequence designated in SEQ ID No:11, and the polypeptide antagonizes the biological activity of a Hh polypeptide.

Another preferred nucleic acid encodes a polypeptide comprising an amino acid sequence represented by the formula A-B, wherein A represents all or the portion, e.g., 25, 50, 75 or 100 residues, of the amino acid sequence designated by residues 28-197 of SEQ ID No:12; and B represents at least one amino acid residue of the amino acid sequence designated by residues 198-250 of SEQ ID No:12; wherein A and B together represent a contiguous polypeptide sequence designated in SEQ ID No:12, and the polypeptide antagonizes the biological activity of a Hh polypeptide.

Yet another preferred nucleic acid encodes a mutant polypeptide comprising a variation of an amino acid sequence represented by the formula A-B, wherein A represents all or the portion, e.g., 25, 50 or 75 residues, of the amino acid sequence designated by residues 1-98, or analogous residues thereof, of a vertebrate Hh polypeptide identical or homologous to SEQ ID No:18; and B represents at least one amino acid residue of the amino acid sequence designated by residues 99-150, or analogous residues thereof, of a vertebrate Hh polypeptide identical or homologous to SEQ ID No:18; wherein A and B together represent a contiguous polypeptide sequence designated in SEQ ID No:18.

Another aspect of the invention provides a nucleic acid which hybridizes under high or low stringency conditions to a nucleic acid represented by one of SEQ ID Nos:1-9. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

The mutant polypeptides that inhibit or antagonize Hh activities can be selected from these sequences using protocols well known in the art to screen a combinatorial expression library.

A preferred approach for in vivo introduction of nucleic acid encoding one of the subject polypeptides into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a CKI polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject proteins, it is important to note that a prerequisite for the successful infection of target cells by most retroviruses, and therefore of stable introduction of the recombinant gene, is that the target cells must be dividing. Such limitation on infection can be beneficial when the tissue surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) Proc. Nat. Acad. Sci. USA 86:9079-9083; Julan et al. (1992) J. Gen. Virol. 73:3251-3255; and Goud et al. (1983) Virology 163:251-254); or coupling cell surface ligands to the viral env proteins (Neda et al. (1991) J. Biol. Chem. 266:14143-14146). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the fusion gene of the retroviral vector.

Another viral vector system useful for delivery of the subject polypeptides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics Microbiol. Immunol. 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see, for example, Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) BioTechniques 6:616; Rosenfeld et al. (1991) Science 252:431-434; and Rosenfeld et al. (1992) Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting non-dividing cells and can be used to infect a wide variety of cell types, including endothelial cells (Lemarchand et al. (1992) Proc. Natl. Acad. Sci. USA 89:6482-6486), and smooth muscle cells (Quantin et al. (1992) Proc. Natl. Acad. Sci. USA 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109-127). Expression of the inserted fusion gene can be under control of, for example, the E1A promoter, the major late promoter (MLP) and associated leader sequences, the E3 promoter, or exogenously added promoter sequences.

Other viral vector systems that may have application in gene therapy have been derived from herpes virus, Vaccinia virus, and several RNA viruses. In particular, herpes virus vectors may provide a unique strategy for persistent expression of the subject fusion proteins in cells of the central nervous system and ocular tissue (Pepose et al. (1994) Invest. Ophthalmol. Vis. Sci. 35:2662-2666)

In addition to viral transfer methods, such as those illustrated above, non-viral methods can also be employed to cause expression of the subject proteins in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding one of the subject proteins can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via receptor-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260-926; Wagner et al. (1992) *Proc. Nat. Acad. Sci. USA* 89:7934; and Christiano et al. (1993) *Proc. Nat. Acad. Sci. USA* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *Proc. Nat. Acad. Sci. USA* 91: 3054-3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g., retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinaceous biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

V. Exemplary ptc Agonist/Antagonist Compounds

In another embodiment, the subject method is carried out using a ptc agonist/antagonist composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly their role in the pathogenesis of peripheral nerve proliferation and/or differentiation. In one embodiment, the assay evaluates the ability of a compound to modulate binding between a hedgehog polypeptide and a hedgehog receptor such as patched. In other embodiments, the assay merely scores for the ability of a test compound to alter the signal transduction acidity of the patched protein. In this manner, a variety of hedgehog and/or ptc therapeutics, both agonists and antagonist can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Accordingly, in an exemplary screening assay for ptc agonists/antagonists, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc antagonist of the present invention is one which disrupts the association of patched with smoothened.

Agonist and antagonists of peripheral nerve maintenance can be distinguished, and the efficacy of the compound can be assessed, by subsequent testing with T lymphocytes, e.g., in culture.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from *drosophila* (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein—which are also potential antagonists of hedgehog-dependent signal transduction). For instance, the patched protein can be provided in soluble form, as for example a preparation of one of the extracellular domains, or a preparation of both of the extracellular domains which are covalently connected by an unstructured linker (see, for example, Huston et al. (1988) *PNAS* 85: 4879; and U.S. Pat.

No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) *Development* 122: 1225-1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habig et al (1974) *J Biol Chem* 249: 7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266: 21150-21157) which includes a 10-residue sequence from c-myc, as well as the pFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68: 809-818; Newton et al. (1983) *Biochemistry* 22: 6110-6117; and Reber et al. (1987) *J Biol Chem* 262: 11369-11374).

In addition to cell-free assays, such as described above, the readily available source of hedgehog proteins provided by the art also facilitates the generation of cell-based assays for identifying small molecule agonists/antagonists and the like. Analogous to the cell-based assays described above for screening combinatorial libraries, cells which are sensitive to hedgehog induction, e.g. patched-expressing cells or other myoblast-derived cells sensitive to hedgehog induction, can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In other embodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or antagonists of hedgehog binding. Binding assays can be performed using whole cells. Furthermore, the recombinant cells of the present invention can be engineered to include other heterolgous genes encoding proteins involved in hedgehog-dependent signal pathways. For example, the gene products of one or more of smoothened, costal-2 and/or fused can be co-expressed with patched in the reagent cell, with assays being sensitive to the functional reconstitution of the hedgehog signal transduction cascade.

Alternatively, liposomal preparations using reconstituted patched protein can be utilized. Patched protein purified from detergent extracts from both authentic and recombinant origins can be reconstituted in artificial lipid vesicles (e.g. phosphatidylcholine liposomes) or in cell membrane-derived vesicles (see, for example, Bear et al. (1992) *Cell* 68: 809-818; Newton et al. (1983) *Biochemistry* 22: 6110-6117; and Reber et al. (1987) *J Biol Chem* 262: 11369-11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists or antagonists, of hedgehog or patched activities. By detecting changes in intracellular signals, such as alterations in second messengers or gene expression, in patched-expressing cells contacted with a test agent, candidate agonists and antagonists to patched signaling can be identified.

A number of gene products have been implicated in patched-mediated signal transduction, including patched, the transcription factor cubitus interruptus (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 Development 110, 291-301; Marigo et al., 1996) and the vertebrate homologs of the *drosophila* cubitus interruptus gene, the GLI genes (Hui et al. (1994) *Dev Biol* 162: 402-413). Patched gene expression has been shown to be induced in cells of the limb bud and the neural plate that are responsive to Shh. (Marigo et al. (1996) PNAS, in press; Marigo et al. (1996) *Development* 122: 1225-1233). The GLI genes encode putative transcription factors having zinc finger DNA binding domains (Orenic et al. (1990) *Genes & Dev* 4: 1053-1067; Kinzler et al. (1990) *Mol Cell Biol* 10: 634-642). Transcription of the GLI gene has been reported to be upregulated in response to hedgehog in limb buds, while transcription of the GLI3 gene is downregulated in response to hedgehog induction (Marigo et al. (1996) *Development* 122: 1225-1233). By selecting transcriptional regulatory sequences from such target genes, e.g. from patched or GLI genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of ptc induction of differentiation/quiescence.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270: 10314-10322; and Kube et al. (1995) *Cytokine* 7: 1-7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsice to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc agonist/antagonist.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7: 725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216: 362-368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) Genes & Dev 10: 647). High PKA activity has been shown to antagonize hedgehog signaling in these systems. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc agonist/antagonist can be a 5-isoquinolinesulfonamide, such as represented in the general formula:

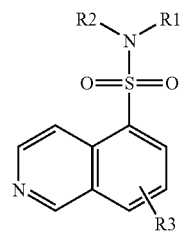

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-O-$lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-$O-lower alkyl, $-(CH_2)_m-$O-lower alkenyl, $-(CH_2)_n-$O$-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

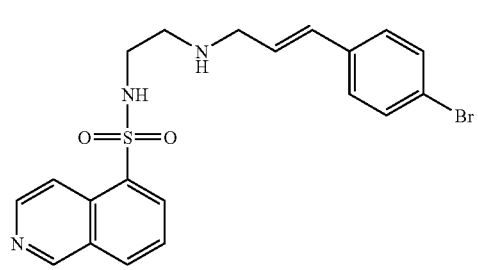

In another embodiment, the PKA inhibitor is 1-(5-isoquinolinesulfonyl)-2-methylpiperazine (H-7; Calbiochem Cat. No. 371955), e.g., having the formula:

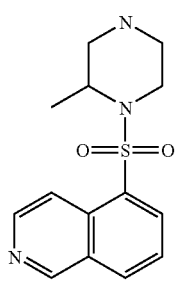

In still other embodiments, the PKA inhibitor is KT5720 (Calbiochem Cat. No. 420315), having the structure

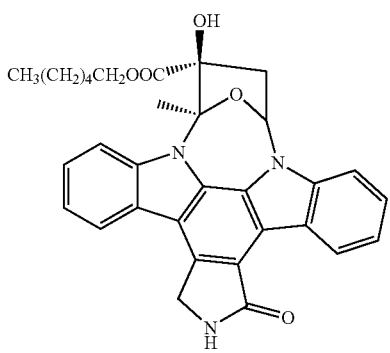

A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

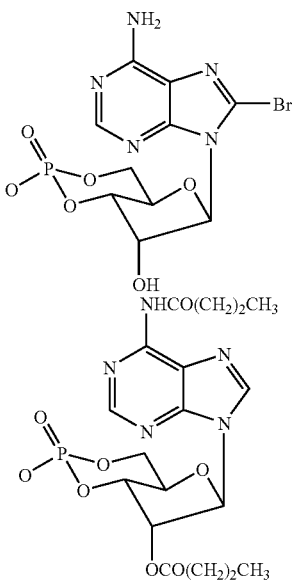

Exemplary peptidyl inhibitors of PKA activity include the PKA Heat Stable Inhibitor (isoform α; see, for example, Calbiochem Cat. No. 539488, and Wen et al. (1995) *J Biol Chem* 270: 2041).

Certain hedgehog receptors may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84: 45-56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87-89; Therond et al. 1993, *Mech. Dev.* 44. 65-80). The ability of compounds to modulate serine/threonine kinase activation could be screened using colony immunoblotting (Lyons and Nelson (1984) *Proc. Natl. Acad. Sci. USA* 81: 7426-7430) using antibodies against phosphorylated serine or threonine residues. Reagents for performing such assays are commercially available, for example, phosphoserine and phosphothreonine specific antibodies which measure increases in phosphorylation of those residues can be purchased from commercial sources.

In yet another embodiment, the ptc agonist/antagonist is an antisense molecule which inhibits expression of a protein involved in a patched-mediated signal transduction pathway. To illustrate, by inhibiting the expression of a protein which are involved in patched signals, such as fused, costal-2, smoothened and/or Gli genes, the ability of the patched signal pathway(s) to inhibit proliferation of a cell can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6: 958-976; and Stein et al. (1988) *Cancer Res* 48: 2659-2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25-26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc agonist/antagonist can be an antisense construct for inhibiting the expression of patched, e.g., to mimic the inhibition of patched by hedgehog. Exemplary antisense constructs include:

```
5'-GTCCTGGCGCCGCCGCCGCCGTCGCC     (SEQ ID NO: 26)

5'-TTCCGATGACCGGCCTTTCGCGGTGA     (SEQ ID NO: 27)

5'-GTGCACGGAAAGGTGCAGGCCACACT     (SEQ ID NO: 28)
```

VI. Exemplary Pharmaceutical Preparations of Hedgehog and ptc Agonists/Antagonists The source of the hedgehog and ptc agonists/antagonists to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating peripheral neuropathies can determine the effective amount of an hedgehog or ptc agonist/antagonist to be formulated in a pharmaceutical or cosmetic preparation.

The hedgehog or ptc agonist/antagonist formulations used in the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc agonist/antagonist as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeutics, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the subject compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications which can be considered cosmetic uses. Cosmetic compositions known in the art, preferably hypoallergenic and pH controlled are especially preferred, and include toilet waters, packs, lotions, skin milks or milky lotions. The preparations contain, besides the hedgehog or ptc agonist/antagonist, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc agonist/antagonist, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2-15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10-50% of oil, 1 to 10% of surfactant, 50-80% of water and 0 to 3% of preservative and/or perfume. In the aforementioned preparations, all % symbols refer to weight by weight percentage.

Particular compositions for use in the method of the present invention are those wherein the hedgehog or ptc agonist/antagonist is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc agonist/antagonist, such as an organic mimetic, is predominantly incorporated into the lipid layers, although polar head groups may protrude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc agonists/antagonists is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc agonist/antagonist can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of a hedgehog or ptc agonist/antagonist. In some cases use may be made of plasters, bandages, dressings, gauze pads and the like which have been impregnated with a topical formulation containing the therapeutic formulation.

EXAMPLES

The invention now being generally described, it will be more readily understood by reference to the following examples which are included merely for purposes of illustration of certain aspects and embodiments of the present invention, and are not intended to limit the invention.

Example 1

Evaluation of the Effects of Hedgehog on T-cell Developmentin FTOC

Utilizing a fetal thymic organ culture (FTOC), the effects of Shh on T-cell maturation was determined. Briefly, immature thymocytes (CD4$^-$/CD8$^-$ [DN]) were isolated from E14 thymus. The cells were culture for about 7 days, and the level of mature thymocytes, e.g., CD4$^+$/CD8$^+$ [DP], was assessed. In certain cultures, octyl-modified Shh was added to the culture; in other cultures, the anti-hedgehog 5E1 antibody was added. As illustrated in FIGS. 1-4, the addition of high dose of Shh (0.5 µg/ml) to the culture resulted in an increase in the percentage of cells after 7 days with markers indicative of immature thymocytes. Conversely, addition of the 5E1 antibody resulted in an increase in the percentage of mature T lymphocytes after 7 days.

Example 2

Evaluation of the Effects of Hedgehog on T-cell Developmentin in Shh$^{-/-}$ Mice Thymus Size is Reduced in Shh–/– Embryos In order to provide genetic evidence for a role for Shh in the control of T cell development, we studied Shh$^{-/-}$ embryos. The thymus lobes of Shh–/– embryos were smaller than those of Shh$^{+/-}$ or wildtype littermates in all litters examined (FIG. 5$a$)

Shh Regulates Thymocyte Development from DN1 to DN2

To provide genetic evidence for a role for Shh in the control of Tcell development, we analysed thymocyte development in Shh–/–, +/– and +/+ littermates. On E13.5, thymocyte numbers were reduced by between 17- and 6-fold (FIG. 5$b$). Given the reduction in cell numbers, the thymocyte population was difficult to identify by side scatter profile. Therefore, we stained cells with anti-CD45, anti-CD25 and anti-CD44, and analysed thymocyte development by gating on the CD45$^+$ population. The percentage of cells within the live gate that expressed the lymphocyte lineage marker CD45 was reduced in the Shh–/– embryos to about 20% compared to about 80% in littermate thymi (FIGS. 5$c$ and 5$d$). Thus, the E13.5 Shh–/– thymus contained fewer lymphocyte lineage cells than its littermates, suggesting that progenitor cells were either less efficient at colonising the thymus or were not expanding on entry into the thymus.

We found an increase in the proportion of CD44$^+$CD25$^-$ DN1 cells and decrease in the proportion of CD44$^+$CD25$^+$ DN2 cells in the Shh–/– thymi compared to that of +/– and +/+ littermates (FIG. 5$d$). In a typical experiment, 81.9% of Shh–/– thymocytes were in the DN1 population, compared to 35.5% and 38% of thymocytes from +/– and +/+ littermates respectively. This reduction in DN2 cells was observed in all litters examined (FIG. 5$e$). The DN1 population is not fully committed to the T cell lineage, but contains cells that are capable of differentiating into T, B, NK and dendritic cell lineages (Akashi et al., 2000; Kawamoto et al., 2000). Thus, our data indicate a reduction in T-cell lineage commitment in Shh–/– embryos on E13.5. Interestingly, in wildtype mice the DN2 population express high levels of the Hh signalling molecule Smo at their cell surface (Outram et al., 2000), and cell surface Smo is upregulated in response to Hh signalling (Denef et al., 2000).

It seems possible that the accumulation of CD44$^+$CD25$^-$ cells in the Shh–/– thymus was also the result of a failure of T lineage commitment, and that these cells were not true DN1 cells. To test this, we analyzed the expression of CD117 and B220 on the CD44$^+$ DN thymocyte population from E13.5 embryos. More than 97% of CD44$^+$ thymocytes from Shh–/– embryos stained positively with anti-CD117, suggesting that this population was equivalent to the most immature thymocyte population found in normal mice. There was no difference in B220 expression on the CD44$^+$CD25$^-$ DN population between Shh–/– and littermate thymi. The expressions of NK1.1 and TCRγδ were also very similar in Shh–/– and littermate thymocytes.

Thus, the reduction in DN2 cells could either be due to a failure of the DN1 population to differentiate to DN2 or be because the DN2 cells were failing to survive. To test this, we analysed cell death in the DN2 population by Annexin-V staining. There was no difference in the proportion of apoptotic cells between +/+ and –/– thymi (FIG. 5$f$). Thus, the reduction in DN2 cells was because the Shh–/– thymocytes were not efficiently making the transition from DN1 to DN2 (reduced differentiation).

Shh Regulates Proliferation of DN Thymocytes

When we analysed thymocyte development on E14.5 and E15.5, we found that Shh–/– thymocyte numbers were still greatly reduced in all litters examined (FIG. 6$a$). On E14.5 (FIG. 6$b$) and E15.5 (data not shown), all DN subsets were present in the Shh–/– thymus. The proportion of Shh–/– thymocytes that expressed CD25 had increased, confirming that CD25$^+$ cells could expand, survive and accumulate, but was still reduced compared with that in +/+ littermates on E14.5 and E15.5 (FIG. 6$c$). On E15.5, CD8$^+$ ISPs and DP cells had not yet appeared (data not shown).

Figure 6A:
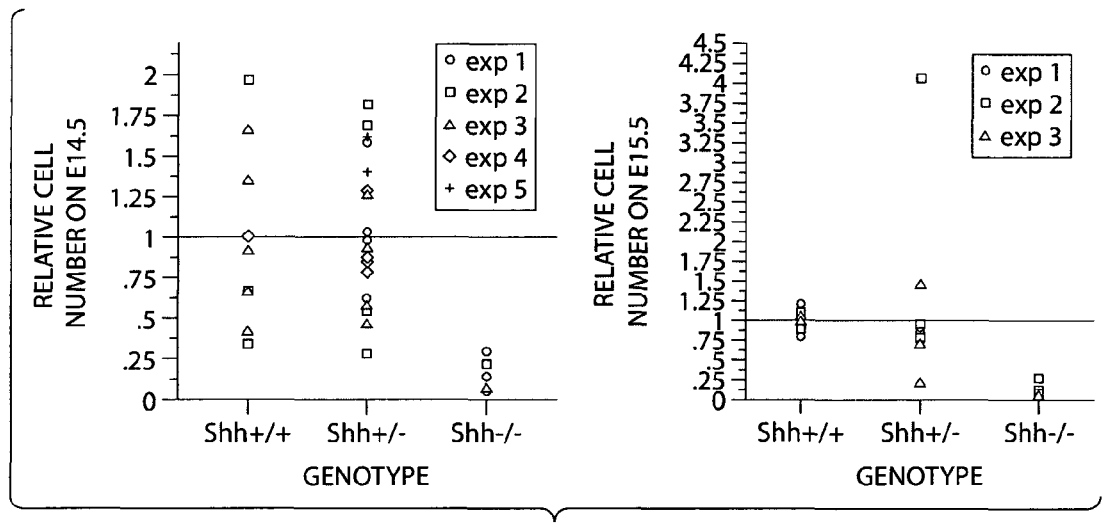
FIG. 6 Reduced thymus cellularity and differentiation on E14.5 and E15.5. (A) Thymus cellularity on E14.5 (left panel) and on E15.5 (right panel). To allow comparison between litters, cell numbers relative to control were calculated as in FIG. 4. The differences in cellularity between Shh−/− and Shh+/+ thymi were statistically significant by Students t-test (p=0.0016 for E14.5, p=<0.0001 for E15.5). (B) Composition of DN subsets on E14.5 in Shh+/+, +/− and −/−, gated on CD45.2 and stained with anti-CD44 and anti-CD25. The percentage of cells in each quadrant is given. Mean thymus size was ($\times 10^{-4}$), +/+1.1, +/−1.1 and −/−0.24. (C) The relative percentage of CD25$^+$ cells on E14.5 (left panel) and E15.5 (right panel). Relative percentages were calculated to allow comparison between litters, as in FIG. 4. The differences in percentage of CD25$^+$ cells between Shh−/− and control thymi were statistically significant by Students t-test (p=0.0037 for E14.5, P=0.0446 for E15.5). (D) Cell cycle status of thymocytes from Shh+/+, +/− and − embryos on E14.5. Permeabilised cells were stained with propidium iodide. The percentage of cells in the marker (G2+S) is given.
Figure 6B:
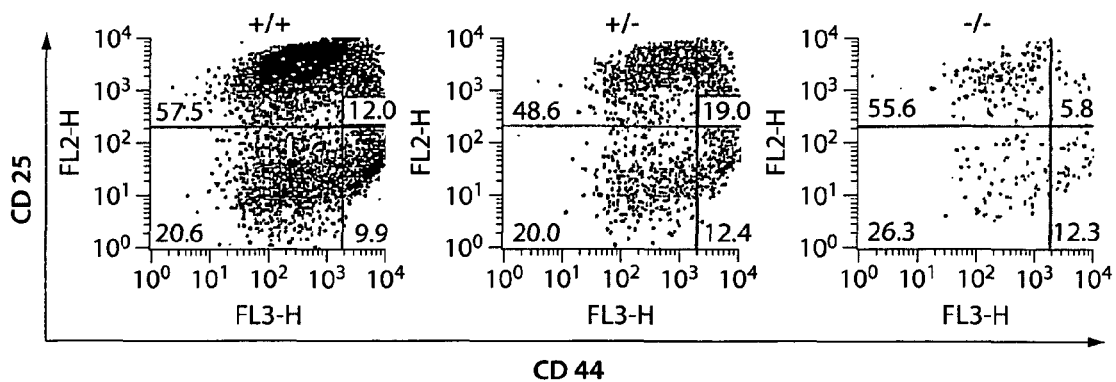
Figure 6C:
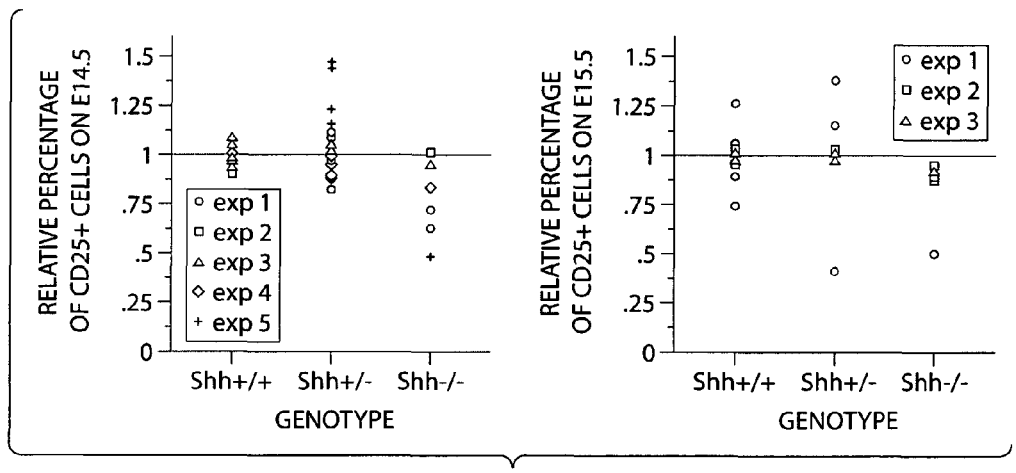
Figure 6D:
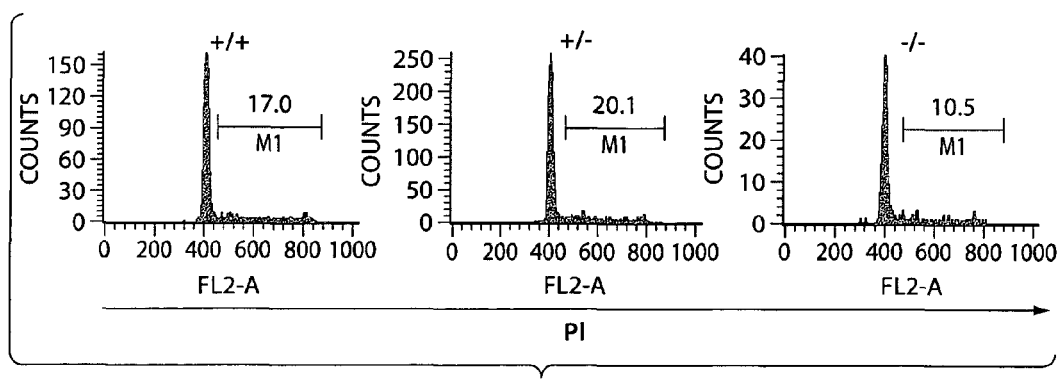

The reduction in thymocyte numbers in the Shh−/− thymus suggests that Shh provides a signal for thymocyte proliferation. Therefore, we analysed the cell cycle status of E14.5 Shh−/− thymocytes. Propidium iodide staining indicated that 10.5% of Shh−/− thymocytes were in the G2 and S phases of the cell cycle, compared to 17% and 20% of Shh+/+ and +/− littermate thymocytes respectively (FIG. 6d). Thus, in addition to its role in promoting differentiation to DN2, Shh promotes DN thymocyte proliferation.

Reduced Production of DP Thymocytes in the Shh−/− Thymus

Figure 7A:
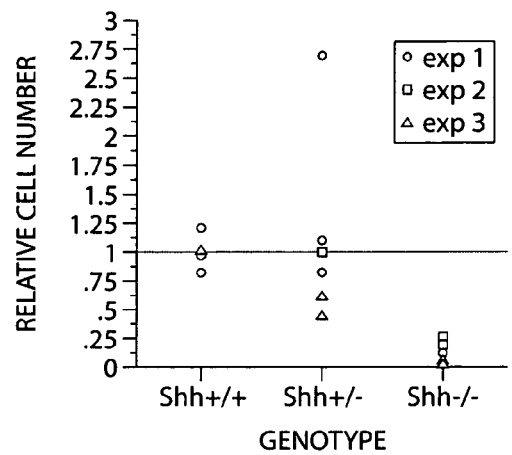
FIG. 7 Reduction in DP cells and cellularity in E16.5 Shh−/− thymus. (A) Thymus cellularity relative to control on E16.5. To allow comparison between litters, the relative number of cells per thymus was calculated as in FIG. 5. The difference in cellularity between Shh−/− and control thymi was statistically significant by Students t-test (p=<0.0001). (B) Flow cytometry of E16.5 thymus stained with anti-CD4 and anti-CD8. The percentage of cells in each quadrant is given. Mean thymus size was ($\times 10^{-5}$), +/+5.5, +/−3.0 and −/−0.18. (C) The relative percentage of DP cells in E16.5 thymi. To allow comparison between litters, the percentage of DP cells recovered in each embryonic thymus was divided by the mean percentage of DP cells in control thymi from the same litter. The difference in percentage of DP cells between Shh−/− and control thymi was statistically significant by Students t-test (p=0.001). (D) Annexin-V staining on DP cells from +/+, +/− and −/− littermates. Cells were stained with anti-CD4, anti-CD8 and Annexin-V, and Annexin-V staining gated on the DP cells is shown. The percentage of cells within the marker is given. (E) Annexin-V staining on DN4 cells from +/+, +/− and −/− littermates. Cells were stained with anti-CD4, anti-CD8, anti-CD25, anti-CD44, anti-TCRβ and Annexin-V, and Annexin-V staining gated on the DN4 cells (CD4−, CD8−, CD25−, TCRβ−, CD44−) is shown. The percentage of cells within the marker is given.
Figure 7B:
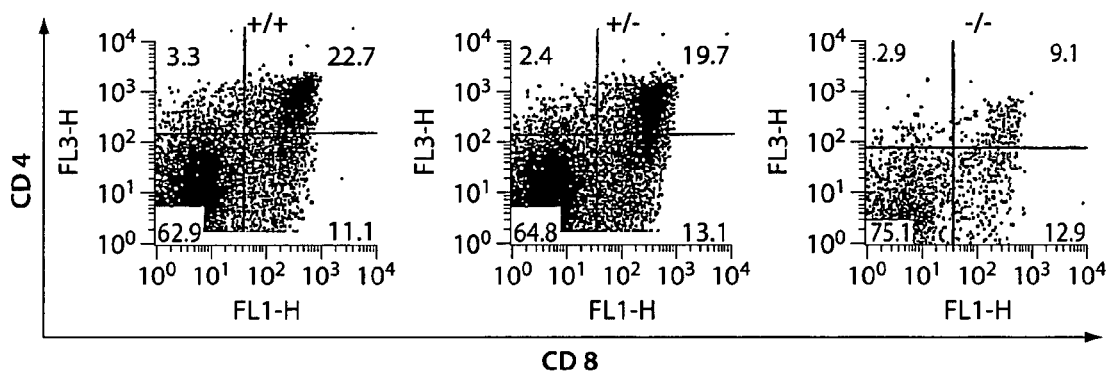
Figure 7C:
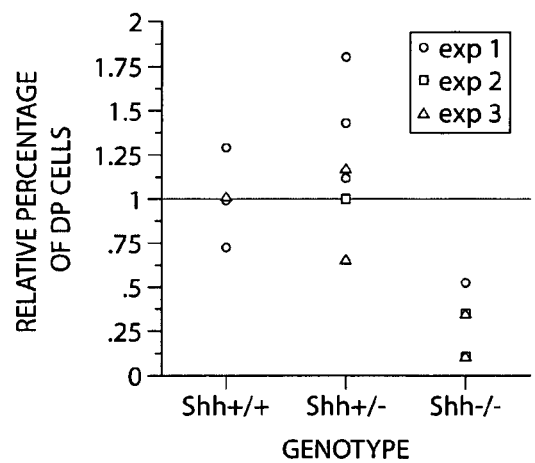

On E16.5 the proportion of DP cells was reduced in the Shh−/− thymi compared to littermates. In a typical experiment, only 9% of thymocytes were DP in the Shh−/− thymus compared to about 20% in +/+ and +/− littermates (FIG. 7). This decrease was accompanied by a concomitant increase in the proportion of DN cells (FIG. 7b). Analysis of the DN subsets showed similar proportions of DN3 and DN4 cells in the Shh−/− and littermate thymi. A reduction in thymocyte numbers and in the DP population was observed in all litters examined (FIG. 7a, b and c). The reduction in the percentage of DPs in the Shh−/− thymi could be the result of a partial arrest in differentiation at the transition from DN to DP cell, or be because the DP cells were dying. To test this, we analysed cell death by Annexin-V staining. There was no difference in the proportion of dying cells in the DP populations from Shh−/−, +/− and +/+ littermates (FIG. 7d). Interestingly, we found increased cell death in the DN4 population (FIG. 7e). 5.9% of Shh−/− DN4 cells stained positively with Annexin-V, compared to 2.5% and 1.6% in the +/− and +/+ DN4 populations respectively (FIG. 7e). These data are consistent with the reduction in DP cells being due to reduced differentiation from DN to DP cells. The increased death in the DN4 population could be due to the accumulation and subsequent death of cells that have failed to differentiate. These data suggest that Shh provides a survival signal for DN4 cells and are consistent with the reduced production of DP cells.

Shh−/− Thymi can Produce SP Cells In Vitro

Figure 8A:
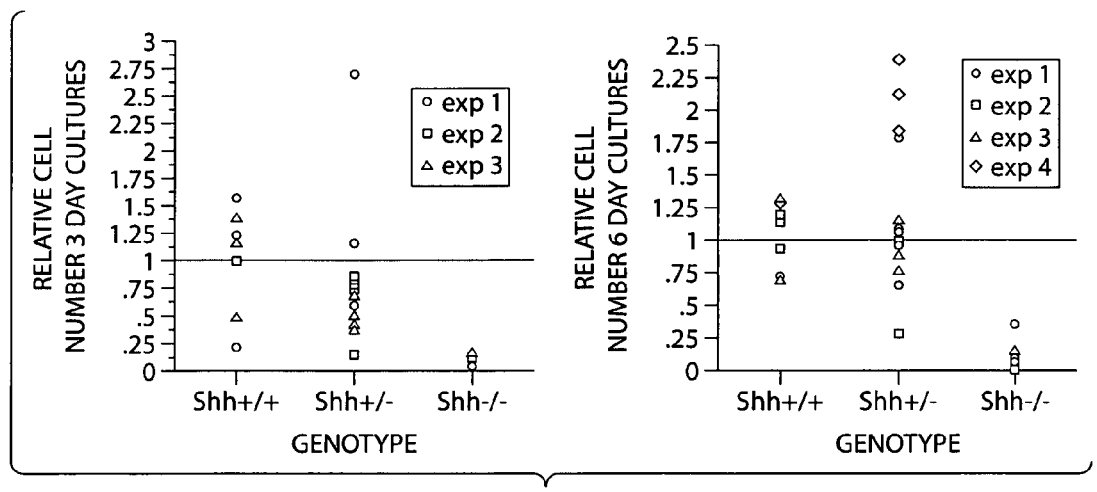
FIG. 8 FTOC from E14.5 Shh−/−, +/− and +/+. (A) Thymus cellularity in FTOC cultured for 3 days (left panel) and 6 days (right panel). To allow comparison between experiments, the number of cells recovered from each thymus explant was divided by the mean number of cells recovered from wildtype (littermate) thymus explants. The difference in cell number between Shh−/− and Shh+/+ thymus explants was statistically significant by Students t-test (p=0.0022 at Day 3, p=<0.0001 at Day 6). (B) Flow cytometry of 6 day FTOC stained with anti-CD4 and anti-CD8. The percentage of cells in each quadrant is given. Mean thymus size was ($\times 10^{-5}$), +/+1.8, +/−1.6 and −/−0.23. (C) The relative percentage of DP cells in 6 day FTOC. To allow comparison between experiments, the relative percentage of DP cells was calculated as in FIG. 7. There was no significant difference in the percentage of DP cells from Shh−/−, +/− or +/+ FTOC, by Students t-test. (D) CD3 staining on CD4 SP (upper row) and CD8 SP (lower row) from 6 day Shh+/+, +/− and −/− FTOC. Cells were stained with anti-CD4, anti-CD8 and anti-CD3 and gated on the SP populations. The percentage of cells in the marker is given.
Figure 8B:
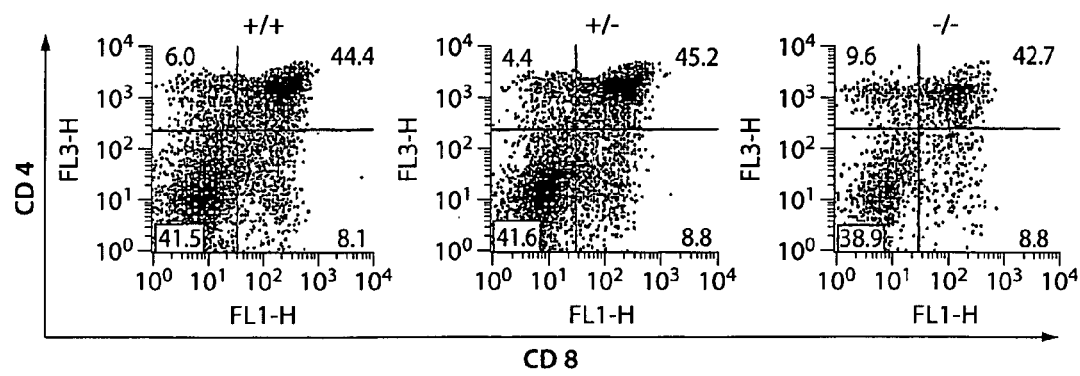
Figure 8C:
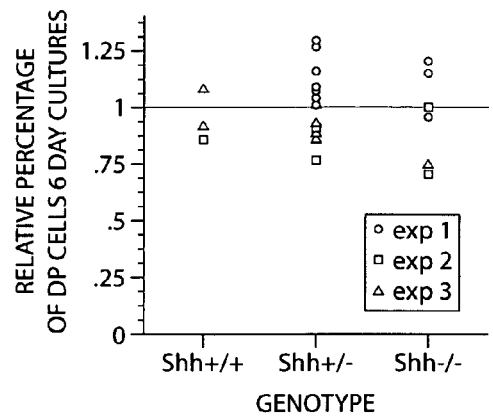
Figure 8D:
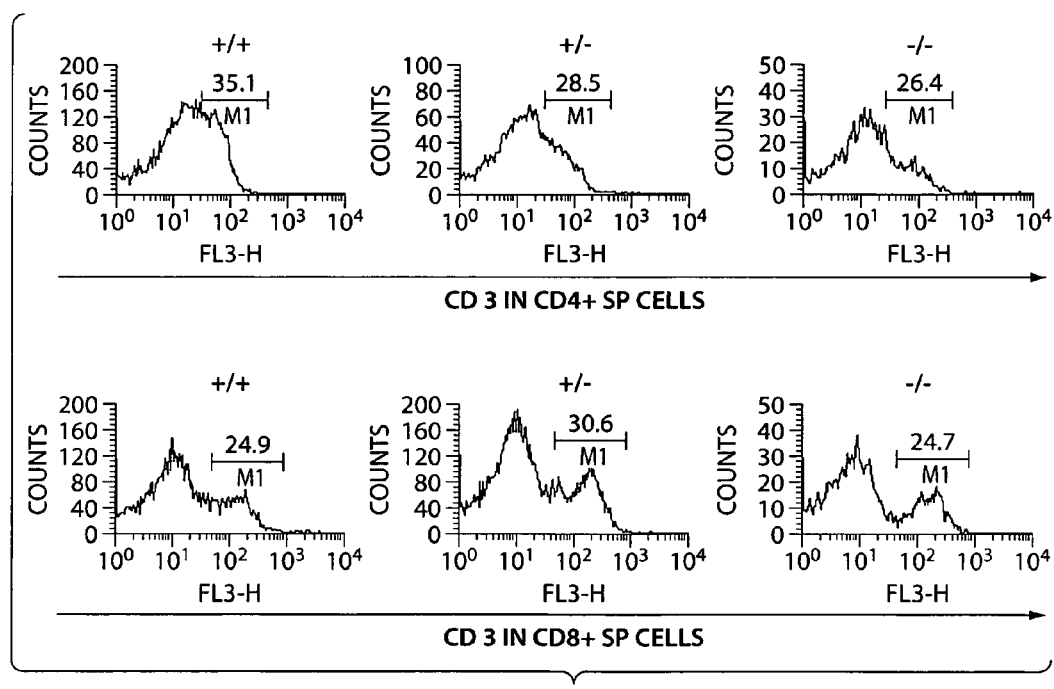

Shh−/− embryos die before birth (Chiang et al., 1996), and we did not find knock-out embryos in litters from E17.5 or later. Therefore, in order to study later stages of fetal thymus development, we cultured E14.5 thymi. After three days, cell recovery from the Shh−/− cultures was reduced in all experiments (FIG. 8a). After six days, cell number was still greatly reduced in the Shh−/− cultures (FIG. 8a), but there was no significant difference in the proportion of DP cells between the Shh−/−, +/− and +/+ cultures (FIGS. 8b and c). Analysis of the DN populations revealed an increase in the proportion of DN1 cells and a decrease in the proportion of CD25+ cells in the Shh−/− FTOC compared with littermate controls, consistent with the composition of DN subsets observed ex vivo. Thus, after the initial lag phase, DP cells were able to accumulate in the Shh−/− cultures. After the 6 day culture period SP cells had appeared in all cultures, and levels of CD3 expression on these cells were similar (FIG. 8d), indicating that cultures from Shh−/− were able to produce mature SP T cells.

Dose-Dependent Outcomes of Shh Signaling in Wild-Type FTOC

Figure 12A:
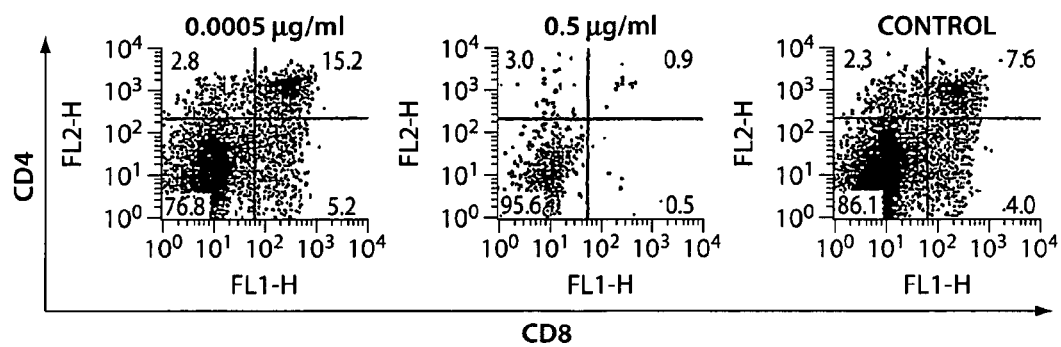
FIG. 12 In vitro, high dose Shh treatment arrests thymocyte development, but low dose treatment promotes it. A-C, Treatment of wild-type FTOC with recombinant Shh for 5 days. A) Expression of CD4 and CD8 in FTOC treated with 0.0005 or 0.5 µg/ml recombinant Shh and without recombinant Shh. The percentage of cells in each quadrant is given. B) Dose response to Shh. Left panel, Histogram to show the relative number of cells recovered from wild-type FTOC treated with 0.00005-0.5 µg/ml recombinant Shh and 0.5 µg/ml recombinant Shh in the presence of anti-Shh mAb. The number of cells recovered under each treatment condition was divided by the number of cells recovered from untreated FTOC. Right panel, Histogram to show the relative number of DP cells recovered from FTOC treated as described above. The number of DP cells recovered under each treatment condition was divided by the number of DP cells recovered from untreated FTOC. C) Relative cell recovery, calculated as described in B, from five independent experiments of wild-type FTOC treated with 0.0005 and 0.5 µg/ml recombinant Shh. The differences in cellularity between FTOC treated with 0.5 µg/ml recombinant Shh and control thymi and between FTOC treated with 0.0005 µg/ml recombinant Shh and control thymi were statistically significant by Student's t test (p<0.002 for 0.5 µg/ml; p<0.011 for 0.0005 µg/ml). D and E) Treatment of E14.5 Shh−/− FTOC with recombinant Shh for 7 days. D) Expression of CD4 and CD8 in Shh−/− FTOC treated with 0.0005 or 0.5 µg/ml recombinant Shh and without recombinant Shh. The percentage of cells in each quadrant is given. E) Upper panel, Relative cell recovery for the experiment shown in D) calculated relative to untreated cultures. Lower panel, Relative number of DP cells recovered for the experiment shown in D), calculated relative to control cultures. F) Left panel, Relative cell recovery from several independent experiments in which Shh−/− thymi were cultured with 0.0005 or 0.5 μg/ml Shh. For each thymus, one lobe was treated with Shh, and the other lobe was cultured without treatment. The relative cell number in the treated lobe was calculated relative to the cell recovery from the control lobe of the same thymus. The y-axis is a log scale to allow comparison between the two treatments. Right panel, Relative number of DP cells recovered from the same experiments. The y-axis is a log scale.
Figure 12B:
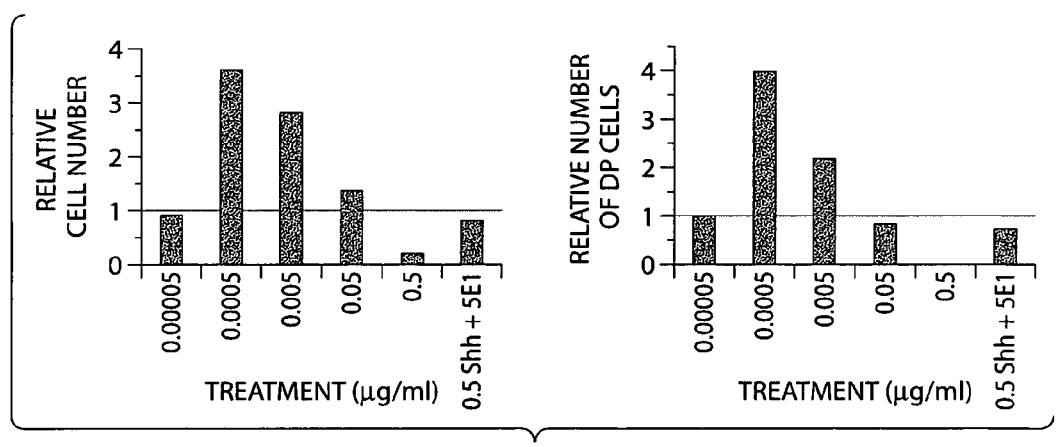
Figure 12C:
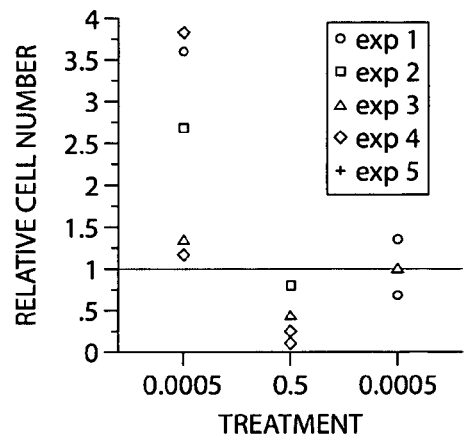
Figure 12D:
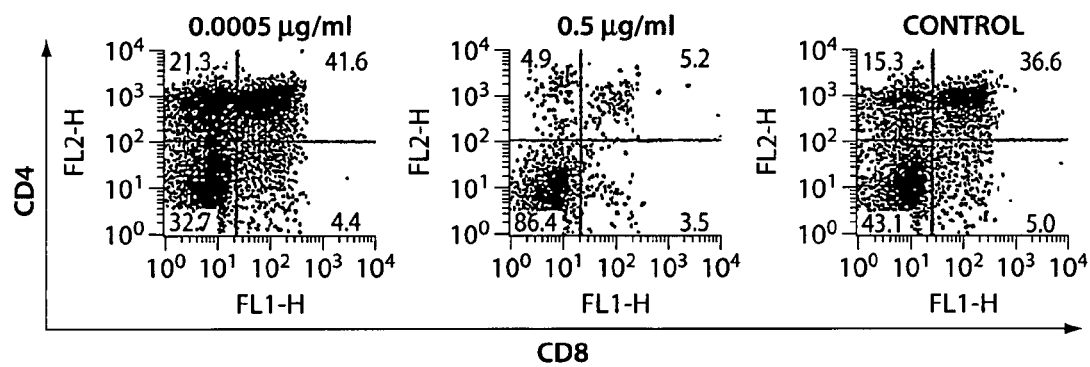
Figure 12E:
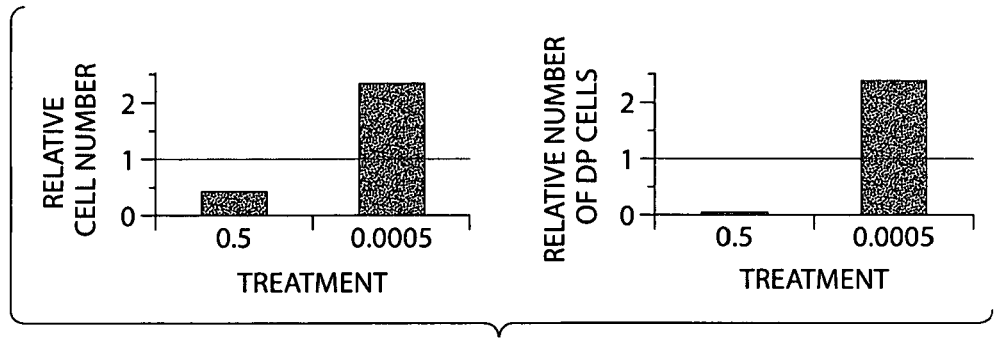

We have previously shown that treatment of wild-type FTOC with between 0.3 and 1 μg/ml recombinant Shh arrested thymocyte development at the DN stage (Outram et al., Immunity 13: 187, 2000). This arrest was not due to nonspecific toxicity of the recombinant Shh, but was a genuine biological effect, as it could be neutralized by addition of anti-Hh mAb. The analysis of E16.5 Shh−/− thymi suggested, however, that some Shh signaling is necessary at the transition from DN to DP cells (data not shown). Therefore, we decided to determine whether treatment of FTOC with lower concentrations of Shh could promote thymocyte development. We treated wild-type FTOC for 5 days with 0.0005 μg/ml Shh or 0.5 μg/ml Shh. In a typical experiment, treatment with 0.5 μg/ml Shh arrested thymocyte development at the DN stage, and <1% of thymocytes were DP compared with 7.6% in the control cultures, whereas treatment with 0.0005 μg/ml Shh promoted thymocyte development, and 15.2% of cells were DP (FIG. 12A). Treatment with 0.0005 μg/ml Shh also increased cell recovery relative to the control, and high dose treatment reduced cell recovery (FIG. 12, A-C). Titration of recombinant Shh in FTOC revealed that the dose range from 0.005-0.0005 μg/ml promoted thymocyte development, but this effect was lost in cultures treated with 0.00005 μg/ml (FIG. 12B). Treatment with 0.5 μg/ml inhibited both the production of DP cells and the overall cell recovery, and this inhibition was neutralized by addition of anti-Hh mAb, confirming that the arrest in thymocyte development was not the result of non-specific toxicity of the reagent (FIG. 12B). Thus, in wild-type FTOC, treatment with different concentrations of recombinant Shh can produce distinct outcomes at the transition from DN to DP cells; high-dose Shh treatment arrests thymocyte development, but treatment with a 1000-fold lower dose promotes the production of DP cells (FIG. 12, A-C).

Treatment with Shh Promotes Thymocyte Development in Shh−/− FTOC

Figure 9A:
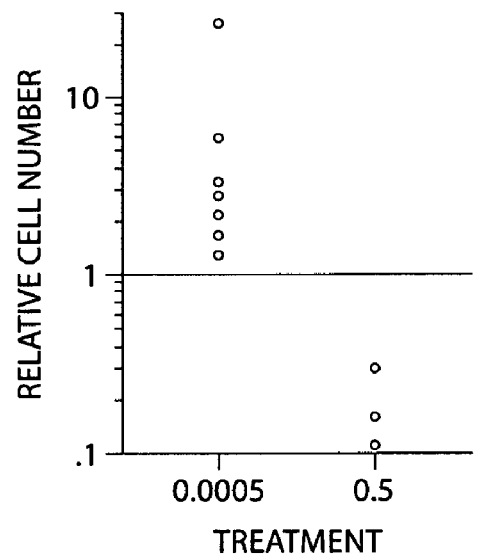
FIG. 9 Treatment of Shh−/− FTOC with recombinant Shh. (A) FTOC of E14.5 Shh−/− thymus. Thymus cellularity in Shh −/− FTOC treated for 7 days with 0.5 µg/ml or 0.0005 µg/ml recombinant Shh. From each thymus one lobe was treated with Shh and the other lobe was cultured without treatment. The relative cell number given is the number of cells recovered from the treated lobe divided by the number of cells recovered from the control lobe from the same thymus. The y-axis is a log scale. (B) The relative number of DP cells from Shh-treated and control thymus lobes from Shh−/− embryos. The relative number of DP cells is the number of DP cells recovered from the treated lobe divided by the number of DPs recovered from the control lobe from the same thymus.
Figure 9B:
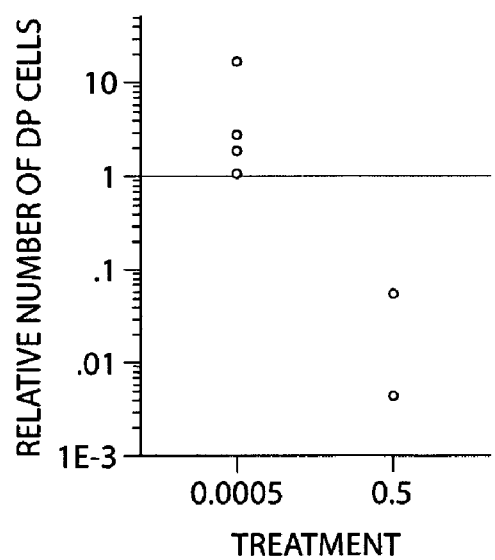

As thymocyte cellularity and differentiation were reduced in Shh−/− thymi, we examined if we could promote thymocyte development in Shh−/− thymus explants by treatment with recombinant Shh. We have previously shown that treatment of wildtype FTOC with between 0.3 to 1 μg/ml recombinant Shh arrested thymocyte development at the DN stage (Outram et al., 2000). Treatment of Shh−/− thymus explants with 0.5 μg/ml Shh also inhibited differentiation from DN to DP cell (FIGS. 9a and b). We treated Shh−/− thymus explants for 7 days with 0.5 or 0.0005 μg/ml recombinant Shh. Treatment with 0.5 μg/ml Shh inhibited differentiation from DN to DP cells. In a typical experiment, 5.2% of thymocytes were DP in the treated cultures compared with 36.6% in control cultures (FIG. 12, D and E). Thus, Shh−/− thymocytes were able to respond to a Shh signal in the same way as wildtype thymocytes, despite the fact that they had not been exposed to Shh in vivo. Although this high dose of Shh arrested thymocyte differentiation, some activation of the Hh signalling pathway is clearly necessary for normal thymocyte differentiation. We therefore treated Shh−/− explants with a 1000-fold lower dose of recombinant Shh (0.0005 μg/ml). Treatment of Shh−/− thymus explants with low-dose Shh promoted differentiation to DP cell: After 7 days in culture Shh−/− thymus explants treated with 0.0005 μg/ml Shh contained more DP thymocytes than untreated Shh−/− thymus explants −41.6% DP thymocytes and 32.7% DN thymocytes in treated Shh−/− thymus explants, compared with 36.6% DP cells and 43.1% DN cells in untreated control Shh−/− thymus cultures (FIG. 9b). Cell number was also increased in the Shh−/− thymus explants treated with low-dose Shh, compared to control in all experiments (FIG. 9a), so that overall the low dose treatment more than doubled the production of DP cells (summarized in FIG. 12E).

Figure 12F:
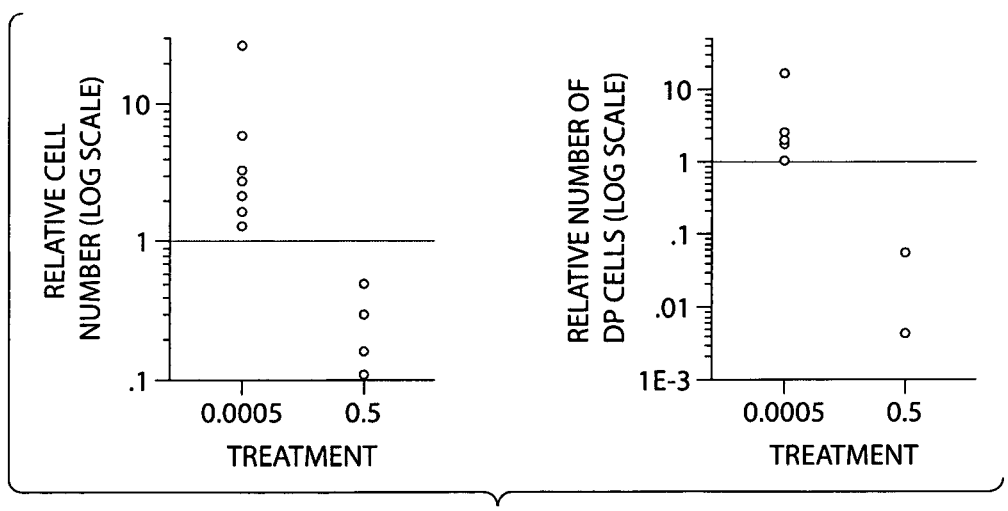

We repeated these experiments by treating individual Shh−/− thymus lobes with recombinant Shh and comparing them to untreated cultures of the other lobe from the same embryo (summarized in FIG. 12F, cell production in each culture condition compared with that in the control lobe are shown on a log scale). These cultures confirmed that in all cases low dose Shh treatment increased both cell recovery and the production of DP cells compared with the control lobe from the same embryo. In contrast, high dose Shh treatment inhibited both overall cell production and differentiation to DP cell (FIG. 12F).

Shh−/− Fetal Liver can Reconstitute Wildtype Irradiated Thymus

Figure 10A:
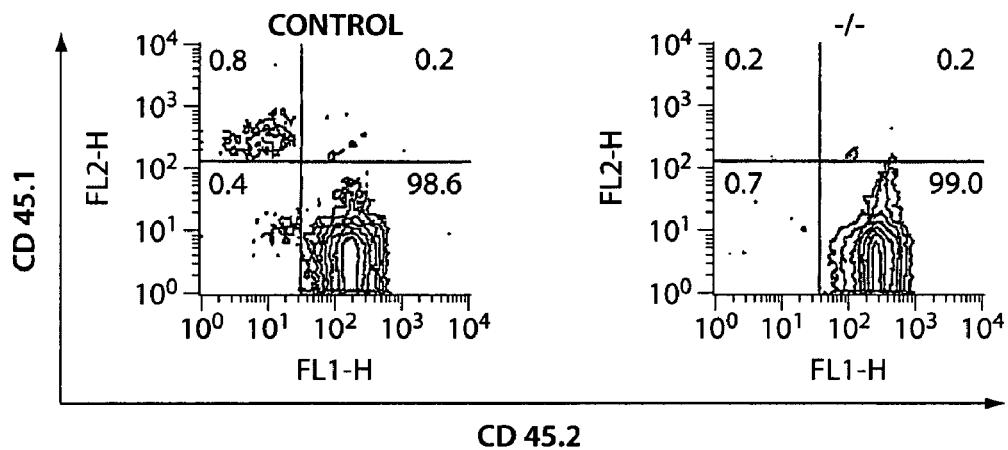
FIG. 10 Shh−/− fetal liver cells can reconstitute the thymus in irradiation chimeras. Irradiated SJL mice (CD45.1+) were reconstituted with Shh−/− and littermate fetal liver cells (CD45.2+) and the reconstituted thymi were analysed by flow cytometry after two months. (A) To assess the ability of Shh−/− cells to reconstitute the thymus, thymi were stained with anti-CD45.1 and anti-CD45.2. Expression of CD45.1 and CD45.2 are shown and the percentage of cells in each quadrant is given. Mean thymus size was (×10-7), Control 2.5 (+/−0.53) and knockout 2.6 (+/−0.2). (B) Expression of CD4 and CD8 gated on CD45.2 positive cells. The percentage of cells in each quadrant is given. (C) Expression of CD25 gated on donor-origin DN cells. Thymocytes were stained with anti-CD45.1, anti-CD4, anti-CD8, anti-CD3 and anti-CD25. The expression of CD25 on cells gated to be CD4−, CD8−, CD3− and CD45.1− is shown. The percentage of cells in each marker is given. (D) Expression of CD3 gated on CD45.2 positive cells. The percentage of cells in each marker is given.
Figure 10B:
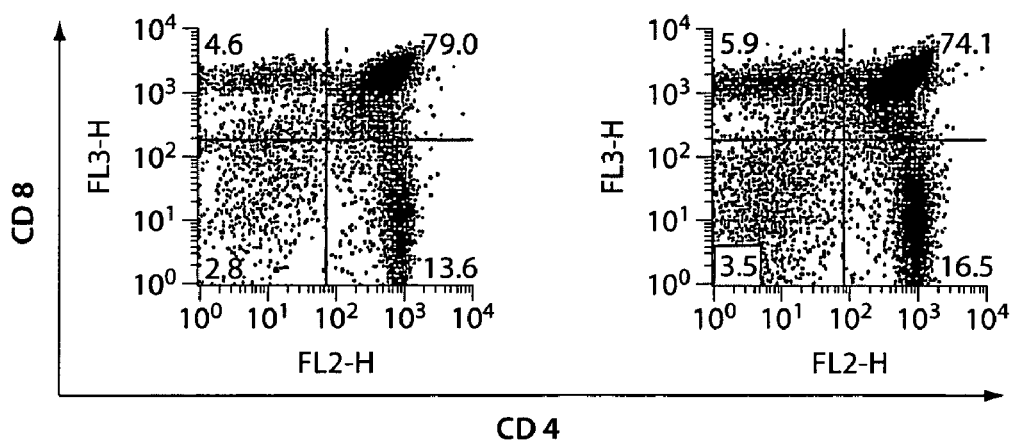
Figure 10C:
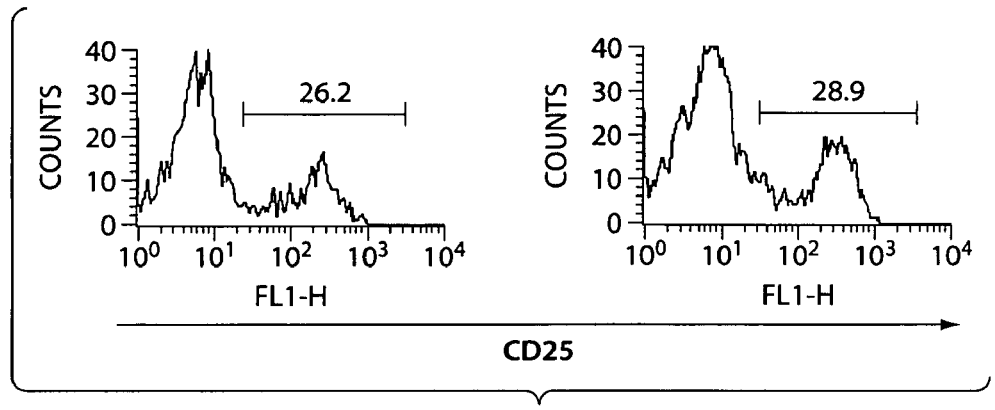
Figure 10D:
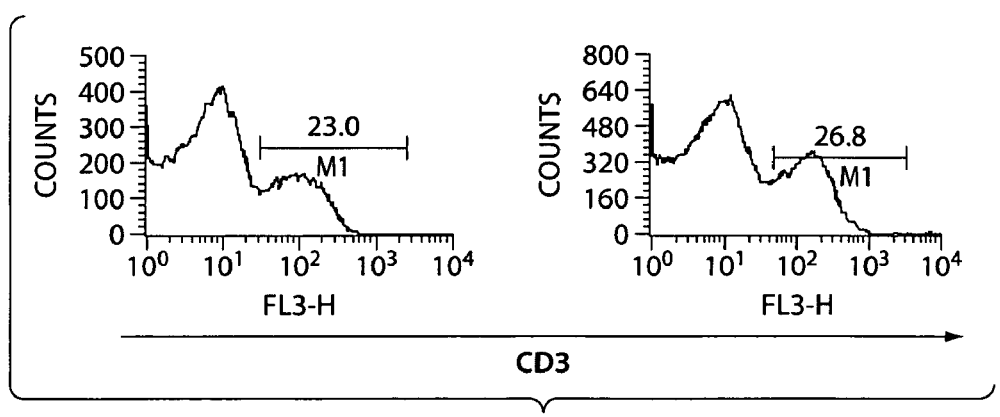

In the thymus, Shh is produced by the thymic stroma, as evidenced by both RT-PCR from 2',4'-deoxyguanosine-resistant (stromal fraction) fetal thymus explants and immunohistochemistry of adult thymus sections, in which anti-Shh staining colocalized with anticytokeratin staining (16, 33). However, Shh has also been shown to regulate the expansion of primitive human hemopoietic cells in an autocrine manner (17). On E13.5 the number and proportion of hemopoietic (CD45+) cells in the Shh−/− thymus were greatly reduced relative to littermates (FIG. 5). It therefore seemed possible that Shh might also be produced by the earliest thymocyte progenitors and regulate their expansion and differentiation in an autocrine manner. Thus, the reduction in thymocyte development found in the Shh−/− embryos on E13.5 might be the result of a failure of hematopoietic stem cells to expand or enter the thymus, or of early thymocyte progenitors to make Shh, rather than because of lack of Shh production by the thymic stroma. To test whether Shh−/− fetal liver cells were able to enter and fully repopulate an adult Shh-expressing thymus, we reconstituted irradiated adult mice with fetal liver cells from Shh−/− embryos. Adult SJL mice (CD45.1+) were irradiated with 1100 rads and injected intravenously with fetal liver cells from E12.5 Shh−/− or littermate embryos (CD45.2+). After two months the thymus had fully reconstituted, and there was no difference in thymus cellularity or thymocyte differentiation between mice reconstituted with Shh−/− or littermate fetal liver cells (FIG. 10). Staining with anti-CD45.1 (host origin) and anti-CD45.2 (donor origin) indicated that more than 98% of thymocytes were of donor origin (FIG. 10a). Three colour flow cytometry using antibodies directed against CD4, CD8 and CD45.2 indicated that the Shh−/− fetal liver cells were able to give rise to DN, DP and SP populations in normal ratios (FIG. 10b). To analyze expression of CD25 in the DN cells, we stained with anti-CD4, anti-CD8, anti-CD45.1 and anti-CD25 and excluded cells that stained positive with anti-CD4, anti-CD8 and anti-CD45.1. In both Shh−/− reconstituted and control reconstituted thymus about 25% of DN cells expressed cell surface CD25 (FIG. 10c). Comparison of CD3 expression, gated on the CD45.2+ cells, showed no significant difference between Shh−/− reconstituted and control reconstituted thymi (FIG. 10d). Thus, Shh−/− fetal liver cells were able to reconstitute an irradiated wild-type thymus in which thymic stroma produce Shh, indicating that Shh−/− fetal liver cells were able to survive and home to the thymus and that autocrine Shh production is not essential for their maintenance in the thymus, because they can receive necessary Hh signals from the adult thymic stroma.

This analysis of Shh−/− embryos demonstrates that Shh is importantin the expansion and development of DN thymocytes. We have identified two stages at which Shh seems to be necessary for normal thymocyte development (FIG. 11). The transition from DN1 to DN2 cell is severely impeded in knockout thymi. The DN3 population then seems to partially recover, but a second bottleneck in development occurs at the transition to DP cell, and there is an increase in cell death of the DN4 population. Shh signaling does not seem to be essential beyond the DP stage of thymocyte development, as after 6 days in culture Shh−/− FTOC were able to partially recover, producing approximately one-fifth the number of SP cells as +/+ littermate thymi. It is possible, however, that there is redundancy between Hh family members in the thymus, and that Ihh functions at later stages of T cell development.

Figure 11A:
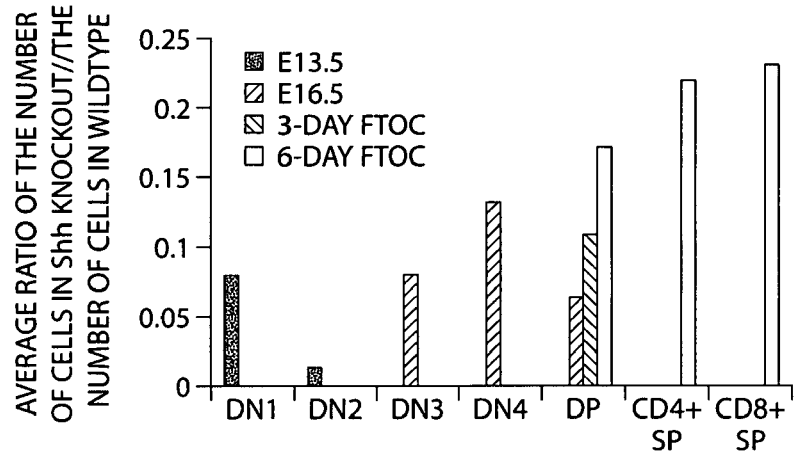
FIG. 11 (A) The histogram collates the average ratio of the absolute number of cells in different thymocyte populations from various experiments of Shh−/−, +/+, demonstrating the reduction in differentiation from DN1 to DN2 and from DN4 to DP, and the accumulation of DN4 cells. (B) Proposed model for the functions of Shh in thymocyte development. Shh produced by the thymic epithelium promotes DN cell proliferation, and differentiation from DN1 to DN2 and from DN4 to DP.

Comparison of the size of the different thymocyte populations between the Shh−/− and +/+ littermates highlights the fact that these two transitions in thymocyte development require Shh (FIG. 11a). Differentiation from DN1 to DN2 cell is severely impeded in the knockout thymi. The DN3 population then seems to partially recover, but a second bottleneck in development occurs at the transition to DP cell, and there is an accumulation of DN4 cells. Shh signalling does not seem to be essential beyond the DP stage of thymocyte development, as after 6 days in culture Shh−/− FTOC were able to partially recover, producing about ⅕ the number of SP cells as littermate thymi.

The reduced differentiation from DN1 to DN2 in the Shh−/− thymus suggests that Shh is involved in T cell lineage commitment, as the DN 1 population contains multipotent cells that are not yet committed to the T cell lineage (Akashi et al., 2000). Both Notch1 (Radtke et al., 1999) and the Wnt signalling pathway (Staal and Clevers, 2003) are required for this transition, whereas in vitro Bone morphogenetic protein 4 (BMP4) arrests differentiation at the DN1 stage (Hager-Theodorides et al., 2002). These pathways interact with one another in the development of many tissues (Varas et al., 2003), and it will be interesting to analyze the relationship between these different molecules in the control of T cell lineage commitment.

We have previously shown that in vitro treatment of FTOC with recombinant Shh arrested thymocyte development at the DN3 stage, after TCRβ chain gene rearrangement, whereas treatment of FTOC with a neutralising anti-Hh antibody accelerated thymocyte differentiation to the DP stage, but did not replace the need for a pre-TCR signal (Outram et al., 2000). Therefore, the reduced differentiation to DP cell in the Shh−/− thymus seemed surprising. While not wishing to be bound by specific theories, there could be two possible explanations for this observation from these experimental systems: (1) The analysis of the Shh−/− embryos indicated that Shh signalling is important very early in thymocyte development (prior to pre-TCR signalling). Thus, production of DP cells in the Shh−/− thymus might be reduced because fewer thymocytes were reaching the stage at which they could transduce the pre-TCR signal, rather than because the pre-TCR signal itself required some input from the Hh signalling pathway. In this case, treatment with low dose Shh might promote thymocyte development at an early stage, before pre-TCR signaling, whereas we have previously shown that neutralization of Hh signaling by treatment with anti-Hh acts after pre-TCR signaling during the transition to DP cell. (2) Alternatively, it is possible that different concentrations of Shh produce distinct outcomes at the transition from DN to DP cell. Classical morphogens specify different cell fates in a concentration dependent manner (Gurdon and Bourillot, 2001), and different doses of Shh have been shown to produce distinct cellular fates in the developing neural tube (Briscoe and Ericson, 2001). It is possible that while addition of a high dose of recombinant Shh arrests thymocyte development and counteracts the pre-TCR signal (Outram et al., 2000), some activation of the Hh pathway is necessary for successful pre-TCR signalling or for survival of DN4 thymocytes. In wild-type FTOC neutralisation of Hh signalling by antibody treatment accelerated differentiation to DP cell (Outram et al., 2000), but antibody treatment would presumably greatly lower the dose of available Shh but not neutralise all molecules. When we treated Shh−/− thymus explants with very low dose recombinant Shh (¹⁄₁₀₀₀th the arresting dose), thymocyte development was promoted and the production of DP cells was increased. It remains to be determined if this low dose was acting directly at the transition to DP cell, or if its effects were due to its action on earlier DN cells.

The Shh−/− thymi had greatly reduced cellularity at all developmental stages examined. Shh−/− embryos are smaller than those of their littermates, but it seems unlikely that the reduction in thymus cellularity was wholly due to the small size of the embryos. For example, on E13.5, thymocyte numbers were reduced by between 17- and 6-fold compared with those of their littermates (FIG. 5), but the length of the embryos was 70% that of their littermates, and another hemopoietic organ, fetal liver, contained the same number of cells as in littermates (unpublished observations). Likewise, the fact that treatment of thymus explants with recombinant Shh is able to increase the production of DP thymocytes in vitro shows that the phenotype of the Shh−/− thymus cannot be simply explained by the general runtiness of the embryo.

Figure 11B:
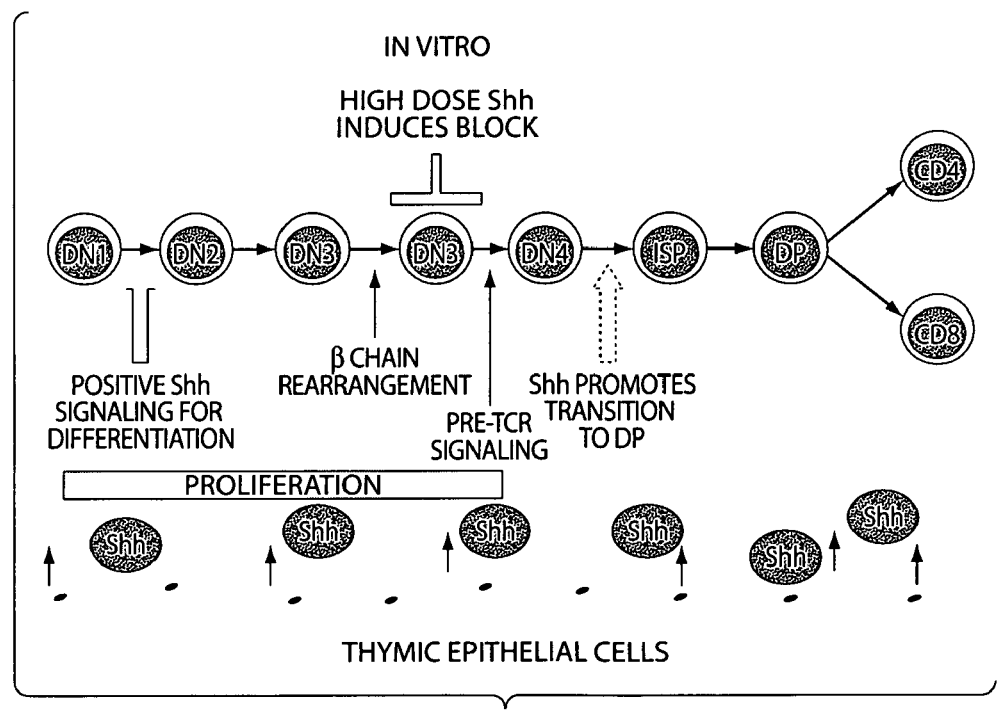

In summary, we provide genetic evidence that Shh has a non-redundant function in the control of thymocyte development in vivo. Shh is required for proliferation and efficient differentiation of DN cells, and in the regulation of thymus cellularity. Shh, produced by the thymic stroma, provides signals for the transition from DN1 to DN2 cells, proliferation of DN cells, and promotes the production of DP cells (FIG. 11b).

Experimental Procedures

Mice

C57BL/6 mice were purchased from B & K Universal Ltd (UK). Shh+/− mice were a kind gift from Professor Philip Beachy, John Hopkins University (Chiang et al., 1996). Shh+/− were backcrossed onto C57BL/6 mice for at least five generations. SJL mice were purchased from Harlan Olac. All mice were bred and maintained in individually ventilated cages at the Central Biomedical Services unit at Imperial College, London.

Timed mates were performed by mating a male with two females and monitoring the females for plugs. The day the plug were found was counted as E 0.5.

Foetal liver Chimeric mice were generated by irradiating SJL mice with 1100 rads and injecting them with 200 µl of E12.5 Shh +/+, +/− and −/− fetal liver cells on the following day. Mice were then maintained for a further eight weeks before analysis.

Flow Cytometry and Antibodies

Thymocyte suspensions were prepared by crushing thymi between two pieces of ground glass. Cells were stained using combinations of the following directly conjugated antibodies obtained from BD Pharmingen: anti-CD44FITC, anti-CD44Cychrome, anti-CD25 PE, anti-CD25 FITC, anti-CD4FITC, anti-CD8 Cychrome, anti-CD4PE, anti-CD4Cychrome, anti-CD8FITC, anti-CD45.1PE, anti-CD45.2FITC, anti-CD3PE and anti-TCR-βPE. Cell suspensions were stained with the antibodies for 30 minutes on ice in 50 µl of Dulbeccos modified medium (Life Technologies), supplemented with 5% FCS and 0.1% sodium azide. Cells were washed in this medium between incubations and prior to analysis on the FACScan (Becton Dickinson). Events were collected in list mode using CellQuest software and data analysed using CellQuest Pro software. Live cells were gated according to their FSC and SSC profiles. Data are representative of at least three experiments.

Propidium iodide (PI) staining was carried out on cells treated with 100 µg/ml RNAse (Sigma) and permeabilised in 0.1% Triton X-100, as described previously (Hager-Theodorides et al., 2002).

Annexin-V staining was carried out using an Annexin-V-FITC apoptosis detection kit (BD Pharmingen), according to the manufacturers instructions. Prior to Annexin-V staining, cells were stained as described above.

FTOC

Fetal thymi were dissected from E14.5 Shh +/+, +/− and −/− mice and cultured on 8 µm pore size Millipore filters (Millipore) in AIM-V serum free medium (Life Technologies). Thymi were cultured at 37° C. and 5% $CO_2$ for 3 or 6 days or cultured in the presence of 0.5 µg/ml or 0.0005 µg/ml modified human Shh (Curis) for 7 days.

Modified human Shh was a kind gift from Curis. The Shh was octylated for high activity. In vitro modification of N-Shh (amino acids 25-199) with a lipophilic group on the amino-terminal cysteine significantly increases the specific activity (>30 fold) of E. coli-derived N-shh as measured by activation of Hh signal transduction in cultured cells (Pepinsky et al., 1998). Octyl N-shh is a hydrophobically modified version of the Shh signalling protein generated by coupling N-octyl-malemide to the amino-terminal cysteine of bacterially derived N-shh.

PCR Analysis

DNA was extracted from embryonic head tissue for PCR by digesting tissues in Lysis buffer containing 50 mM KCl, 1.5 mM $MgCl_2$, 10 mM Tris-HCl pH 8.5, 0.01% Gelatin, 0.45% NP-40, 0.45% Tween-20 and 100 µg/ml Proteinase K (Sigma) in water. 0.5 µg DNA was used as a template in each Polymerase chain reaction. The primers to amplify the inserted neomycin cassette were forward: CTGTGCTC-GACGTTGTCACTG (SEQ ID NO: 29), and reverse: GATC-CCCTCAGAAGAACTCGT (SEQ ID NO: 30) (Chiang et al., 1996). Reactions were run on a Stratagene Robocycler as follows: 5 mins at 94° C., 32 cycles of 1 min at 94° C., 1 min at 66° C., and 1 min at 72° C. and 10 mins at 72° C. DNA products were resolved on a 2% agarose gel.

REFERENCES

Akashi, K., Reya, T., Dalma-Weiszhausz, D., and Weissman, I. L. (2000). Lymphoid precursors. Curr Opin Immunol 12, 144-150.

Alcedo, J., Ayzenzon, M., Von Ohlen, T., Noll, M., and Hooper, J. E. (1996). The *Drosophila* smoothened gene encodes a seven-pass membrane protein, a putative receptor for the hedgehog signal. Cell 86, 221-232.

Anderson, G., Moore, N. C., Owen, J. J., and Jenkinson, E. J. (1996). Cellular interactions in thymocyte development. Annu Rev Immunol 14, 73-99.

Asamoto, H., and Mandel, T. E. (1981). Thymus in mice bearing the Steel mutation. Morphologic studies on fetal, neonatal, organ-cultured, and grafted fetal thymus. Lab Invest 45, 418-426.

Bhardwaj, G., Murdoch, B., Wu, D., Baker, D. P., Williams, K. P., Chadwick, K., Ling, L. E., Karanu, F. N., and Bhatia, M. (2001). Sonic hedgehog induces the proliferation of primitive human hematopoietic cells via BMP regulation. Nat Immunol 2, 172-180.

Briscoe, J., and Ericson, J. (2001). Specification of neuronal fates in the ventral neural tube. Curr Opin Neurobiol 11, 43-49.

Cao, X., Shores, E. W., Hu-Li, J., Anver, M. R., Kelsall, B. L., Russell, S. M., Drago, J., Noguchi, M., Grinberg, A., Bloom, E. T., and et al. (1995). Defective lymphoid development in mice lacking expression of the common cytokine receptor gamma chain. Immunity 2, 223-238.

Ceredig, R., and Rolink, T. (2002). A positive look at double-negative thymocytes. Nat Rev Immunol 2, 888-897.

Chen, Y., and Struhl, G. (1998). In vivo evidence that Patched and Smoothened constitute distinct binding and transducing components of a Hedgehog receptor complex. Development 125, 4943-4948.

Chiang, C., Litingtung, Y., Lee, E., Young, K. E., Corden, J. L., Westphal, H., and Beachy, P. A. (1996). Cyclopia and defective axial patterning in mice lacking Sonic hedgehog gene function. Nature 383, 407-413.

Denef, N., Neubuser, D., Perez, L., and Cohen, S. M. (2000). Hedgehog induces opposite changes in turnover and sub-cellular localization of patched and smoothened. Cell 102, 521-531.

Di Santo, J. P., Kuhn, R., and Muller, W. (1995). Common cytokine receptor gamma chain (gamma c)-dependent cytokines: understanding in vivo functions by gene targeting. Immunol Rev 148, 19-34.

Duman-Scheel, M., Weng, L., Xin, S., and Du, W. (2002). Hedgehog regulates cell growth and proliferation by inducing Cyclin D and Cyclin E. Nature 417, 299-304.

Goodrich, L. V., Johnson, R. L., Milenkovic, L., McMahon, J. A., and Scott, M. P. (1996). Conservation of the hedgehog/patched signaling pathway from flies to mice: induction of a mouse patched gene by Hedgehog. Genes Dev 10, 301-312.

Gurdon, J. B., and Bourillot, P. Y. (2001). Morphogen gradient interpretation. Nature 413, 797-803.

Hager-Theodorides, A. L., Outram, S. V., Shah, D. K., Sacedon, R., Shrimpton, R. E., Vicente, A., Varas, A., and Crompton, T. (2002). Bone morphogenetic protein 2/4 signaling regulates early thymocyte differentiation. J Immunol 169, 5496-5504.

Ingham, P. W., and McMahon, A. P. (2001). Hedgehog signaling in animal development: paradigms and principles. Genes Dev 15, 3059-3087.

Kawamoto, H., Ikawa, T., Ohmura, K., Fujimoto, S., and Katsura, Y. (2000). T cell progenitors emerge earlier than B cell progenitors in the murine fetal liver. Immunity 12, 441-450.

Koebernick, K., and Pieler, T. (2002). Gli-type zinc finger proteins as bipotential transducers of Hedgehog signaling. Differentiation 70, 69-76.

Marigo, V., Davey, R. A., Zuo, Y., Cunningham, J. M., and Tabin, C. J. (1996). Biochemical evidence that patched is the Hedgehog receptor. Nature 384, 176-179.

Metcalf, D. (1963). The autonomous behaviour of normal thymus grafts. Australian Journal of experimental biology 41, 437-448.

Moore, T. A., and Zlotnik, A. (1995). T-cell lineage commitment and cytokine responses of thymic progenitors. Blood 86, 1850-1860.

Outram, S. V., Varas, A., Pepicelli, C. V., and Crompton, T. (2000). Hedgehog signaling regulates differentiation from double-negative to double-positive thymocyte. Immunity 13, 187-197.

Pepinsky, R. B., Zeng, C., Wen, D., Rayhom, P., Baker, D. P., Williams, K. P., Bixler, S. A., Ambrose, C. M., Garber, E. A., Miatkowski, K., et al. (1998). Identification of a palmitic acid-modified form of human Sonic hedgehog. J Biol Chem 273, 14037-14045.

Peschon, J. J., Morrissey, P. J., Grabstein, K. H., Ramsdell, F. J., Maraskovsky, E., Gliniak, B. C., Park, L. S., Ziegler, S. F., Williams, D. E., Ware, C. B., and et al. (1994). Early lymphocyte expansion is severely impaired in interleukin 7 receptor-deficient mice. J Exp Med 180, 1955-1960.

Radtke, F., Wilson, A., Stark, G., Bauer, M., van Meerwijk, J., MacDonald, H. R., and Aguet, M. (1999). Deficient T cell fate specification in mice with an induced inactivation of Notch1. Immunity 10, 547-558.

Rodewald, H. R., Ogawa, M., Haller, C., Waskow, C., and DiSanto, J. P. (1997). Pro-thymocyte expansion by c-kit and the common cytokine receptor gamma chain is essential for repertoire formation. Immunity 6, 265-272.

Roy, S., and Ingham, P. W. (2002). Hedgehogs tryst with the cell cycle. J Cell Sci 115, 4393-4397.

Ruiz i Altaba, A. (1999). Gli proteins and Hedgehog signaling: development and cancer. Trends Genet 15, 418-425.

Staal, F. J., and Clevers, H. C. (2003). Wnt signaling in the thymus. Curr Opin Immunol 15, 204-208.

Stone, D. M., Hynes, M., Armanini, M., Swanson, T. A., Gu, Q., Johnson, R. L., Scott, M. P., Pennica, D., Goddard, A., Phillips, H., et al. (1996). The tumour-suppressor gene patched encodes a candidate receptor for Sonic hedgehog. Nature 384, 129-134.

Taipale, J., Cooper, M. K., Maiti, T., and Beachy, P. A. (2002). Patched acts catalytically to suppress the activity of Smoothened. Nature 418, 892-897.

van den Heuvel, M., and Ingham, P. W. (1996). smoothened encodes a receptor-like serpentine protein required for hedgehog signalling. Nature 382, 547-551.

Varas, A., Hager-Theodorides, A. L., Sacedon, R., Vicente, A., Zapata, A. G., and Crompton, T. (2003). The role of morphogens in T-cell development. Trends Immunol 24, 197-206.

Von Boehmer, H., Aifantis, I., Gounari, F., Azogui, O., Haughn, L., Apostolou, I., Jaeckel, E., Grassi, F., and Klein, L. (2003). Thymic selection revisited: how essential is it? Immunol Rev 191, 62-78.

von Freeden-Jeffry, U., Vieira, P., Lucian, L. A., McNeil, T., Burdach, S. E., and Murray, R. (1995). Lymphopenia in interleukin (IL)-7 gene-deleted mice identifies IL-7 as a nonredundant cytokine. J Exp Med 181, 1519-1526.

Wu, L., Li, C. L., and Shortman, K. (1996). Thymic dendritic cell precursors: relationship to the T lymphocyte lineage and phenotype of the dendritic cell progeny. J Exp Med 184, 903-911.

Zlotnik, A., and Moore, T. A. (1995). Cytokine production and requirements during T-cell development. Curr Opin Immunol 7, 206-213.

All of the above-cited references, patents and publications are hereby incorporated by reference.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

I claim:

1. A method for promoting thymic T cell maturation in an animal in need thereof, comprising administering to said animal a hedgehog (HH) antagonist in an amount sufficient to promote T cell maturation in the thymus of said animal, whereby said antagonist promotes T cell maturation in the thymus; and wherein said HH antagonist is an anti-hedgehog antibody.

2. The method of claim 1, wherein administration of said hedgehog antagonist reduces hedgehog signaling to a level that is sufficient for T cell maturation in the thymus.

3. The method of claim 1, wherein said hedgehog antagonist is administered directly and locally to the thymus of said animal.

4. The method of claim 1, wherein said hedgehog antagonist is an anti-Sonic hedgehog antibody antagonist.

5. The method of claim 1, wherein said antibody is a monoclonal antibody.

6. The method of claim 1, wherein said antibody is a humanized antibody.

* * * * *